US006902918B1

(12) United States Patent
Arnold et al.

(10) Patent No.: US 6,902,918 B1
(45) Date of Patent: Jun. 7, 2005

(54) OXYGENASE ENZYMES AND SCREENING METHOD

(75) Inventors: Frances H. Arnold, Pasadena, CA (US); Hyun Joo, Suwon (KR); Zhanglin Lin, Beijing (CN)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/246,451

(22) Filed: Feb. 9, 1999

Related U.S. Application Data

(60) Provisional application No. 60/094,403, filed on Jul. 28, 1998, provisional application No. 60/106,840, filed on Nov. 3, 1998, provisional application No. 60/086,206, filed on May 21, 1998, and provisional application No. 60/106,834, filed on Nov. 3, 1998.

(51) Int. Cl.$^7$ .......................... C12N 9/00; C12N 9/02; C12N 1/20; C12N 15/00; C07H 21/04

(52) U.S. Cl. .............................. 435/189; 435/4; 435/6; 435/25; 435/69.1; 435/183; 435/252.3; 435/320.1; 536/23.2; 536/23.4; 536/23.7

(58) Field of Search ...................... 435/4, 6, 25, 69.1, 435/183, 189, 252.3, 320.1, 193, 194, 200; 536/23.2

(56) References Cited

U.S. PATENT DOCUMENTS

| | | |
|---|---|---|
| 5,605,793 A | 2/1997 | Stemmer |
| 5,741,691 A | 4/1998 | Arnold et al. |
| 5,811,238 A | 9/1998 | Stemmer et al. |
| 5,830,721 A | 11/1998 | Stemmer et al. |
| 5,837,458 A | 11/1998 | Minshull et al. |
| 5,965,408 A | 10/1999 | Short |

FOREIGN PATENT DOCUMENTS

| | | | |
|---|---|---|---|
| EP | 0 505 198 A | | 9/1992 |
| WO | WO 95/22625 | | 8/1995 |
| WO | WO 97/16553 | * | 5/1997 |
| WO | WO 97/20078 | | 6/1997 |
| WO | WO 97/35957 | | 10/1997 |
| WO | WO 97/35966 | | 10/1997 |
| WO | WO 98/27230 | | 6/1998 |
| WO | WO 98/31837 | | 7/1998 |
| WO | WO 98/41653 | | 9/1998 |
| WO | WO 98/42832 | | 10/1998 |
| WO | WO 00/00632 | | 1/2000 |
| WO | WO 00/04190 | | 1/2000 |
| WO | WO 00/06718 | | 2/2000 |
| WO | WO 00/09679 | | 2/2000 |
| WO | WO 00/18906 | | 4/2000 |

OTHER PUBLICATIONS

Manchester et al. Biochimie, 1996, vol. 78:714–722.*
Manchester et al. Protein Engineering, 1995, vol. 8(8):801–807.*
Chang et al., Nature Biotechnol 1999;17:793–797.
Christians et al., Nature Biotechnol 1999;17:259–264.
Crameri et al., Nature Med 1996;2(1):100–106.
Crameri et al., Nature Biotechnol 1997;15:436–438.
Crameri et al., Nature 1998;391:288–291.
De Haan et al., Biochim Biophys Acta. 1969;180:417–9.
Lipscomb et al., J. Biol. Chem. 1976;251:1116.
Minshull and Stemmer, Curr Opin Chem Biol 1999;2:284–290.
Ness et al., Nature Biotechnol, 1999;17:893–896.
Patten et al., Curr Opin Biotechnol 1997;8:724–733.
Riggs, in Ausubel, F. M., et al. (eds), Current Protocols in Molecular Biology, Greene Associates/Wiley Interscience, New York, 1992.
Stemmer et al., Biotechniques 1992;14:256 et seq.
Stemmer et al., Nature 1994;370:389–391.
Zhang et al., Proc Natl Acad Sci USA 1997;94:4504–4509.
Zylstra and Gibson, J. Bacteriol. 1989;264:14940–14946.
Joo et al., "Laboratory evolution of peroxide–mediated cytochrome P450 hydroxylation", *Nature*, vol. 399, No. 6737, Jun. 17, 1999, p. 670–673.
Kuchner et al., "Directed evolution of enzyme catalysts", *Trends in Biotechnology*, vol. 15, No. 12, Dec. 1977, p. 523–530.
Oman et al., "Microperoxidase/H–20–2–catalyzed aromatic hydroxylation proceeds by a cytochrome–P–450–type oxygen–transfer reaction mechanism", *European Journal of Biochemistry*, vol. 240, No. 1, 1996, p. 232–23.
Vidakovic et al., "Understanding the role of the essential Asp251in cytachrome P450cam using site–directed mutagenesis, crystallography, and kinetic solvent isotope effect", *Biochemistry*, vol. 37, No. 26.
Faber, K. Biotransformations in Organic Chemistry Springer–Verlad, Berlin, p. 214–217 (1997).
Cook and Atkins *Biochemistry* 36, 10801 (1997).
Short, J., *Nature Biotechnol.* 15, 1322 (1997).
Sheldon, R.A. Catalysis: the key to waste minimization. *J. Chem. Tech. Biotechnol.* 68, 381 (1997).

(Continued)

*Primary Examiner*—Manjunath Rao
(74) *Attorney, Agent, or Firm*—Darby & Darby

(57) ABSTRACT

A method for detecting the presence of an oxygenated compound which is produced when a substrate is reacted with an oxygenase for the substrate. The method involves reacting a coupling enzyme with the oxygenated compound to form a polymeric oxygenated compound which is fluorescent or luminescent. Measurement of the fluorescence or luminescence of the polymeric oxygenated compound provides indirect detection of the oxygenated compound produced by reaction of the oxygenase with the substrate. The method is carried out in a whole cell environment wherein the cell is transformed to express both the oxygen a set being screened and the coupling enzyme. The method can be used to measure the activity of monooxygenases and dioxygenases on aromatic substrates. The method is amenable to large scale screening of enzyme mutants to isolate those with maximum oxygenase activity.

17 Claims, 28 Drawing Sheets

OTHER PUBLICATIONS

Gonzalez, F.J. and Nebert, D.W., Evolution of the P450–gene superfamily–animal plant warfare, molecular drive and human genetic differences in drug oxidation. *Trends Genet.* 6, 182–186 (1990).(1975).
Guengerich, F.P., in Cytochrome P450: Structure, Mechanism, and Biochemistry (Ortiz de Montellano, P.R., E.d.) pp. 473–536, Plenum Press, New York (1995).
England et al. L., *FEBS Lett.* 424, 271 (1998).
Lipscomb et al., *J. Biol. Chem.* 251, 1116 (1976).
Blake II, R. C. and Coon, M. *J. Biol. Chem.*, 255, 4100 (1980).
van Deurzen et al., *Tetrahedron* 53, 13183 (1997).
Nordblom et al., *Arch. Biochem. Biophys.* 175, 524 (1976).
Rahimtula and O'Brien, *Biochem. Biophys. Res. Commun.* 60 440 (1974).
Mueller et al., Twenty–five Years of $P450_{cam}$ Research, in *Cytochrome P450: Structure, Mechanism, and Biochemistry* (2nd ed. Montellano, P. R. O. de), Plenum Press, NY, pp83–124(1995).
Cadwell, R. C. and Joyce, G. F., Randomization of Genes by PCR Mutagenesis, in: *PCR Methods & Applications,* Cold Spring Harbor Laboratory Press, NY, pp28–33 (1992).
PCT Application No. PCT/US98/05956.
D. R. Thatcher, A. Hitchcock, in *Mechanisms of Protein Folding* R. H. Pain, Ed. (IRL Press, Oxford, 1994) pp. 229–261.
C. B. Anfinsen, *Science* 181, 223–230 (1973).
C. H. Schein, *Bio/Technology* 8, 308–317 (1990).
A. Mitraki, J. King, *FEBS Lett.* 307, 20–25 (1992).
J. X. Zhang, D. P. Goldenberg, *Biochemistry* 32, 14075–14080 (1993).
Wetzel et al., *Bio/Technology* 9, 731–737 (1991).
Crameri et al., W. P. C. Stemmer, *Nature Biotechnol.* 14, 315–319 (1996).
S. P. Lei, H. C. Lin, S. S. Wang, J. Callaway, G. Wilcox, *J. Bacteriol.* 169, 4379–4383 (1987).
A. T. Smith, et al., *J. Biol. Chem.* 265, 13335–13343 (1990).
A. M. Egorov, et al., *Ann. N. Y. Acad. Sci.* , 35–40 (1991).
S. A. Ortlepp, D. Pollard–Knight, D. J. Chiswell, *J. Biotechnol.* 11, 353–364 (1989).
F. W. Studier, A. H. Rosenberg, J. J. Dunn, J. W. Dubendorff, *Meth. Enzymol.* 185, 60–89 (1990).
S. Shafikhani, R. A. Siegel, E. Ferrari, V. Schellenberger, *Biotechniques* 23, 304–310 (1997).

K. Sirotkin, *J. Theor. Biol.* 123, 261–279 (1986).
J. S. Shindler, R. E. Childs, W. G. Bardsley, *Eur. J. Biochem.* 65, 325–331 (1976).
J. Carbon, L. Clarke, C. Ilgen, B. Ratzkin, in *Recombinant Molecules: Impact on Science and Society* R. F. J. Beers, E. G. Bassett, Eds. (Raven Press, New York, pp. 355–378 (1977)).
M. Ostermeier, K. Desutter, G. Georgiou, *J. Biol. Chem.* 271, 10616–10622 (1996).
R. Parekh, K. Forrester, D. Wittrup, *Protein Expres. Purif.* 6, 537–545 (1995).
R. D. Gietz, R. H. Schiestl, A. Willems, R. A. Woods, *Yeast* 11, 355–360 (1995).
K. G. Welinder, *Eur. J. Biochem.* 96, 483–502 (1979).
D. B. Goodin, M. G. Davidson, J. A. Roe, A. G. Mauk, and M. Smith, Biochemistry 30, 4953–4962 (1991).
M. M. Fitzgerald, M. J. Churchill, D. E. McRee, and D. B. Goodin, Biochemistry, 33, 3807–3818 (1994).
Miura, Y. and Fulco, A.J. *Biochim. Biophys. Acta* 388, 305 (1975).
Borchardt, J.K., Combinatorial Chemistry: Not just for pharmaceuticals, *Today's Chem. at Work,* Nov. 1998, pp. 36–39.
Setti et al., *Enzyme Microb. Technolo.* 22 656–661 (1998).
G. A. Olah & T. D. Ernst, Oxyfunctionalization of Hydrocarbons. 14. Electrophilic Hydroxylation of Aromatics with Bis(trimethylsilyl)peroxide/Triflic Acid, *J. Org. Chem.* 54: 1204–1206 (1989).
J.T. Groves & Y.–Z. Han, Models and Mechanisms of Cytochrome P450 Action, in Cytochrome P450, 2nd Edition, Ed. P. R. Ortiz de Montellano, Plenum, NY pp3–48.
A. H. Hoveyda, Catalyst discovery through combinatorial chemistry, *Chemistry & Biology* 5:R187–R191 (1998).
Stuart Borman, Combinatorial Catalysts, *Chemical & Engineering News,* Nov. 4, 1996 p. 37–39.
Handelsman, J. et al., Molecular biological access to the chemistry of unknown soil microbes: a new frontier for natural products, *Chem. & Biol.,* 5:R245–249 (1998).
Menage, S. et al., $O_2$ activation and aromatic hydroxylation performed by diiron complexes, *J. Am. Chem. Soc.,* 120, 133370–13382 (1998).
Lonergan et al., *FEMS* 153:485–490 (1997).
Ikeda et al., *Macromolecules* 29:3053–3054 (1996).
White et al., *Ann. Rev. Biochem.* 49:315–56 (1980).

* cited by examiner

FIG. 3A

```
   1 CTGCAGGATC GTTATCGGCT GCCGGATCTG ATCACCCAGC GTTTTTCGAT CGACGAGGCC
  61 AGCAAGGCAC TTGAACTGGT CCCGGGTTCC AAGGCAGGA GCACTGATCA GCACTCCACT
 121 CTTTAGCCAA CCCGGGTTCC AGGAGAACAA CAACAATGAC GACTGAAACC ATACAAAGCA
 181 AGCCCAATCT TGCCCCTCTG CCACCCCATG TCCAGAGCA CCTGGTATTC GACTCGACA
 241 TGTACAATCC GTCGAATCTG TCTCGGGGCG TCCAGGAGGC CTGGCCAGTT CTGCAAGAAT
 301 CAAAGTACC GGATCTGGTG TGGACTGGCT GCAAGGCGG ACACTGGATC GCCACTGGCG
 361 GCCAACTGAT CCGTGAGGCC TATGAAGATT ACCGCCACTT TTCCAGCGAG TGCCGGTTCA
 421 TCCCTGTGA AGCCGGCGAA GCCTACGACT TCATTCCCAC CTGGATGGAT CCGCCCGAGC
 481 ACGCCAGTT TGGTGCCTG GCCAACCAAG TGGTTGGCAT GGGGGTGGTG GATAACTTGG
 541 AGAACCGGAT CCAAGAGCTG GCCTGCTCGC TGATGGAGAG CCTGGCCCG CAAGGACAGT
 601 GCAACTTCAC CGAAGGACTAC GGGAACCCT CATCTTCATG CTGCTCCCAG
 661 GTCTACCCGA AGAAGATATC CCGCACTTGA AATACCTAAC GGATCAGATG ACCGGTCCGG
 721 ATGGCAGCAT GAACTTCCGCA GAGGGCTCTA AGGCTATCTG CGACTATCTG AACGGCCAGG
 781 TGGAGCAACG CAGGCAGAAG CCCGGAACCG AGCCTATCAG CATCGTTGCC CATGGTGTGG
 841 TCAATGGGCG ACCGACATCACC AGTGACGAAG CCAAGAGGAT GTGTGGGCTG TTACTGGTGG
 901 GCGGGCTGGA TACGGTGTTC AATTTCCTCA GCTTCAGCAT GGAGTTCCTG GCCAAAGCC
 961 CGAGGCATCG CCAGGAGGTC ATCGAGGGTC CCGAGGGTAT TCCAGCGCT TGCGAGGAAC
1021 TACTCGGGCG CTTCTCCCTG GTTGCGGATG GCGGGCATGT CACCTCGGAT TACGAGTTTC
1081 ATGGGTGCA ACTGAAGAAA GGTGACCAGA TCCTGCTACC GCAGATGCTG TCTGGCCTGG
1141 ATGAGGGGA AAACGCCTGC CCGATGCAGC TGGACTTCAG TGGCCAAAAG GTTTCACACA
1201 CCACCTTTGG CCAAGCCAGC CATCTGTGCC TTGCCCAGCA CCTGGCCCGC CGGGAAATCA
1261 TGGTCACCCT CAAGGAATGG CTGACCAGGA TTCCTGACTT CTCCATTGCC CGGGTGCCC
1321 AGATTCAGCA CAAGAGCGGC ATGGTCAGCG GCGTGCAGCC ACTCCCTCTG GTCTGGGATC
1381 CGGGGACTAC CAAAGCGGTA TA
```

FIG. 3B

THR THR GLU THR ILE GLN SER ASN ALA ASN LEU ALA PRO
LEU PRO PRO HIS VAL PRO GLU HIS LEU VAL PHE ASP PHE
ASP MET TYR ASN PRO SER ASN LEU SER ALA GLY VAL GLN
GLU ALA TRP ALA VAL LEU GLN GLU SER ASN VAL PRO ASP
LEU VAL TRP THR ARG CYS ASN GLY GLY HIS TRP ILE ALA
THR ARG GLY GLN LEU ILE ARG GLU ALA TYR GLU ASP TYR
ARG HIS PHE SER SER GLU CYS PRO PHE ILE PRO ARG GLU
ALA GLY GLU ALA TYR ASP PHE ILE PRO THR SER MET ASP
PRO PRO GLU GLN ARG GLN PHE ARG ALA LEU ALA ASN GLN
VAL VAL GLY MET PRO VAL VAL ASP LYS LEU GLU ASN ARG
ILE GLN GLU LEU ALA CYS SER LEU ILE GLU SER LEU ARG
PRO GLN GLY GLN CYS ASN PHE THR GLU ASP TYR ALA GLU
PRO PHE PRO ILE ARG ILE PHE MET LEU LEU ALA GLY LEU
PRO GLU GLU ASP ILE PRO HIS LEU LYS TYR LEU THR ASP
GLN MET THR ARG PRO ASP GLY SER MET THR PHE ALA GLU
ALA LYS GLU ALA LEU TYR ASP TYR LEU ILE PRO ILE ILE
GLU GLN ARG ARG GLN LYS PRO GLY THR ASP ALA ILE SER
ILE VAL ALA ASN GLY GLN VAL ASN GLY ARG PRO ILE THR
SER ASP GLU ALA LYS ARG MET CYS GLY LEU LEU LEU VAL
GLY GLY LEU ASP THR VAL VAL ASN PHE LEU SER PHE SER
MET GLU PHE LEU ALA LYS SER PRO GLU HIS ARG GLN GLU
LEU ILE GLU ARG PRO GLU ARG ILE PRO ALA ALA CYS GLU
GLU LEU LEU ARG ARG PHE SER LEU VAL ALA ASP GLY ARG
ILE LEU THR SER ASP TYR GLU PHE HIS GLY VAL GLN LEU
LYS LYS GLY ASP GLN ILE LEU LEU PRO GLN MET LEU SER
GLY LEU ASP GLU ARG GLU ASN ALA CYS PRO MET HIS VAL
ASP PHE SER ARG GLN LYS VAL SER HIS THR THR PHE GLY
HIS GLY SER HIS LEU CYS LEU GLY GLN HIS LEU ALA ARG
ARG GLU ILE ILE VAL THR LEU LYS GLU TRP LEU THR ARG
ILE PRO ASP PHE SER ILE ALA PRO GLY ALA GLN ILE GLN
HIS LYS SER GLY ILE VAL SER GLY VAL GLN ALA LEU PRO
LEU VAL TRP ASP PRO ALA THR THR LYS ALA VAL

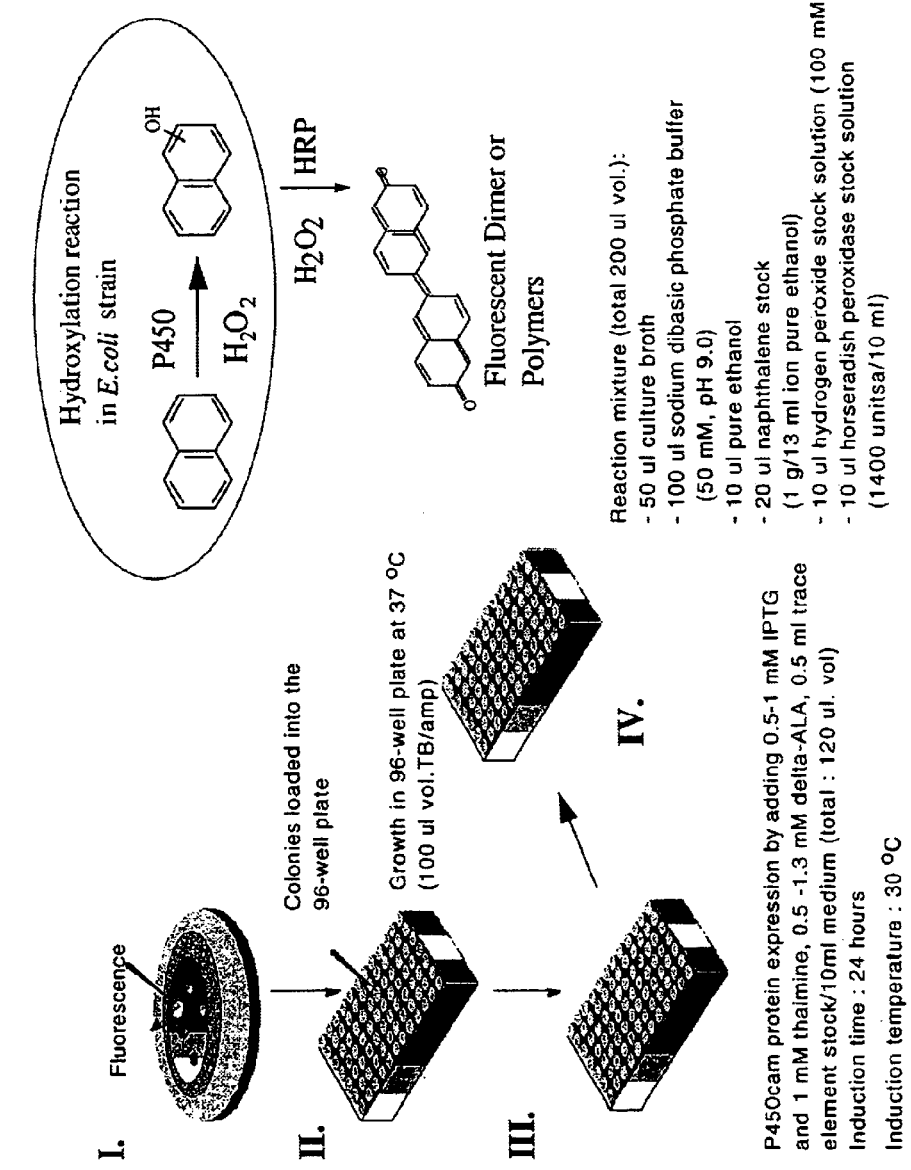

FIG. 5A

|   | 1 | 2 | 3 | 4 | 5 | 6 | 7 | 8 | 9 | 10 | 11 | 12 |
|---|---|---|---|---|---|---|---|---|---|----|----|----|
| A | 2x |   |   | 2x |   |   | 2x |   |   | 2x |   |   |
| B | 2x |   |   | 2x |   |   | 2x |   |   | 2x |   |   |
| C | 2x |   |   | 2x | pCWori + P450cam |   | 2x |   |   | 2x |   |   |
| D | 2x |   |   | 2x |   |   | 2x |   |   | 2x |   |   |
| E | 2x |   |   | 2x |   |   | 2x |   |   | 2x |   |   |
| F | 2x |   |   | 2x | XL-10 E.coli strain |   | 2x |   |   | 2x |   |   |
| G | 2x |   |   | 2x |   |   | 2x |   |   | 2x |   |   |
| H | 2x |   |   | 2x |   |   | 2x |   |   | 2x |   |   |

Columns 1–3: TB + 0.5 mM delta ALA
Columns 4–6: TB + 1.3 mM delta ALA
Columns 7–9: M9 (glucose) + 0.5 mM delta ALA
Columns 10–12: M9 (glycerol) + 0.5 mM delta ALA

* 2x : 200 ul cultivation volume, others : 100 ul cultivation volume

FIG. 12C
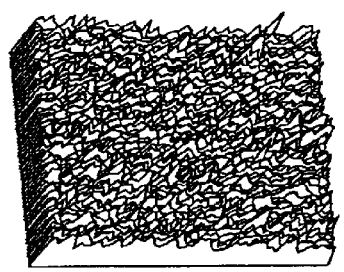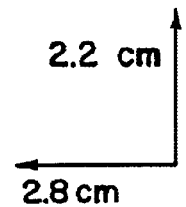
FIG. 12D
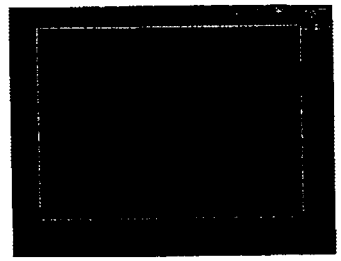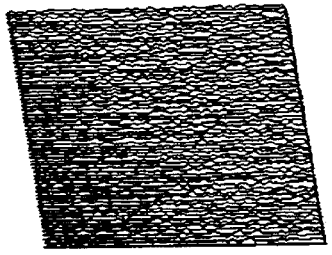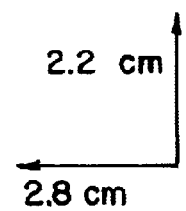
FIG. 12E
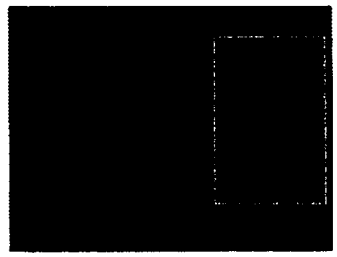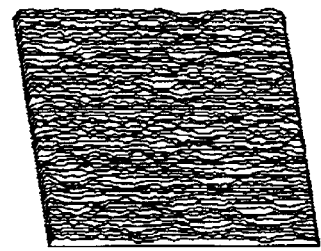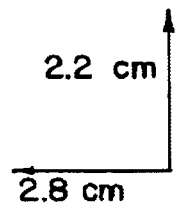
FIG. 12F
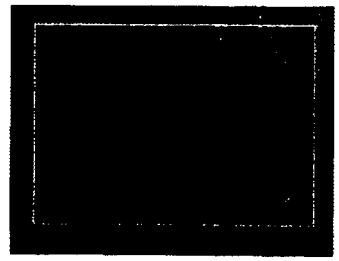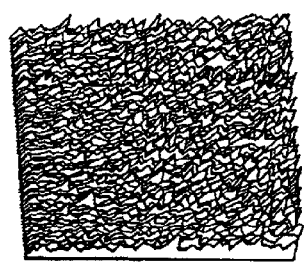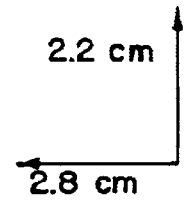

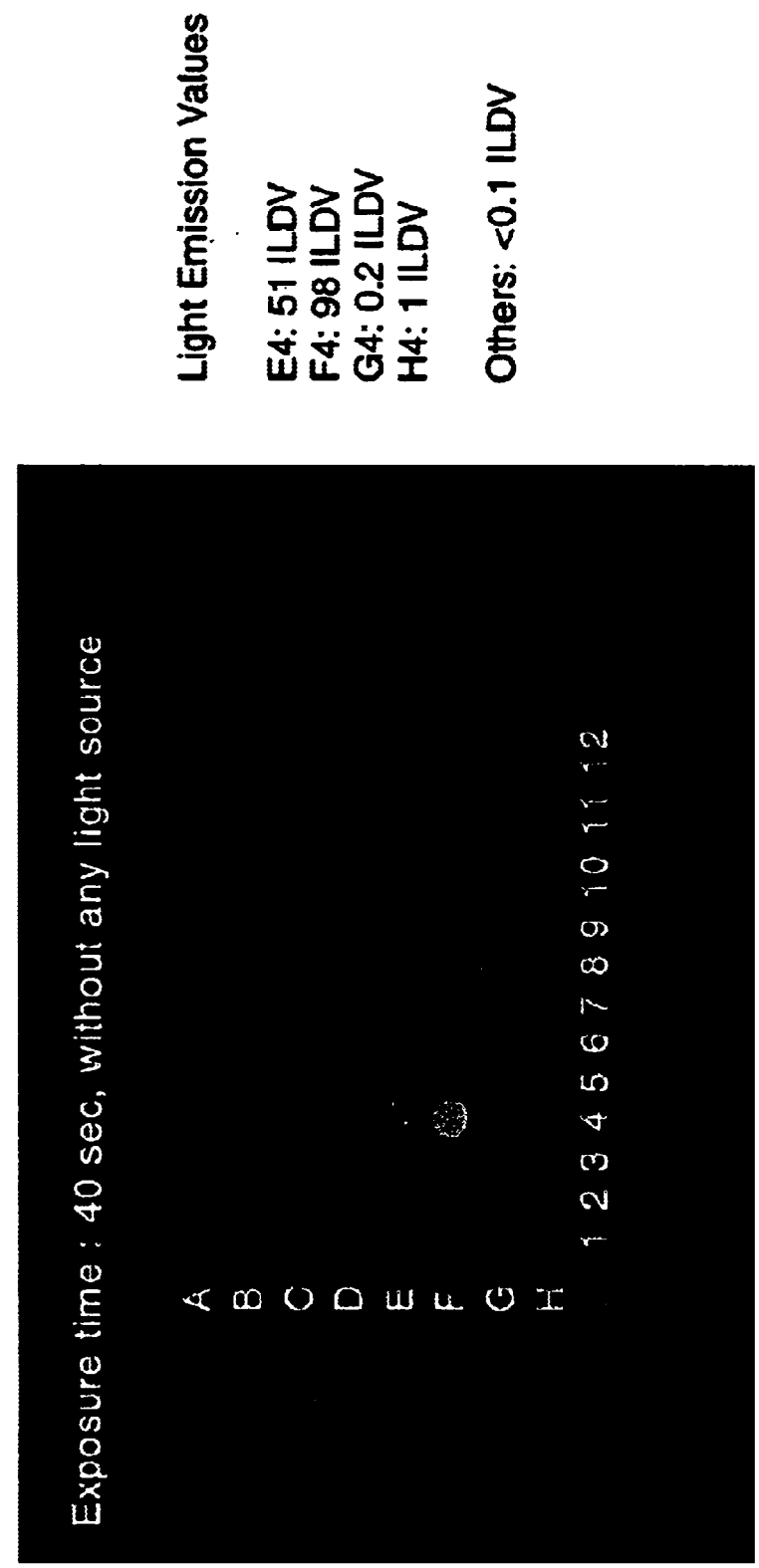

FIG. 22

ATG AAA TAC CTA TTG CCT ACG GCA GCC GCT GGA TTG TTA CTC GCT GCC CAA CCA GCC ATG GCC
Met Lys Tyr Leu Leu Pro Thr Ala Ala Ala Gly Leu Leu Leu Ala Ala Gln Pro Ala Met Ala

FIG. 23A

```
         10        20        30        40        50        60
ATGCAGTTAACCCCTACATTCTACGACAATAGCTGTCCCAACGTGTCCAACATCGTTCGC
 M  Q  L  T  P  T  F  Y  D  N  S  C  P  N  V  S  N  I  V  R 70        80        90       100       110       120
GACACAATCGTCAACGAGCTCAGATCCGATCCCAGATCGCTGCTTCGAATATTACGTCTG
 D  T  I  V  N  E  L  R  S  D  P  R  I  A  A  S  I  L  R  L 130       140       150       160       170       180
CACTTCCATGACTGCTTCGTGAATGGTTGCGACGCTAGCATATTACTGGACAACACCACC
 H  F  H  D  C  F  V  N  G  C  D  A  S  I  L  L  D  N  T  T 190       200       210       220       230       240
AGTTTCCGCACTGAAAAGGATGCATTCGGGAACGCTAACAGCGCCAGGGGCTTTCCAGTG
 S  F  R  T  E  K  D  A  F  G  N  A  N  S  A  R  G  F  P  V

```
       250        260        270        280        290        300
ATCGATGCATGAAGGCTGCCGTTGAGTCAGTCAGCATGCCCACGAACAGTCAGTTGTCAGAC
 I  D  R  M  K  A  A  V  E  S  A  C  P  R  T  V  S  C  A  D 310        320        330        340        350        360
CTGCTGACTATAGCTGCGCAACAGAGTGTGACTCTTGCAGGGGACCGTCCTGGAGAGTG
 L  L  T  I  A  A  Q  Q  S  V  T  L  A  G  G  P  S  W  R  V 370        380        390        400        410        420
CCGCTCGGTCGAGGTGACTCCTACAGGCATTCCTAGACTCGGCCAAGGCCAACTTGCCT
 P  L  G  R  R  D  S  L  Q  A  F  L  D  L  A  N  A  N  L  P 430        440        450        460        470        480
GCTCCATTCTTCACCCTGCCCCAGCTGAAGGATAGCTTTAGAAACGTGGGTCTGAATCGC
 A  P  F  F  T  L  P  Q  L  K  D  S  F  R  N  V  G  L  N  R 490        500        510        520        530        540
TCGAGTGACCTTGTGGCTCTGTCCGGAGGACACACATTTGGAAAGAACCAGTGTAGGTTC
 S  S  D  L  V  A  L  S  G  G  H  T  F  G  K  N  Q  C  R  F
```

FIG. 23C

```
          550        560        570        580        590        600
ATCATGGATAGGCTCTACAATTTCAGCAACACTGGGTTACCTGACCCCAGCGTGAACACT
 I  M  D  R  L  Y  N  F  S  N  T  G  L  P  D  P  T  L  N  T 610        620        630        640        650        660
AGTATCTCCAGACACTGAGAGGCTTGTGCCCACTGAATGCAACCTCAGTGCACTAGTG
 T  Y  L  Q  T  L  R  G  L  C  P  L  N  G  N  L  S  A  L  V 670        680        690        700        710        720
GACTTTGATCTGCGACCCCAACCATCTGATAAGAACTGTTTAGCAGTACTATGTAATCTAGAGGAG
 D  F  D  L  R  T  P  T  I  F  D  N  K  Y  Y  V  N  L  E  E 730        740        750        760        770        780
CAGAAAGGCCTGATACAGAGTGATCAAGAACTGTTTAGCAGTCCAGACGGCCACTGACACC
 Q  K  G  L  I  Q  S  D  Q  E  L  F  S  S  P  D  A  T  D  T 790        800        810        820        830        840
ATCCCACTGGTGAGAAGTTTTGCTAACTCTACTCAAACCTTCTTTAACGCCTTCGTGGAA
 I  P  L  V  R  S  F  A  N  S  T  Q  T  F  F  N  A  F  V  E 850        860        870        880        890        900
GCCATGGACCGTATGGGTAACATTACCCCTCTGACGGGTACCCAAGGCCAGATTGTGTCTG
 A  M  D  R  M  G  N  I  T  P  L  T  G  T  Q  Q  I  R  L 910        920        930
AACTGCAGAGTGGTCAACAGCAACTCT
 N  C  R  V  V  N  S  N  S
```

OXYGENASE ENZYMES AND SCREENING METHOD

This application claims priority under 35 U.S.C. § 119 from U.S. application No. 60/094,403 filed on Jul. 28, 1998; No. 60/106,840 filed on Nov. 3, 1998; No. 60/086,206 filed May 21, 1998; No. 60/106,834 filed on Nov. 3, 1998.

The Government has certain rights to this invention pursuant to Grant No. N0014-96-1-0340, awarded by the United States Navy.

BACKGROUND OF THE INVENTION

1. Field of the Invention

The invention relates to enzymes, called oxygenases, which are biologically active proteins that catalyze certain oxidation reactions involving the addition of oxygen to a substance. The transfer of oxygen from an oxygen-donor compound, such as molecular oxygen ($O_2$) and hydrogen peroxide ($H_2O_2$), to any of millions of useful aromatic or aliphatic substrate compounds is important in organic chemistry and in many biochemical reactions. Typical oxidation reactions include hydroxylation, epoxidation and sulfoxidation, which are widely used in the production of chemicals including pharmaceuticals and other compounds used in medicine. Enzymes which catalyze or improve oxidation reactions are useful in science and industry. The invention relates to novel oxygenase enzymes having improved properties. The invention also relates to methods of screening for oxygenase enzymes, and more particularly, to methods for identifying oxidation enzymes which exhibit catalytic activity with respect to the insertion of oxygen into aromatic or aliphatic compounds.

The screening method involves introducing an organic substrate compound to an oxygen donor compound in the presence of a test enzyme. Exemplary oxygen donors include molecular oxygen or dioxygen ($O_2$) and peroxides such as hydrogen peroxide ($H_2O_2$) and t-butyl peroxide. Exemplary substrates include naphthalene, 3-phenylpropionate, benzene, toluene, benzoic acid, and anthracene. An oxygenated product is formed when the test enzyme has oxidation activity, particularly oxygenase activity, under test conditions.

A coupling enzyme is used to bring together molecules of the oxygenated product into larger molecules or polymers which absorb UV light, produce a color change, or are fluorescent or luminescent. Exemplary coupling enzymes include peroxidases from various microbial and plant sources, such as horseradish peroxidase (HRP), cytochrome c peroxidase, tulip peroxidase, lignin peroxidase, carrot peroxidase, peanut peroxidase, soybean peroxidase, peroxidase Novozyme® 502, as well as laccases such as fungal laccase. The presence and degree of a change in absorbance, color, fluorescence or luminescence can be detected or measured, and indicates the presence of oxygenated product. Detection can be enhanced by a chemiluminescent agent, such as luminol. These techniques provide a reliable indication of oxygenase activity, that is, the production of oxygenated compound by reaction of the oxygen donor with the substrate in the presence of (and mediated by) the enzyme.

The method is preferably carried out in a whole cell environment. A host cell is transformed, using genetic engineering techniques, to express an oxygenase being screened, and may also be engineered to express a coupling enzyme. The method is amenable to large scale screening of enzyme mutants to isolate those with desirable oxygenase activity, for example maximum activity under certain conditions or towards a particular substrate compound. The method is also amenable to screening gene libraries isolated from nature (50).

Oxygenase enzymes typically use molecular oxygen, in the presence of cofactors, coenzymes, and/or ancillary proteins, to add oxygen to a substrate. Oxygen is a highly reactive chemical element. In pure molecular form, it is a gas that is a principal component of air, and is stable as a combination of two oxygen atoms ($O_2$). It appears in water ($H_2O$), in rocks and minerals, in many organic compounds, and is active in many biochemical and physiological processes. Some $O_2$-utilizing enzymes can use other oxygen donors, e.g. peroxides (according to a reaction scheme called the peroxide shunt pathway), but do so poorly, with low activity and a low yield of oxygenated product. Moreover, certain coenzymes, cofactors or ancillary proteins may still be required, although the peroxide shunt does not require the difficult coenzymes, e.g. NAD(P)H, associated with pathways using $O_2$ as a substrate.

The improved oxygenase enzymes of the invention are capable of efficiently catalyzing reactions wherein oxygen is added to a substrate, using oxygen donors other than molecular oxygen, and without requiring certain cofactors, coenzymes, or ancillary redox proteins. These new enzymes have significantly more activity than native enzymes. For example, they are at least twice as active, and typically are ten or more times as active as a wild-type enzyme towards a particular substrate or under particular reaction conditions.

2. Description of Related Art

The publications and reference materials noted here and in the appended Bibliography are each incorporated by reference in their entirety. They are referenced numerically in the text and the Bibliography below.

Catalysts, Enzymes and Oxygenases.

An enzyme is a biological catalyst, typically a protein, which promotes a biochemical reaction. A catalyst enables a chemical reaction to proceed at a faster rate or under different conditions than would otherwise occur. Usually, a catalyst is itself unchanged at the end of the reaction, although oxidative enzymes may be deactivated slowly during these reactions. Oxygenase enzymes that are capable of catalyzing the insertion of oxygen into aromatic (ring-containing) and aliphatic (open-chain) chemical compounds, and other chemical compounds or substrates have many potential applications in pharmaceuticals manufacturing, in the production of chemicals, and also in medicine. Dioxygenases introduce two atoms of oxygen, e.g. both oxygens from a donor such as molecular oxygen ($O_2$). Monooxygenases, also called mixed function oxygenases, add one atom of oxygen to a substrate compound. In these reactions a second oxygen from the oxygen donor may be combined with hydrogen ($H^+$) in a companion reaction, called a reduction reaction, to form water ($H_2O$). Compounds other than molecular oxygen, such as peroxides, can also donate oxygen to a substrate in the presence of various oxygenases.

Common monooxygenation reactions include hydroxylation and epoxidation. In a hydroxylation reaction, oxygen is introduced to a substrate as a hydroxyl group (OH). In an epoxidation reaction, oxygen is introduced as a bridge across two other atoms, typically in place of a double bond between two carbon atoms. This can form an activated or reactive group having a three-member ring of one oxygen atom and two carbon atoms. A common dioxygenation reaction is sulfoxidation. In a sulfoxidation reaction, two oxygen atoms are added to a sulfur atom that is bonded to two other atoms, typically two carbon atoms, each of which is part of a hydrocarbon chain.

The introduction of oxygen to a compound may change its biochemical activity or functionality, and may activate the compound so that it can participate in further chemical reactions. Oxygenated substrates may be used by organisms or industrially, in the synthesis of useful compounds from starting materials or intermediates. Oxygenation may also be useful in the breakdown of compounds, to provide starting materials and intermediates for other reactions. For example, bacteria use oxygenases to digest aromatic compounds.

Problems Addressed by the Invention.

Among the problems addressed by the invention are the significant disadvantages of many known enzyme systems. These problems have prevented commercial use and exploitation of such systems. Many oxygenases, like other enzymes, require expensive coenzymes (e.g. NADPH) and ancillary proteins (e.g. a reductase enzyme), and often must be used in whole cells or reactors with recycled coenzymes, to keep the coenzyme costs low. Known enzymes also are relatively inefficient or unstable under industrial conditions, and may be undesirably deactivated by reaction products or byproducts, or for other reasons. These types of enzyme systems, particularly when used in whole cell reactions, are also prone to competing reactions which can lower the selectivity and yield.

Thus, enzymes which do not require coenzymes, use less coenzymes, or use less expensive coenzymes are desirable. Enzymes which are more efficient, more stable, or which function under different conditions are also desirable. It would also be desirable to provide enzymes which are not adversely affected by competing reactions. Enzymes which promote oxidation of different substrates, which insert oxygen at different positions on a given substrate, insert oxygen more efficiently, or use different oxygen donor compounds would also be desirable, as would enzymes which are more or less specific than known enzymes in catalyzing certain reactions. For example, hydrogen peroxide or other peroxides are good choices of oxidant for fine chemicals manufacturing, as their use would require less specialized equipment, and less cost overall, than molecular oxygen due to the greatly simplified catalyst system. A suitable screening method for oxygenases is also desirable, and would provide an important tool in the discovery and identification of new and improved oxidation enzymes.

Enzymatic oxygenation reactions are particularly intriguing, because directed oxyfunctionalization of unactivated organic substrates remains a largely unresolved challenge to synthetic chemistry. This is especially true for regiospecific reactions, where oxygenation at a specific position of a substrate occurs in only one of two or more possible ways. For example, regiospecific hydroxylation of aromatic compounds by purely chemical methods is notoriously difficult. Reagents for ortho or o-hydroxylation of ring compounds, at positions on the ring which are next or adjacent to each other, are described in the literature. Reagents are also available for para or p-hydroxylation, at positions on the ring which are opposite each other. However, some of these reagents are explosive, and undesirable by-products are usually obtained (1). Likewise, specific oxygenation of enantiomers (mirror-image forms of a compound), is difficult and not well understood. In these reactions, one enantiomer is preferentially oxygenated, but the mirror-image enantiomer of the same compound is poorly oxygenated, or is not oxygenated at all. Similarly, it is difficult to oxygenate a substrate with high enantiospecificty, i.e. so as to create one particular enantiomeric form versus another. Thus, oxygenation to form a particular enantiomer is difficult. Consequently, oxidation enzymes which facilitate particular regiospecific or enantiospecific reactions would be desirable, particularly enzymes which do so under laboratory or industrial conditions, or which do so more efficiently or in some better way.

Oxidation Enzymes.

Various native mono- and dioxygenase enzymes from different microbial, human, plant, and animal sources are known. These include enzymes such as chloroperoxidase (CPO), large numbers of cytochrome P450 enzymes (P450), methane monooxygenases (MMO), toluene monooxygenases, toluene dioxygenases (TDO), biphenyl dioxygenases and naphthalene dioxygenases (NDO). These enzymes have demonstrated the ability to catalyze hydroxylation and many other interesting and useful oxidation reactions. However, they are generally unsuitable for industry due to their inherent complexity, low stability and low productivity under industrial conditions (e.g. in the presence of organic solvents, high concentrations of reactants, etc.).

One class of known oxidation enzymes is the cytochrome P450 enzymes. These heme proteins have iron-containing heme groups and are important monooxygenase enzymes involved in, among other reactions, detoxification of foreign or toxic materials (xenobiotics), drug metabolism, carcinogenesis, and steroid biosynthesis (5 and 6). One exemplary P450 enzyme, P450$_{cam}$ from *Pseudomonas putida*, whose natural substrate is camphor, is also capable of regiospecific hydroxylation of a variety of substrates including, at a low level of activity, naphthalene ($C_{10}H_8$) a bicyclic aromatic compound (7). However, the catalytic turnover of this enzyme requires the reduced form of nicotinamide-adenine dinucleotide (NADH) as a coenzyme and two ancillary proteins. One of these proteins is putidaredoxin, an iron-sulfur protein (also called a ferredoxin) that acts as an electron carrier to shuttle electrons from NADH. The other ancillary protein is the enzyme putidaredoxin reductase, a flavoprotein which catalyzes the transfer of hydrogen atoms from one substrate to another (8). This requirement for two redox proteins and NADH makes P450$_{cam}$ and other P450 catalysis highly expensive and difficult to use in laboratory and industrial applications. It would be desirable to provide a simpler and more economical P450-type catalyst and hydroxylation system, in particular a system which requires fewer ancillary proteins or coenzymes, or which does not require them at all.

P450 enzymes typically use dioxygen ($O_2$) as the oxygen donor for hydroxylation, adding one oxygen to a substrate compound, such as naphthalene, and forming water with hydrogen and another oxygen as a byproduct. They are most efficient when using dioxygen with expensive coenzymes, such as the reduced forms of nicotinamide-adenine dinucleotide (NADH) or nicotinamide-adenine dinucleotide phosphate (NADPH), collectively "NAD(P)H". Ancillary proteins may also be needed for efficient enzyme activity. However, various P450s (and, possibly, some MMOs) are able to catalyze the hydroxylation of an organic substrate using a peroxide, such as hydrogen peroxide or alkyl peroxides, via the so-called peroxide shunt pathway (9). Peroxides are compounds, other than molecular $O_2$, in which oxygen atoms are joined to each other. Other oxygen donors include peroxyacids, $NaIO_4$, $NaClO_2$, and iodosyl benzene.

Nordblom et al. (11) studied hydroperoxide-dependent substrate hydroxylation by liver microsomal P450 in hepatic microsomes. A variety of substrates were shown to be attacked by the enzyme in the presence of cumene hydroperoxide. Using benzphetamine as the substrate, it was also shown that other peroxides, including hydrogen peroxide, peracids and sodium chlorite, could be used in place of oxygen (11). Rahimtula et al. (12) showed that cumene hydroperoxide is capable of supporting the hydroxylation of various aromatic compounds (biphenyl, benzpyrene, coumarin, aniline) by cytochrome P450 in hepatic microsomes. Unfortunately, native cytochrome P450 is rapidly deactivated by peroxides and other oxidants.

The enzyme chloroperoxidase (CPO) from *Caldariomyces fumago* has an active site whose structure is similar to cytochrome P450 enzymes. CPO will catalyze various oxidation reactions, including enantioselective hydroxylation, epoxidation and sulfoxidation, using peroxides. This enzyme utilizes peroxide efficiently but cannot utilize molecular oxygen because it does not have the coenzyme machinery of the P450 enzymes. CPO also provides an example of an enzyme that is deactivated by reactive intermediates. Heme alkylation by the epoxide product in the CPO-catalyzed epoxidation of 1-alkenes results in CPO deactivation.

Heme oxygenases such as P450s and heme peroxidases, which are peroxidase enzymes that contain the heme prosthetic group, are generally prone to deactivation via oxidation of the porphyrin ring in the heme substrate, by reaction with so-called suicide inhibitors formed during catalysis, and also by formation of Compound III (for peroxidases). Compound III is an intermediate enzyme-substrate-oxygen-iron complex, sometimes referred to an oxyperoxidase. For example, the enzyme horseradish peroxidase (HRP) is deactivated during the oxidation of phenol compounds, e.g. six-member hydrocarbon ring structures containing one or more hydroxyl (OH) groups. In theory, this may be due to the formation of phenoxy radicals which react with oxygen to form a reactive peroxy-radical species. Compound III forms in the presence of excess hydrogen peroxide and is not involved in the reaction cycle. However, its accumulation reduces the amount of active enzyme. Compound III stability in turn depends on the specific enzyme.

The rates of all of these deactivation pathways depend on the protein framework, i.e. the particular proteins, structures and conditions involved. They all are therefore amenable to improvement by mutations. This includes oxygenases that are more suitable to function in the presence of high concentrations of hydrogen:peroxide, or other peroxides or oxygen-donating agents. Improved oxygenases also include those which are more resistant to deactivation, do not require coenzymes or use them more efficiently, function under different conditions or with different specificities, or which hydroxylate different substrates or a variety of substrates, or which do so more efficiently. As one example, it would be desirable to make modified P450 enzymes that are functionally similar or equivalent to CPO, or which share desirable features of CPO. An improved P450 enzyme of this kind, for example, would have the ability to oxygenate a substrate or substrates using a peroxide, e.g. hydrogen peroxide, without expensive coenzymes, and with a high efficiency and improved resistance to deactivation.

Enzyme Modification.

The observed constraints on the use of native enzymes are thought to be a consequence of evolution. Enzymes have evolved in the context and environment of a living organism, to carry out specific biological functions under conditions conducive to life—not laboratory or industrial conditions. In some cases, evolution may favor or even require less than optimally efficient enzymes. For example, detoxication enzymes, such as cytochrome P450 enzymes, function to help convert foreign (xenobiotic) chemical compounds into other compounds that an organism can use, that are not toxic, or that are present in non-toxic amounts. In order to deal with environmental conditions or foreign compounds an organism has not encountered before, detoxification enzymes may attack a relatively large number of substrates, and may accidentally produce products that are as or more toxic than the substrate. Thus, maximizing the flow of potentially harmful foreign substrates for processing, e.g. using an overly efficient catalyst, may not be the best evolutionary strategy. This is particularly true when there is a time-dependent xenobiotic profile, meaning that the organism can only safely handle so much foreign material at a time (2). In this situation, a less than maximally active enzyme that is appropriately balanced to the particular needs of the organism and its environment would be a better evolutionary goal. In a laboratory or industrial setting, it is desirable to provide enzymes which are more active, and process more substrate more rapidly.

Thus, the output, efficiency, working conditions, stability and other properties of known enzymes are not thought to be unalterable, nor are they limitations which are seen as intrinsic to the nature of these catalysts as proteins. It is possible that these native catalysts can be evolved in vitro, or that analogous catalysts can be otherwise developed, to alter or enhance the enzyme's properties, for example to obtain much more efficient laboratory or industrial oxidative catalysts. Enzyme selectivity and substrate specificity may also be altered to better match the needs of the synthetic chemist. Improved catalysts can also be obtained by screening cultures of native organisms or expressed gene libraries (3).

One technique which may be applied to the discovery of improved catalytic enzymes is directed evolution. Directed evolution is a procedure by which the evolutionary process is accelerated in vitro to produce mutant enzymes which have certain desired characteristics. An example of the use of directed evolution for identifying and isolating improved para-nitrobenzyl esterases is set forth in U.S. Pat. No. 5,741,691. See also, U.S. Pat. No. 5,811,238 (13). Other techniques, such as random mutagenesis, may also be used to obtain new enzymes. Improved enzymes may also be discovered in nature.

According to a preferred embodiment of the invention, directed evolution or random mutagenesis can be used to produce an array of efficient catalysts which can perform oxidations using agents other than dioxygen ($O_2$) as the oxidant. For example, peroxides such as hydrogen peroxide ($H_2O_2$) may be used. Directed evolution can also be used to alter the properties of oxidative enzymes that use molecular oxygen. A variety of such enzymes, including cytochrome P450s, other monooxygenases, and dioxygenases such as toluene dioxygenase, facilitate useful oxygenation reactions. It is desirable to alter the reactivities, selectivities and stabilities of these enzymes to produce improved enzymes. An important tool for finding improved oxidation biocatalysts in nature, by directed evolution, by random mutagenesis, or by other means, is a sensitive, accurate and rapid screening method. Accordingly, there is a need to develop new and improved screening methods for enzymes which function as oxygenases. In particular there is a need for screening methods which are well-suited for use in connection with directed evolution procedures.

SUMMARY OF THE INVENTION

In accordance with the invention, a method of screening for oxidation enzymes or oxygenases is provided. New and improved oxidation enzymes are also provided.

More particularly, the presence of oxygenated compounds which are produced by the action of an oxygenase on a particular substrate is detected. The invention is particularly well suited for screening large numbers of both naturally occurring and mutated oxygenases to determine their activity with respect to a wide range of substrates, including aromatic and aliphatic compounds. It was discovered that the detection of oxygenated compounds produced by action of an oxygenase can be improved by reacting the oxygenated compound with a coupling enzyme to form a polymeric oxygenated compound which absorbs UV light, produces a color change, or is luminescent, i.e. phosphorescent or preferably fluorescent. The presence and amount of oxygenated compounds in a sample can be indicated by detecting, observing or measuring the presence, and if desired the degree, of light absorption, color change, fluorescence, or luminescence. It was also discovered that the luminescence and detection of the polymeric oxygenated compound can be further enhanced by creating the polymeric oxygenated compound in the presence of a chemiluminescent agent, such as luminol, to increase chemiluminesence intensity and/or lifetime. Other agents can also be used to enhance color development or color change reactions (44).

The invention is particularly well suited for whole cell screening procedures wherein a host cell, such as the E. coli bacteria, is transformed with a suitable vector to express an oxygenase to be screened. The transformed cell is treated with a substrate, such as naphthalene, for a sufficient time to allow an oxygenated compound, e.g., hydroxylated naphthalene, to be formed. A coupling enzyme, such as horseradish peroxidase (HRP), is provided and allowed to react with the oxygenated compound, to form a polymeric oxygenated compound which exhibits increased levels of UV light absorption, luminescence, or fluorescence in the case of polymeric hydroxylated naphthalene. The fluorescence generated by the polymeric oxygenated compound is measured by known means to provide indirect detection of the activity of the oxygenase, e.g., the amount of oxygenated compound produced by reaction of the oxygenase with the substrate. The coupling enzyme can be produced extraneously and added to the cell culture, or in a preferred embodiment, it can be produced intracellularly, that is, by or inside the same cell that is producing the oxygenase.

Thus, a whole cell screening system is provided wherein a suitable host cell is transformed with suitable vectors to provide co-expression by the transformed cell of both an oxygenase and a coupling enzyme. As a result, infusion of the substrate into the cell results in contemporaneous generation of oxygenated compounds due to action of the oxygenase on the substrate and the formation of polymeric oxygenated compounds resulting from action of the coupling enzyme on the oxygenated compounds. When desired, one or more cofactors, coenzymes or ancillary proteins can be used to improve the activity of the oxidation enzyme or enhance the oxygenation reaction.

The invention is particularly well suited for screening a large number of naturally occurring or mutated oxygenases to determine relative enzyme activities with respect to a substrate, and in particular to establish which enzymes exhibit the highest activity with respect to a given substrate or which insert oxygen at a different site on the substrate (show different regiospecificity). The invention is applicable to both monooxygenases or dioxygenases and can be used to detect oxygenated compounds formed by hydroxylation or epoxidation. The invention may also be applicable to sulfoxidation reactions. Hydroxylation enzymes are preferred.

The invention is also suitable for screening libraries of oxygenase catalysts that are not enzymes, for example, compounds generated by combinatorial chemistry (43, 48, 49). The addition of oxygen by such catalysts can be assayed by addition of a coupling enzyme under conditions suitable for the coupling reaction. For example, conditions can be modified after the oxygenation reaction to accommodate the coupling reaction. However, it may not be necessary to significantly modify the reaction conditions for some coupling enzymes. As one example, horseradish peroxidase is known to function over a wide range of conditions and in aqueous media and in a wide variety of nonpolar organic solvents.

The above features and many other attendant advantages of the invention will become better understood by reference to the following detailed description when taken in conjunction with the accompanying drawings.

BRIEF DESCRIPTION OF THE DRAWINGS

FIG. 3A shows a nucleotide coding sequence for wild type cytochrome $P450_{cam}$ monooxygenase [SEQ. ID. NO. 1]. FIG. 3B shows an amino acid sequence for wild type cytochrome $P450_{cam}$ monooxygenase [SEQ. ID. NO. 2].

FIG. 4A is a pictorial representation of an exemplary 96 well plate assay in accordance with the invention. FIG. 4B is a diagrammatic representation of a reaction scheme according to the invention.

FIG. 5A is a tabular representation of the wells in a 96-well plate in which different media and components were used to evaluate the effect on the $P450_{cam}$ activity of transformed E. coli host cells.

FIGS. 12A-12F show the image analysis results, in graphic form, of the fluorescence shown by colonies of *E. coli* host cells (control), and the same host cells transformed to express P450 enzyme, HRP enzyme, or both, and under different assay conditions (with and without substrate and oxygen donor).

FIG. 22 shows the coding sequence of the pelB signal peptide ([SEQ. ID. NO. 14 and 15]).

FIG. 23 shows a nucleotide and amino acid sequence encoding an HRP enzyme variant designated HRP1A6 ([SEQ. ID. NO. 16 and SEQ. ID. NO. 17]).

DETAILED DESCRIPTION OF THE INVENTION

Figure 1:
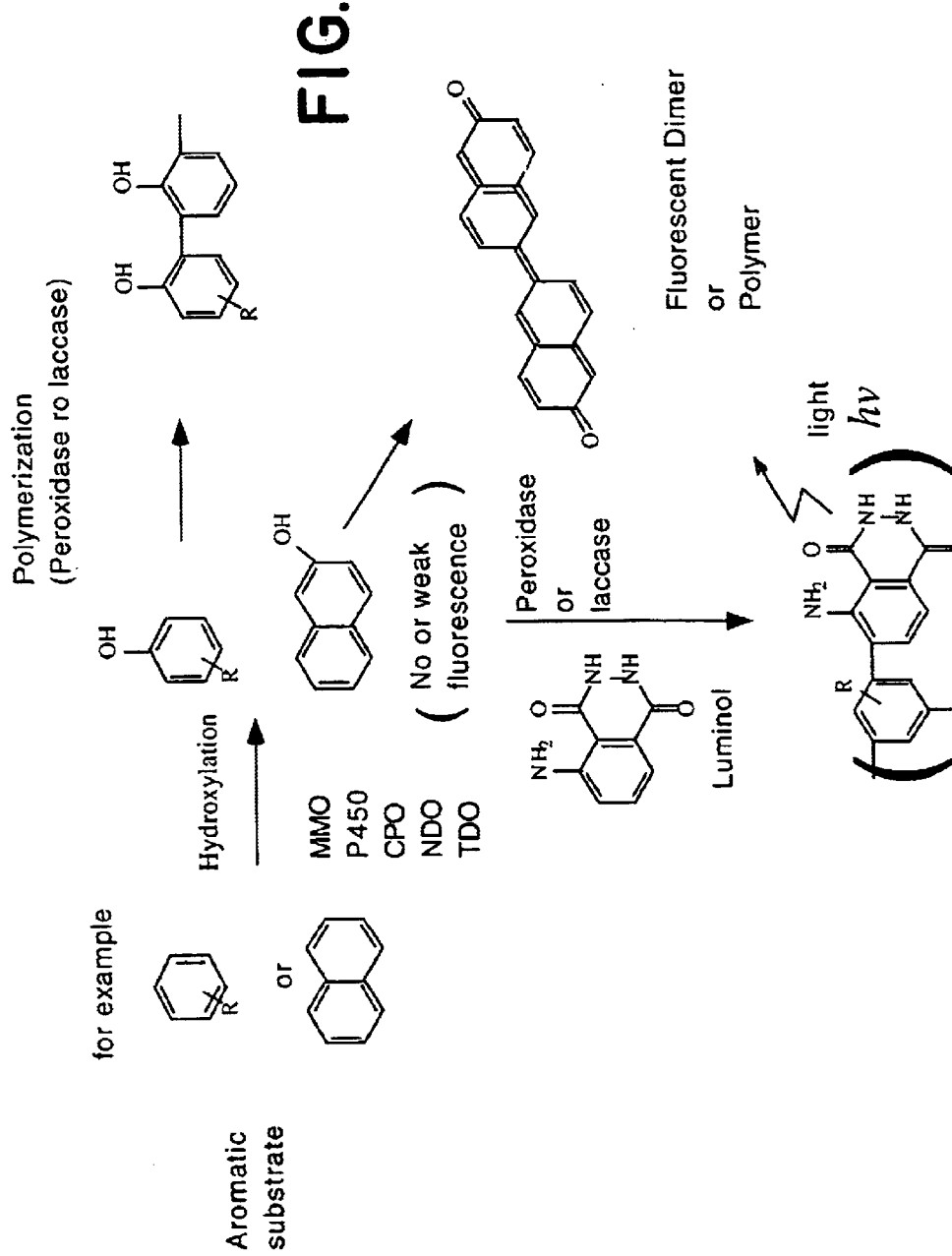
FIG. 1 is a schematic representation of a reaction pathway of an exemplary embodiment of the invention.

The invention concerns oxidation enzymes and a general method for screening enzymes that are capable of oxygenating various substrates. In particular, the invention is especially well suited for evaluating the activity of enzymes that are capable of oxygenating aromatic substrates.

Definitions.

The term "substrate" means any substance or compound that is converted or meant to be converted into another compound by the action of an enzyme catalyst. The term includes aromatic and aliphatic compounds, and includes not only a single compound, but also combinations of compounds, such as solutions, mixtures and other materials which contain at least one substrate. Aromatic substrates are preferred. Exemplary and non-limiting aromatic substrates of the invention include naphthalene, 3-phenylpropionate (3-PPA), coumarin, benzene, toluene, and benzoic acid. Preferred substrates, particularly in connection with the screening methods of the invention, are naphthalene and 3-phenylpropionate.

An "oxidation reaction" or "oxygenation reaction", as used herein, is a chemical or biochemical reaction involving the addition of oxygen to a substrate, to form an oxygenated or oxidized substrate or product. An oxidation reaction is typically accompanied by a reduction reaction (hence the term "redox" reaction, for oxidation and reduction). A compound is "oxidized" when it receives oxygen or loses electrons. A compound is "reduced" (it loses oxygen or gains electrons). According to the invention, oxidation reactions are preferably oxygenation reactions which add oxygen to a substrate. Oxygen typically donates electrons in ionic form as $OH^-$ or $O_2^{2-}$. Conceptually, electrons (negatively charged subatomic particles) may also be lost or gained via the transfer of protons (positively charged subatomic particles), for example as hydrogen ions ($H^+$ of $H_2^{2+}$). An "ion" is an atom or molecule with a net positive or negative charge, i.e. it has excess electrons (a negative charge) or is missing electrons (a positive charge). Thus, oxidation reactions can also be called "electron transfer reactions" and encompass the loss or gain of electrons (e.g. oxygen) or protons (e.g. hydrogen) from a substance. Preferred oxidized compounds of the invention are those which are "oxygenated", meaning they have received oxygen.

The term "enzyme" means any substance composed wholly or largely of protein that catalyzes or promotes, more or less specifically, one or more chemical or biochemical reactions. A protein is a polypeptide (one or more peptides), meaning that it is a chain of chemical building blocks called amino acids that are linked together by chemical bonds called peptide bonds. A protein, including enzymes, may be "native" or "wild-type", meaning that it occurs in nature; or it may be a "mutant", "variant" or "modified", meaning that it has been made, altered, derived, or is in some way different or changed from a native protein. A "test enzyme"

is a protein-containing substance that is tested to determine whether it has properties of an enzyme. The term "enzyme" can also refer to a catalytic polynucleotide (e.g. RNA or DNA).

The "activity" of an enzyme is a measure of its ability to catalyze a reaction, and may be expressed as the rate at which the product of the reaction is produced. For example, enzyme activity can be represented as the amount of product produced per unit of time, per unit (e.g. concentration or weight) of enzyme. The "stability" of an enzyme means its ability to function, over time, in a particular environment or under particular conditions. One way to evaluate stability is to assess its ability to resist a loss of activity over time, under given conditions. Enzyme stability can also be evaluated in other ways, for example, by determining the relative degree to which the enzyme is in a folded or unfolded state. Thus, one enzyme is more stable than another, or has improved stability, when it is more resistant than the other enzyme to a loss of activity under the same conditions, is more resistant to unfolding, or is more durable by any suitable measure.

An "oxidation enzyme" is an enzyme that catalyzes one or more oxidation reactions, typically by adding, inserting, contributing or transferring oxygen from a source or donor to a substrate. Such enzymes are also called oxidoreductases or redox enzymes, and encompasses oxygenases, hydrogenases or reductases, oxidases and peroxidases. An "oxygenase" is an oxidation enzyme that catalyzes the addition of oxygen to a substrate compound. A "dioxygenase", is an oxygenase enzyme that adds two atoms of oxygen to a substrate. A "monooxygenase" adds one atom of oxygen to a substrate. An "oxidase" is an oxidation enzyme that catalyzes a reaction in which molecular oxygen (dioxygen or $O_2$) is reduced, for example by donating electrons to (or receiving protons from) hydrogen.

Preferred oxidation enzymes of the invention include, without limitation, oxygenases (dioxygenases and monooxygenases), including hydroxylases, epoxidases, and sulfoxidases, which catalyze, respectively, hydroxylation, epoxidation, and sulfoxidation reactions. Of these, monooxygenases, hydroxylases, and dioxygenases are preferred. Exemplary oxidation enzymes include, without limitation, native or modified chloroperoxidase (CPO), cytochrome P450s, methane monooxygenases (MMOs), toluene monooxygenase, toluene dioxygenases (TDO), naphthalene dioxygenases (NDO), and biphenyl dioxygenases. A preferred oxidation enzyme is native or modified cytochrome P450.

The terms "oxygen donor", "oxidizing agent" and "oxidant" mean a substance, molecule or compound which donates oxygen to a substrate in an oxidation reaction. Typically, the oxygen donor is reduced (accepts electrons). Exemplary oxygen donors, which are not limiting, include molecular oxygen or dioxygen ($O_2$) and peroxides, including alkyl peroxides such as t-butyl peroxide, and most preferably hydrogen peroxide ($H_2O_2$). A peroxide is any compound having two oxygen atoms bound to each other.

The term "coupling enzyme" means an enzyme which catalyzes a chemical or biochemical reaction in which an oxygenated substrate or product reacts to forms a detectable complex, aggregate, polymer, other reaction product. A preferred coupling enzyme catalyzes the formation of a reaction product that has a detectable or enhanced color change, TV absorbance or luminescence (e.g. fluorescence). For example, a suitable coupling enzyme catalyzes the formation of a fluorescent polymer by joining two or more oxygenated substrate molecules to each other. According to one embodiment of the invention, the fluorescence of the polymerized oxygenated compound is more readily detectable than the fluorescence, if any, of oxygenated substrate which has not been polymerized. A coupling enzyme may or may not be an oxidation enzyme, provided it functions to catalyze the formation of a detectable oxygenated reaction product. Exemplary coupling enzymes include, without limitation, peroxidases from various microbial and plant sources, such as horseradish peroxidase (HRP), cytochrome c peroxidase, tulip peroxidase, lignin peroxidase, carrot peroxidase, peanut peroxidase, soybean peroxidase, peroxidase Novozyme® 502, as well as laccases such as fungal laccase. HRP and laccase are preferred coupling enzymes.

As used herein, a "luminescent" substance means any substance which produces detectable electromagnetic radiation, or a change in electromagnetic radiation, most notably visible light, by any mechanism, including color change, UV absorbance, fluorescence and phosphorescence. Preferably, a luminescent substance according to the invention produces a detectable color, fluorescence or UV absorbance.

The term "chemiluminescent agent" means any substance which enhances the detectability of a luminescent (e.g. fluorescent) signal, for example by increasing the strength or lifetime of the signal. One exemplary and preferred chemiluminescent agent is 5-amino-2,3-dihydro-1,4-phthalazinedione (luminol) and analogs. Other chemiluminescent agents include 1,2-dioxetanes such as tetramethyl-1,2-dioxetane(TMD),1,2-dioxetanones, and 1,2-dioxetanediones.

The term "polymer" means any substance or compound that is composed of two or more building blocks ('mers') that are repetitively linked to each other. For example, a "dimer" is a compound in which two building blocks have been joined together.

The term "cofactor" means any non-protein substance that is necessary or beneficial to the activity of an enzyme. A "coenzyme" means a cofactor that interacts directly with and serves to promote a reaction catalyzed by an enzyme. Many coenzymes serve as carriers. For example, $NAD^+$ and $NADP^+$ carry hydrogen atoms from one enzyme to another. An "ancillary protein" means any protein substance that is necessary or beneficial to the activity of an enzyme.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

Proteins and enzymes are made in the host cell using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids which form the protein or enzyme. An "amino acid sequence" is any chain of two or more amino acids. Each amino acid is represented in DNA or RNA by one or more triplets of nucleotides. Each triplet forms a codon, corresponding to an amino acid. For example, the amino acid lysine (Lys) can be coded by the nucleotide triplet or codon AAA or by the codon AAG. (The genetic code has some redundancy, also called degeneracy, meaning that most amino acids have more than one corresponding codon.) Because the nucleotides in DNA and RNA sequences are read in groups of three for protein production, it is important to begin reading the sequence at the correct amino acid, so that the correct triplets are read. The way that a nucleotide sequence is grouped into codons is called the "reading frame."

A "coding sequence" or a sequence "encoding" a polypeptide, protein or enzyme is a nucleotide sequence that, when expressed, results in the production of that polypeptide, protein or enzyme, i.e., the nucleotide sequence encodes an amino acid sequence for that polypeptide, protein or enzyme.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Preferred vectors are described in the Examples, and include without limitations pcWori, pET26b, pXTD14, pYEX-S1, pMAL, and pET22.

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, and insect host cells and *Baculovirus* vectors.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, acidic, basic, hydrophobic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

"Isolation" or "purification" of a polypeptide or enzyme refers to the derivation of the polypeptide by removing it from its original environment (for example, from its natural environment if it is naturally occurring, or form the host cell if it is produced by recombinant DNA methods). Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the protein or against peptides derived therefrom can be used as purification reagents. Other purification methods are possible. A purified polynucleotide or polypeptide may contain less than about 50%, preferably less than about 75%, and most preferably less than about 90%, of the cellular components with which it was originally associated. A "substantially pure" enzyme indicates the highest degree of purity which can be achieved using conventional purification techniques known in the art.

Polynucleotides are "hybridizable" to each other when at least one strand of one polynucleotide can anneal to another polynucleotide under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency. (such as, for, example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) Polynucleotides that "hybridize" to the polynucleotides herein may be of any length.

The general genetic engineering tools and techniques discussed here, including transformation and expression, the use of host cells, vectors, expression systems, etc., are well known in the art.

The Screening Method

The assay or screening method of the invention is applicable to a variety of enzymes, and is especially well suited for screening oxygenases (monooxygenases and dioxygenases) which are capable of hydroxylating a substrate.

In a broad aspect, the screening method comprises combining, in any order, substrate, oxygen donor, test oxidation enzyme, and coupling enzyme. The assay components can be placed in or on any suitable medium, carrier or support, and are combined under predetermined conditions. The conditions are chosen to facilitate, suit, promote, investigate or test the oxidation of the substrate by the oxygen donor in the presence of the test enzyme, and may be modified during the assay, for example to facilitate action by the coupling enzyme. The coupling enzyme provides a way to detect and measure successful oxidation, that is, the formation of an oxygenated product from the substrate. In some embodiments, one or more cofactors, coenzymes and additional or ancillary proteins may be used to promote or enhance activity of the oxidation enzyme, the coupling enzyme, or both.

In a preferred embodiment of the invention, test enzymes are provided by host cells which have been transformed by genetic engineering techniques, so that they express the test oxidation enzyme. The test enzyme can be produced and retained inside the cell, or it can be secreted outside the cell. In either case, test enzyme can be recovered from host cells for use in an in vitro or "test tube" assay, where the enzyme is combined with the other assay ingredients. Enzyme that is secreted outside the cell can usually be recovered in a non-destructive manner, by collecting it from the growth medium, usually without disrupting the cells, or on a plate where the cells are grown. When the enzyme remains inside the cell, it is typically recovered by breaking open the cells so that the enzyme can be released and separated from the medium and cell debris.

In a more preferred embodiment, it is not necessary to recover test enzyme from host cells, because the host cells are used in the screening method, in a so-called "whole cell" assay. In this embodiment, substrate, oxygen donor, and coupling enzyme are supplied to transformed host cells or to the growth media or support for the cells. In one preferred form of this approach, the test enzyme is expressed and retained inside the host cell, and the substrate, oxygen donor, and coupling enzyme are added to the solution or plate containing the cells. Substrates, donors typically cross the cell membrane and enter the cell. If so, the substrate and donor encounter the test enzyme. Oxygenated products resulting from this encounter may cross the cell membrane (leave the cell) and react at the direction of the coupling enzyme to form a detectable reaction product. Though less desirable, any assay component which does not cross the cell membrane may be introduced directly to the interior of the cell by known means.

These techniques are particularly useful when the coupling enzyme produces a signal that can be observed from outside the cell, such as a luminescent reaction product, or when co-expression of the coupling enzyme is difficult or interferes with the reactivity of the test enzyme. Such measurements are non-destructive, and allow for isolation and further work with cells that produce active enzymes. When a fluorescent signal is used, for example, transformed host cells that produce more active oxidation enzymes "light-up" in the assay and can be readily identified, and distinguished or separated from cells which do not "light up" as much and which produce inactive enzymes, less active enzymes, or no enzymes.

Oxygenated substrate that is secreted by the cell can interact with coupling enzyme in the cell media, to form a detectable extracellular reaction product. If the host cells are grown on a solid support, a fluorescent signal may be identifiable as a ring which "lights up" around cells which product active oxidation enzyme. Depending on how close together neighboring cells are growing, this method may allow for active and non-active host cells to be distinguished, but is probably less reliable than an intracellular method.

In embodiments where all of the host cells in or on a particular medium are producing the same test enzyme, the choice of intracellular or extracellular approach is likely to be determined as a matter of convenience, unless other circumstances favor or require one technique over the other.

In a particularly preferred embodiment, host cells are transformed to produce both a test enzyme and a coupling enzyme. Substrate and donor are added to the cell medium and are taken up by the cells. Active enzyme produces an oxygenated substrate, which is converted to a detectable reaction product by the coupling enzyme.

A preferred detectable reaction product is luminescent, for example fluorescent. This can be achieved, for example, by using a coupling enzyme, such as laccase or HRP, which forms fluorescent polymers from the oxygenated substrate. A chemiluminescent agent, such as luminol, can also be used to enhance the detectability of the luminescent reaction product, such as the fluorescent polymers. Detectable reaction products also include color changes, such as colored materials that absorb measurable UV light.

The method of the invention is indirect in that it does not measure the presence of an oxygenated compound which is produced by action of an oxygenase on a substrate. Instead, the invention detects or measures the reaction product that is made by the action of a coupling enzyme on a successfully oxygenated substrate. In a preferred embodiment, an oxygenated substrate is reacted in the presence of a coupling enzyme to form dimers or polymers of the oxygenated substrate. More particularly, a luminescence that is characteristic of the oxygenated substrate or its polymers is observed or measured. Most typically, the polymers are fluorescent, and can be detected by known means. This is advantageous, because oxygenated substrate may be impossible or very difficult to detect directly. For example, oxygenated substrate may not exhibit fluorescence or any other convenient marker, may do so at very low levels which are difficult to detect, or may do so at a wavelength where there are large interferences from other components of the test mixture. Thus, the invention serves to mark or amplify the oxygenated substrate or product so that is can be reliably detected or measured. The invention is sensitive to enzyme activity, and in addition is sensitive to the position of oxygenation or hydroxylation of the enzyme, i.e. the regioselectivity of the enzyme. For example, different colors may be produced and detected depending on where the enzyme has introduced oxygen.

A schematic representation of chemical reactions used in a preferred embodiment of the screening invention is shown in FIG. 1. An aromatic substrate, for example benzene, a substituted benzene or naphthalene is hydroxylated by an oxidation enzyme. Suitable enzymes include chloroperoxidase (CPO), cytochrome P450s (P450), methane monooxygenases (MMO), toluene monooxygenases, toluene dioxygenases (TDO), biphenyl dioxygenases and naphthalene dioxygenases (NDO), or any of the many mono- and di-oxygenases. An oxygenated product is formed, in which one or more hydroxyl (OH) groups has been substituted at one or more ring positions of the aromatic substrate, e.g. in place of hydrogen. These oxygenated products usually do not fluoresce, or exhibit a very small change in fluorescence, and can be difficult to detect or measure. Treatment with a coupling enzyme, such as a laccase or peroxidase (e.g. HRP) under appropriate conditions produces dimers or polymers of the oxygenated product which are colored or fluorescent, and can be readily detected. A chemiluminescent agent, such as luminol, can be used in addition to the coupling enzyme, to further enhance the detection and measurement of fluorescent oxygenated compounds.

Production of Test Enzymes (Host Cells and Vectors).

In one aspect of the,invention, a whole cell screening method is provided, in which a test oxidation enzyme is produced by a transformed host cell using a suitable expression system. The types of host cells and expression systems which are suitable for use in accordance with the invention are those which are capable of expressing oxidation enzymes. Host cells which can also express coupling enzymes are preferred. *E. coli* is one preferred exemplary cell. Other exemplary cells include other bacterial cells such as *Bacillus Pseudomonas*, yeast cells, insect cells and filamentous fungi such as any species of *Aspergillus* cells. For some applications, such as screening for toxicity of certain compounds, plant, human, mammalian or other animal cells may be preferred.

Suitable host cells may be transformed, transfected or infected as appropriate by any suitable method including electroporation, $CaCl_2$ mediated DNA uptake, fungal infection, microinjection, microprojectile transformation, viral infection, or other established methods. Appropriate host cells include bacteria, archaebacteria, fungi, especially yeast, and plant and animal cells. Of particular interest are *E. coli*, and *Saccharomyces cerevisiae*.

Any of the well-known procedures for inserting expression vectors into a cell for expression of a given peptide or protein may be utilized. Suitable vectors include plasmids and viruses, particularly those known to be compatible with host cells that express oxidation enzymes or oxygenases.

The invention is especially well suited for screening large numbers of mutant oxygenases wherein cells are transformed with a number of different vectors which express different mutant oxygenases. The mutant oxygenase genes can be prepared using procedures such as DNA shuffling, as shown for example in U.S. Pat. No. 5,605,793 (16) or by random mutagenesis, for example using error prone polymerase chain reactions (PCR). See, e.g. U.S. Pat. Nos. 5,741,691 and 5,811,238 (13) and PCT Application No. PCT/US98/05956 (17).

Once the host cell has been transformed with the desired vector expressing the oxygenase to be tested, the cell line is maintained and grown under conditions which promote expression of the oxygenase within the cell. In general, the oxygenase remains within the cell and is not excreted. After the transformed cells have been cultured for a sufficient time to generate oxygenase, the cells are contacted with or otherwise treated with the substrate of interest. This results in the generation of oxygenated compounds within the cell. In most cases, the oxygenated compound will diffuse from the cell where it can be reacted with a coupling enzyme to form polymeric oxygenated compounds. See, FIG. 1. Upon reaction with the coupling enzyme, the oxygenated compound forms dimers or polymers which are colored or fluorescent. The dimer or polymer is detected to provide a measure of the activity of the oxygenase. If desired, luminol or other luminescent or color enhancing material may be added to enhance the signal or provide polymers with long chemiluminescent lifetimes. Preferred cells for these applications are bacterial cells such as *E. coli* and *Bacillus*, and yeast cells, e.g. *S. cerevisiae*, in which libraries of different mutants (dozens or more, and typically thousands) can be made.

Exemplary coupling enzymes which can be used in accordance with the invention include peroxidases and laccases. Specific exemplary enzymes include horseradish peroxidase (HRP), cytochrome c peroxidase, and various other peroxidases from various microbial and plant sources such as soybean peroxidases, tulip peroxidase, lignin peroxidase, carrot peroxidase, peroxidase Novozyme® 502, etc., as well as fungal laccase.

Although it is possible to add coupling enzyme for reaction with oxygenated compound that diffuses from the host cells, it is preferred that the coupling enzyme be co-expressed within the cells to provide an intracellular screening system. The transformation of the cell to express the coupling enzyme is accomplished in a manner similar or analogous to transforming the cell to express the oxygenase.

The result is a cellular system which provides for the indirect detection of the presence of oxygenated compounds which are produced within the cell when a substrate is reacted with an oxygenase expressed within the cell. The co-expression of the coupling enzyme provides a readily available source of enzyme to polymerize the oxygenated compound to form colored, chemiluminescent or fluorescent products which can be detected within the cell.

In general terms, a preferred embodiment of the whole cell screening method includes the following steps.

1) HRP Added to Oxygenase-expressing Cells.

Host cells that express a test oxidation enzyme are grown under conditions that will promote the functional expression of oxygenase activity. The substrate to be oxygenated is added and the oxidation reaction is allowed to proceed under appropriate conditions, e.g. the desired conditions (temperature, substrate, solvent, etc.) for screening which reflect the desired properties of the oxygenase. The cells can also be broken open to release the test oxidation enzyme into the medium. To detect the formation of oxygenated products, a coupling enzyme (e.g. a peroxidase such as horseradish peroxidase) is added to the reaction mixture (typically, the cell growth media), along with an oxygen donor, such as hydrogen peroxide. The substrate can be added before the horseradish peroxidase and peroxide, or it can be added at the same time. In some cases substrate can be added later, but this may be less efficient or otherwise less desirable. In some circumstances (e.g when the substrate is sensitive to peroxide), it is preferable to add the substrate before the other assay components. The advantage of adding substrate, oxygen donor and coupling enzyme contemporaneously is that the assay can then follow the kinetics of the oxidation reaction catalyzed by the oxygenase. The color or fluorescence, indicating the formation of an oxygenated reaction product, will accumulate in the cell culture and can be detected by any number of means. Addition of appropriate compounds (e.g. luminol) may allow the product to be detected by chemiluminescence.

2) HRP Co-expressed with Oxygenase (Intracellular Reaction).

In this embodiment, a test oxygenase and coupling enzyme (e.g. HRP) are both expressed by the host cell, so that coupling enzyme need not be separately added. The cells expressing both the oxygenase and HRP are grown under conditions that will promote functional expression of both activities. The substrate is added; and the reaction is allowed to proceed under appropriate conditions (desired conditions for screening). The color or fluorescence will accumulate in the cells themselves, in the cell culture, or both and can be detected by any number of means. As above, the addition of appropriate compounds (e.g. luminol) during the reaction may allow the product to be detected by chemiluminescence.

Examples of practicing the invention are provided, and are understood to be exemplary only, and do not limit the scope of the invention or the appended claims. A person of ordinary skill in the art will appreciate that the invention can be practiced in many forms according to the claims and disclosures here.

EXAMPLE 1

Whole Cell Screening For Naphthalene Hydroxylation by Cytochrome $P450_{cam}$ with Added Horseradish Peroxidase (HRP)

This example sets forth an exemplary fluorogenic whole cell activity assay for hydroxylation of naphthalene by a mutant cytochrome P450 enzyme. This simple whole cell screening procedure avoids problems associated with assays that require disruption of cells or centrifugation steps. The example demonstrates that large libraries of enzyme mutants can be screened rapidly and effectively using the methods of the invention.

Naphthalene, an aromatic hydrocarbon, exhibits weak fluorescence. When taken up by *E. coli* host cells that express the oxygenase $P450_{cam}$, naphthalene is hydroxylated by the enzyme to produce an oxygenated product with a weak but characteristic fluorescence emission (em) at a wavelength of 430–465 nm. When hydroxylated naphthalene diffuses out of the cell, the $P450_{cam}$ activity is determined fluorometrically by amplifying the weak fluorescence. In accordance with the invention, HRP-catalyzed polymerization of the hydroxylated product results in a large increase in the fluorescence intensity and this is used for high throughput screening of catalysts. Although the hydroxylated naphthalene shows blue fluorescence at high concentration levels, the colonies, having a low intracellular concentration of hydroxylated naphthalene are only weakly fluorescent. With HRP-assisted fluorescence intensification, very low levels of $P450_{cam}$ activity can be detected. Therefore, there is significant benefit in terms of sensitivity to screening the enzyme mutants for improvements in activity by this method.

Cells, Enzyme and Chemicals.

All analytical grade of chemicals were used. Horseradish peroxidase (type II, E.C. 1.11.1.7, oxidoreductase) was purchased from Sigma Chemical Co. Naphthalene and its hydroxylated derivatives, 1-naphthol and 2-naphthol, were purchased from Sigma and Aldrich. ABTS [2,2'-azino-bis (3-ethylbenzthiazoline-6-sulfonic acid] and 30% hydrogen peroxide solution were purchased from Sigma. Isopropyl-beta-d-thiogalacto-pyranoside (IPTG) was purchased from ICN Biomedicals, Inc. (Aurora, Ohio). Thiamine, glycerol and delta-aminolevulinic acid (ALA) were purchased from Sigma. Buffers were prepared from analytical grade reagents (pH9: 100 mM dibasic sodium phosphate buffer, pH 7.45: 100 mM tris-HCl buffer, pH 7.0: 100 mM potassium phosphate buffer). The *E. coli* host cells used here were strains designated as *E. coli* XL10 Gold and BL21(DE3), obtained from Stratagene, La Jolla Calif. (Catalog Nos. 200317 and 20013 1).

Trace Element Stock:

1 liter HCl solution (90% v/v distilled water: concentrated HCl) containing 0.5 g $MgCl_2$, 30 g $FeCl_2.6H_2O$, 1 g $ZnCl_2$. $4H_2O$, 0.2 g $CoCl_2.6H_2O$, 1 g $Na_2MoO_4.2H_2O$, 0.5 g $CaCl_2.2H_2O$, 1 g $CuCl_2$, and 0.2 g $H_3BO_3$.

The same materials, cells, enzymes, chemicals, and trace elements stock were used, or can be used, in each of the Examples. Where significant, any differences in the subsequent Examples are noted.

A. Optimizing Expression of Recombinant $P450_{cam}$ in *E. coli*.

An *E. coli* expression system was devised to provide host cells which are transformed by plasmid vectors containing DNA that encodes for mutant P450 oxygenases. The resulting transformants each express mutant P450 enzyme as a test oxidation enzyme for use in the invention. As shown, expression conditions were identified that reproducibly promote a high expression of $P450_{cam}$ in *E. coli*. The determination of other appropriate conditions, including selective modification of expression conditions to suit the particular needs of the assay, are well within the skill of the art.

Figure 2:
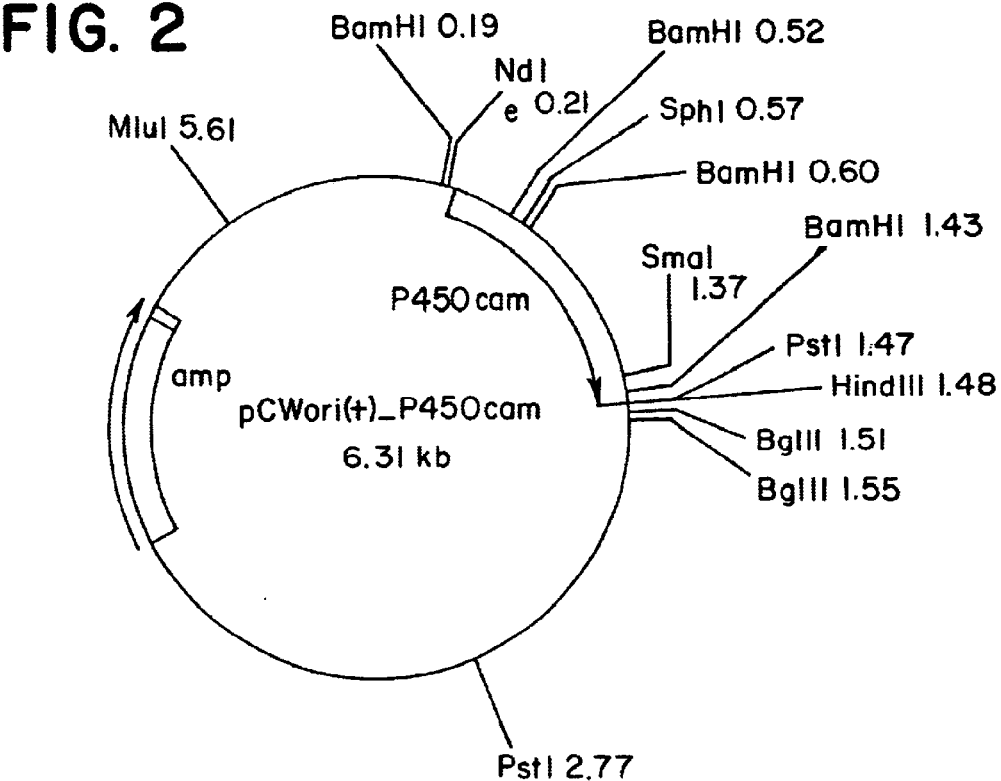
FIG. 2 is a map of an exemplary vector used to express the wild type cytochrome $P450_{cam}$ oxygenase and its mutants in E. coli.

Expression was undertaken with *E. coli* XL-10 Gold cells (from Stratagene) transformed with the expression vector pCWori(+)_$P450_{cam}$. See, FIG. 2. The plasmid backbone of pCWori+ contains a pBR322 replication origin, the lac Iq gene, Amp, and a bacteriophage origin of replication. The plasmid also contains a lac UV5 promoter and a double Ptac promoter region followed by a translation initiation region. The DNA sequence inserted into the plasmid backbone comprises the structural gene of $P450_{cam}$. A nucleotide sequence encoding this enzyme is set forth in FIG. 3A [SEQ. ID. NO. 1]. This gene produces the native $P450_{cam}$ oxidation enzyme of *P. putida* when cloned into the *E. coli* host cell using the pCWori(+) plasmid as an expression vector. The amino acid sequence of this enzyme is shown in FIG. 3B [SEQ. ID. NO. 2].

Host cells transformed with this vector can serve as a control or comparison for other P450 enzymes, or other oxidation enzymes, or they can be used to produce test enzymes for use in the screening method of the invention. For example, other P450 genes, including new strains of native P450 or mutants of P450 genes may be transformed into *E. coli* host cells using the same or a similar plasmid system.

Experiments were done in both culture flasks scale and, on a smaller scale, in 96-well microtitre plates, with LB media, Terrific broth (TB), and modified minimal media (M9, containing 20% glucose or glycerol). All of these media were evaluated for induction optimization, using 1.0 mM IPTG as the inducer to activate synthesis (transcription) of the P450 oxidation enzyme in *E. coli*. For optimization of expression levels, *E. coli* XL-10 Gold ultra-competent cells (Stratagene, La Jolla, Calif.) transformed with pCWori+_ P450cam were grown on LB/Amp plates at 37° C. overnight. Single isolated colonies of transformed *E. coli* cells were then seeded into 2 ml volume of LB/amp culture media. After 8 hr growth at 37° C., an aliquot (0.5 ml) of this culture was used to inoculate a 50 ml volume of each different culture medium: LB/amp, TB/amp, and modified M9 (glucose or glycerol)/amp minimal media. One hundred microliters of pre-prepared trace element stock and 1 mM thiamine (vitamin B1) were added to each flask of the 50 ml culture media. After 8–12 hour growth (8 hours for TB, 12 hours for M9), the flask cultures were cooled to 30° C. ALA was added (it is unstable at higher temperatures) and the cells were induced with IPTG for 24 hours.

For growth and screening in 96-well plates, one loop-full of single colonies was picked from the parent plate and directly transferred into TB/amp or M9 (glucose or glycerol)/amp media and incubated at 37° C. in wells of a 96-well microtitre plate. All the additives added in the growth medium and induction conditions are the same as for the flask culture conditions described above.

$P450_{cam}$-mediated hydroxylation activity was estimated on naphthalene (NP) as the substrate. Horseradish peroxidase (HRP), as a purified form, was used as a coupling enzyme. The rate of NP conversion, which is proportional to the total amount of P450 wild-type enzyme expressed, was found to be influenced by the additives used. For example, the whole cell hydroxylation activity increased dramatically when ferrous chloride ($FeCl_2$) and thiamine (vitamin B1) were added for all media tested. At least 60 times higher activity was obtained, even in M9 minimal conditions (M9 glucose and M9 glycerol), as compared to the media which do not contain these two additives. However, addition of ALA (0.5–1.3 mM) resulted in a relatively small increase (20–25%) in $P450_{cam}$ activity, as compared to the thiamine and $FeCl_2$ addition, which appeared 24–48 hours into the induction period, reached a maximum at ~24 hours, and declined thereafter. Control cultures using the same plasmid pCWori(+)_P450$_{cam}$ transformed into an E. coli strain that received no addition of those cofactors (thiamine, FeC$_2$, ALA) produced very little or no P450$_{cam}$ activity during at least 48 hour culture.

The medium formulation that has been found to be the most useful for obtaining the highest whole cell activity in 96-well plates and flask cultures was Terrific Broth (TB). A 1.5-fold increase in whole cell activity was obtained when the cells were grown in Terrific broth (TB) containing 1.3 mM ALA, as compared to M9 media. One or more of these additives may be used as additives in practicing the invention, and other suitable additives may also be used in other embodiments. Reaction conditions and procedures for the whole cell activity assay on a 96-well microplate are shown in FIG. 4A.

B. P450$_{cam}$ Purification Using Maltose-binding Fusion Affinity Tag

To check whether the wild type P450$_{cam}$ can catalyze the naphthalene hydroxylation reaction using hydrogen peroxide as the oxygen donor, P450cam was expressed and purified using the maltose-binding fusion (MBP) vector pMAL-C2 from New England Biolabs (Beverly, Mass.). The P450$_{cam}$ gene from the pCWori(+)_P450$_{cam}$ vector was cloned into Xmm I and Hind III sites of the MBP expression vector at the 3' end of the malE-factor Xa cleavage site. The pCWori(+)_P450$_{cam}$ vector was linearized with NdeI (contains P450$_{cam}$ start codon, ATG), blunt-ended with Klenow (5'-3' exo-, incubated with 2.5 mM Li salt-free dTTP) and Mung bean nuclease. After the Hind III cut, the P450$_{cam}$ gene fragment was purified by using agarose gel extraction and then ligated to the MBP vector. The MBP expression vector contains an ampicillin marker gene and a lacZ alpha fragment. Transformation of E. coli (DH5alpha) was carried out using CaCl$_2$ and heat shock (45 seconds at 42° C.). For selection of ampicillin resistance and the complete gene insert, cells grown on LB/amp agar plate was transferred to a fresh medium containing 20 ug/ml X-gal.

For P450$_{cam}$ purification, a transformant was cultivated in 500 ml TB/amp liquid medium. Except for addition of 2.35 g/l glucose, all induction and protein expression conditions were the same as described in the above in section A. (Optimizing expression of Recombinant P450$_{cam}$ in E. coli). Affinity separation using an amylose column was done as described by Riggs (1990) (37). The final concentration of the purified MBP-P450$_{cam}$ fusion protein (c.a. 88 kDa) was approximated by the ratio of coomassie blue dye intensities with a protein standard marker after the SDS-polyacrylamide gel electrophoresis. The final concentration of MBP-P450$_{cam}$ is estimated to be 5×10$^{-8}$ M (Mw 89,000).

C. P450cam Hydroxylation Assay Using Whole Cells and Purified Protein

The activity of P450$_{cam}$ in E. coli was checked by measuring the conversion of naphthalene (NP) to a hydroxylated product (e.g., 1-naphthol, 2-naphthol) which emits a blue fluorescence (1max fl.: 465 nm with 350 nm excitation) when the exogenously added HRP polymerizes the product. The hydroxylated NP presumably diffused out of the cells, and the fluorescence was intensified by the addition of HRP and hydrogen peroxide.

Cells grown in 96-well microplates or flasks were harvested and carefully resuspended in 0.1–1 ml of dibasic sodium phosphate buffer (pH 9.0, 100 mM). 50 µL of this solution was then added into the same buffer (total 200 µl) containing reaction mixtures. A cell washing step is optional in both cases (however, this step reduces background fluorescence level).

Reaction conditions and procedures for the whole cell activity assay on a 96-well microplate are shown in FIG. 4A. In Step I, individual colonies showing fluorescence in the first screening are each loaded into a well of a 96 well plate containing 100 µL of TB media. In Step II, the colonies are allowed to grow overnight at 37° C. Then, in Step III, they are induced for 24 hours at 30° C. with a 120 µL volume of IPTG and trace elements (0.5–1 mM IPTG, 1 mM thiamine, 0.5–1.3 mM ALA, and 0.5 Trace Elements Stock per 10 mL of media. This induces expression of the P450$_{cam}$ enzyme. In Step IV, a test solution of substrate and oxygen donor is introduced, to provide reactants for the oxidation reaction catalyzed by P450$_{cam}$. The test solution contains:

|  | 50 µL | culture broth (from flask or 96-well culture) |
|---|---|---|
|  | 100 µL | sodium dibasic phosphate buffer (50 mM, pH 9) |
|  | 10 µL | pure ethanol |
| substrate | 20 µL | naphthalene stock (saturated; 1 g/13 ml in pure ethanol) |
| oxidant | 10 µL | hydrogen peroxide stock (100 mM) |
| coupling enzyme | 10 µL | HRP stock (1400 units/10 ml) |
|  | 200 µL |  |

The characteristic blue fluorescence generation inside the cells was measured in a Perkin Elmer HTS 7000 96-well microplate fluorescence reader (emission at 465 nm with excitation at 350 nm). A 96-well white microplate (Nunc, VWR) was used to reduce the background fluorescence of the reaction chamber during the detection and integration time (20 ms).

The substrate was 20 µL of a saturated solution of naphthalene (NP) in ethanol (EtOH). The oxygen donor was a final concentration of 5 mM hydrogen peroxide (H$_2$O$_2$), and the coupling enzyme was 10 µL of HRP. The volume was adjusted to 200 µL with culture broth, buffer and ethanol. The oxygenation reaction, as an indication of P450$_{cam}$ activity, was measured using a Perkin Elmer HTS 7000 96 well microplate fluorescence reader (emission at 465 nm with excitation at 360 nm; Gain 54; measurement time 32 minutes).

The assay reaction scheme is shown diagrammatically in FIG. 4B. A naphthalene substrate and a hydrogen peroxide (H$_2$O$_2$) oxygen donor are introduced to whole cell cultures of E. coli host cells transformed with pCWori(+)_P450$_{cam}$ plasmid. The plasmid contains DNA encoding the P450$_{cam}$ enzyme. The substrate and oxygen donor enter the cells, where the substrate is oxygenated in an oxidation reaction mediated by the P450$_{cam}$ enzyme. This results in oxygenation of the naphthalene substrate, to produce a hydroxylated compound or reaction product which exhibits a weak yet characteristic fluorescence. In the presence of the horseradish peroxidase (HRP) enzyme and additional hydrogen peroxide, the oxygenated compound forms a highly fluorescent polymer, which can be accurately detected.

Purified MBP-P450$_{cam}$ was also used to carry out this reaction. In this case, the naphthalene hydroxylation activities were measured in 200 µL reactions in a 96-well microplate. 5.28×10$^{-9}$ M MBP-P450 fusion protein (one tenth dilution of the purified protein) was added to the dibasic sodium phosphate buffer containing 7 units horseradish peroxidase in purified form, and 10 mM naphthalene. Reaction was initiated after the addition of hydrogen peroxide (2.5 mM and 5 mM). The fluorescence increase (RFU, fluorescence measurement unit) was measured at the same emission and excitation using the microplate fluorescence reader.

D. Results of 96 Well Plate Assay

Figure 5B:
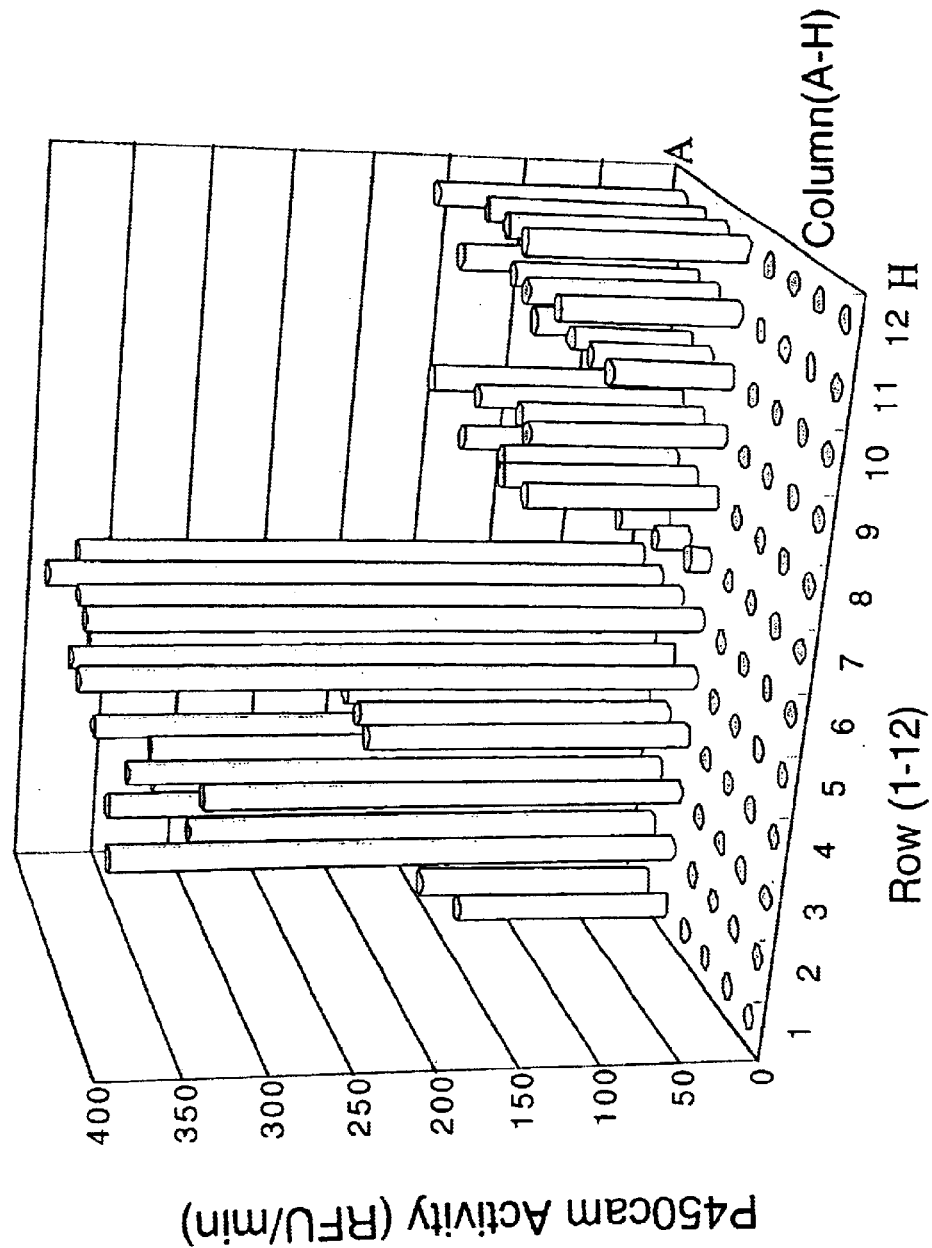
FIG. 5B is a graphic representation of $P450_{cam}$ activity as measured by an assay according to the invention. Each column of the graph represents the total $P450_{cam}$ activity in each corresponding well of the 96 well plate, as a measure of the fluorescence produced by the polymerized oxygenated reaction products of naphthalene hydroxylated by hydrogen peroxide in the presence of the $P450_{cam}$ and HRP enzymes.

A screening experiment conducted on a 96 well plate is shown in tabular or chart form in FIG. 5A. The results of this screening, using the described 96 well plate embodiment of the invention, are shown in FIG. 5B.

In this assay, whole cell activity for naphthalene hydroxylation by P450$_{cam}$ and hydrogen peroxide is evaluated for different media (TB, M9 glucose and M9 glycerol) with different concentrations of ALA (0.5 and 1.3 mM) in each of a series of wells on the 96 well plate. See FIG. 5A. As described above, each reaction was induced by 1 mM IPTG, 1 mM thiamine, and 0.5–1.3 mM ALA, with trace elements. Columns A–D of the 96 well plate contained E. coli host cells transformed to produce P450$_{cam}$ (pCWori(+)_P450cam vector was used). Columns E–H contained E. coli cells which were not transformed to produced P450$_{cam}$ (control strain (XL-10 Gold)). Rows 1–3 of the 96 well plate contained Terrific Broth (TB) and 0.5 mM ALA. Rows 4–6 contained Terrific Broth (TB) and 1.3 mM ALA. Rows 7–9 contained M9 glucose media and 0.5 mM ALA. Rows 10–12 contained M9 glycerol media and 0.5 mM ALA. The first row of each group of three rows used 200 µL of cultivation volume. The other two rows of each group of three used 100 µL of cultivation volume.

Fluorescence in each well was measured using a microplate fluorescence reader [Perkin Elmer, HTS 7000]. The degree of fluorescence provides an indirect yet accurate indication of oxygenated substrate, which in turn provides a measure of P450$_{cam}$ activity.

As shown in FIG. 5B, lower P450 activity was seen for the larger, 200 µL cultivation volume that contains a smaller concentration of substrate and oxygen donor, compared to the lower (more concentrated) cultivation volume of 100 microliters. (Compare Rows 1, 4, 7 and 10 (200 µL volume) with the other Rows (100 µL volume)). This demonstrates that the observed fluorescence, and degree of fluorescence, is indeed tracking the P450 enzyme reaction and oxygenation of interest. The results also show that TB is a significantly more favorable medium than either of the M9 media tested, and the higher concentration of ALA (1.3 mM) is marginally more favorable than the lower concentration tested (0.5 mM). ALA is an important heme synthesis intermediate (P450 is a heme-protein), and the synthesis of P450 in host cell cytoplasm is regulated in part by the concentration of the synthesized heme. A high level of P450$_{cam}$ protein expression (total activity: 430 RFU/min) was obtained using TB and 1.3 mM ALA, 100 µL volume.

The experiment shows that host cells can be effectively transformed to express and active P450 enzyme which can be used to catalyze the oxygenation of a substrate in a whole cell assay adapted for high throughput screening, for example, in a 96 well plate format. The fluorescence produced by oxygenated substrate such as hydroxylated naphthalene can be reliably detected and measured, particularly when amplified by a coupling enzyme such as HRP.

To back up these results, P450$_{cam}$ peroxide-shunt pathway utilization was checked using the purified MBP-P450$_{cam}$ enzyme. Considerable increase of the poly(naphthol) fluorescence was observed: 6.8±0.5 a.u. (RFU)/min/nmol with 2.5 mM H$_2$O$_2$, and 19.7±0.5 a.u. (RFU)/min/nmol with 5 mM H$_2$O$_2$, in the absence of NADH and two ancillary electron transfer proteins (putidaredoxin and reductase). This supports the finding that P450$_{cam}$ can utilize hydrogen peroxide as an oxygen donor in this reaction.

EXAMPLE 2

Whole Cell Screening for Naphthalene Hydroxylation by Image Analysis and Co-expression of P450$_{cam}$ with Horseradish Peroxidase (HRP)

This example demonstrates that co-expression of HRP with P450 monooxygenase leads to the accumulation of fluorescence inside cells, which can be monitored by digital image analysis. In EXAMPLE 1, above, HRP was added to whole cells transformed to express P450$_{cam}$. In this Example, E. coli host cells are transformed to express both enzymes, HRP and P450$_{cam}$. In this way, it is not necessary to add HRP in a separate assay step, nor is it necessary to monitor the growth medium for changes in fluorescence that indicate oxygenation and P450$_{cam}$ activity. In host cells transformed to produce both enzymes, the assay reaction occurs inside the cells when substrate and oxygen donor are provided, e.g. naphthalene and hydrogen peroxide. The fluorescence of, inside, and/or around cells that are producing an oxygenated compound and polymer (mediated by the two enzymes) can be detected and measured.

Detailed methods used in this example are given below.

A. Co-expression of Recombinant HRP1A6 and P450$_{cam}$ in E. coli.

Genes and Plasmids.

An HRP mutant gene that produces active HRP in E. coli was prepared as described in EXAMPLE 9 and in U.S. Provisional Application Serial No. 60/094,403 filed Jul. 28, 1998. This gene encodes a mutant HRP identified as "HRP1A6". The gene for HRP1A6 was restricted from pETpelBHRP1A6 and cloned into the kanamycin resistant vector pET26b(+) (Novagen, Madison Wis.), yielding pETpelBHRP1A6Kan. Except for the antibiotic marker, this vector is identical to pETpelBHRP1A6 set forth in FIG. 24. Expression vector pCWori(+)_P450$_{cam}$ was prepared as set forth in EXAMPLE 1.

pCWori(+)_P450$_{cam}$ and pETpelBHRP1A6Kan Transformation.

Chemical transformation using CaCl$_2$ (60 mM) and heat shock (45 seconds at 42° C.) was used to introduce the pETpelBHRP1A6Kan plasmid into E. coli BL21(DE3). Successful transformants were identified by selection on LB/kan (6–30 µg/ml kanamycin) agar plates. Positive clones were then made chemically competent and transformed with the second plasmid, pCWori(+)_P450$_{cam}$. Identification of the E. coli BL21(DE3) clones containing both genes were identified by growth on LB/kan (30 µg/ml)/amp (100 µg/l amp) plates. The abbreviation "amp" indicates the antibiotic ampicillin, and "kan" indicates the antibiotic kanamycin. Cells than contain the Amp or Kan DNA fragments will grow in media that contains the respective antibiotic. This can be used as a so-called "selection marker", according to well known techniques, to identify and isolate different groups of cells with different properties using the ability or inability to resist antibiotic as a label.

B. Cell Growth and Reaction on Agar Plate for Image Analysis

Figure 6:
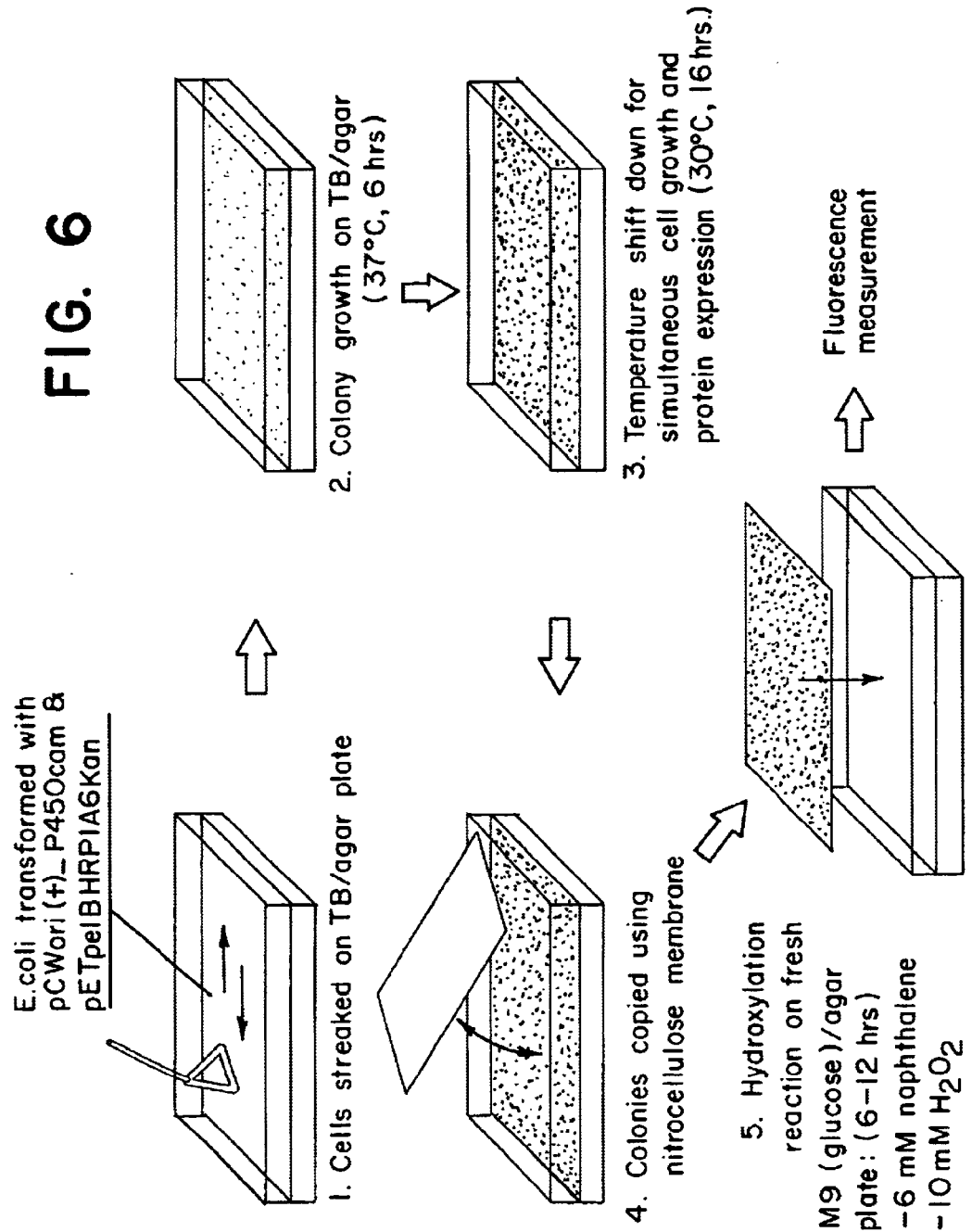
FIG. 6 is a pictorial representation of an exemplary assay according to the invention.

In this procedure, pure cultures of transformed E. coli (containing pCWori(+)_P450$_{cam}$ and pETpelBHRP1A6Kan) were seeded onto TB/agar plates (Falcon, #1007 or Q-bot) supplemented with 100 µg/ml ampicillin, 30 µg/ml kanamycin, 100 µl/50 mL trace element stock solution, 0.25 mM thiamine, 1 mM ALA and 0.5 mM IPTG, and were grown at 37° C. for 6 hours, at which point the incubation temperature was lowered to 30° C. to obtain small and even colony size distribution (<0.8 mm diameter) for accurate hydroxylation activity detection. The growth temperature shifting from 37° C. (after 6 hours) to 30° C. is preferred for uniform cell growth control, which facilitates image analysis. It was found that cells grown at 37° C. for 24 hours generally contained both smaller as well as larger cells which can not be as readily used for image analysis. After 16 hours incubation for simultaneous cell growth and protein expression, the colonies formed in the parent plates were copied (to make a replica) and transferred onto a nitrocellulose membrane, and then were incubated on a fresh agar/M9/10% (w/v) glucose/5% (v/v) ethanol plate containing 6 mM naphthalene and 10 mM hydrogen peroxide for screening by fluorescence image analysis. The optimal temperature and time for this naphthalene hydroxylation were estimated to 30° C. and 12 hrs. The detailed methods are described in FIG. 6.

$P450_{cam}$ Hydroxylation Assay Using Whole Cell Co-expressing P450cam and HRP.

Host cells transformed to express $P450_{cam}$ and HRP grown in 10 ml TB/amp/kan (100 μg/mL ampicillin, 30 μg/mL kanamycin) contained 0.2 mM thiamine, 1 mM ALA, and 20 μL trace elements stock solution. The grown cells were harvested and carefully resuspended in 1 ml of dibasic sodium phosphate buffer (pH 9.0, 100 mM). After the addition of 10 μl naphthalene stock (0.5 g/13 ml pure ethanol at 25° C.), 10 μl ethanol, and 10 μL hydrogen peroxide solution (stock: 100 mM) to the 170 μL cell suspending solution (total 200 μl reaction volume), the characteristic blue fluorescence generation inside the cells was measured by a Perkin Elmer HTS 7000 96 well microplate fluorescence reader (emission at 465 nm with excitation at 350 nm). A 96 well white microplate (Nunc, VWR) was used to reduce the background fluorescence of the reaction chamber during the detection and integration time (20 ms). See, EXAMPLE 1 and FIG. 4A.

HRP Activity Assay.

The activity of peroxidase expressed in *E. coli* BL21 (DE3) transformed using the vector pETpelBHRP1A6Kan, described above, was estimated colorimetrically by using ABTS (2,2'-azino-bis(3-ethylbenzthiazoline-6-sulfonic acid). Cells were harvested by centrifugation (Beckman CS 6R) at 3,350 rpm and resuspended in 1 ml of 100 mM potassium phosphate buffer (pH 7.5 at 25° C.). A 50 μL aliquot of this mixture was added to 40 μL of 6.4 mM ABTS solution. ABTS oxidation was monitored at 405 nm using a thermostatted spectrophotometer (Perkin Elmer UV/VIS Lambda 20) at 25° C.

C. Results of Screening for Co-expression of $P450_{cam}$ and Mutant HRP C in *E. coli*.

Figure 7:
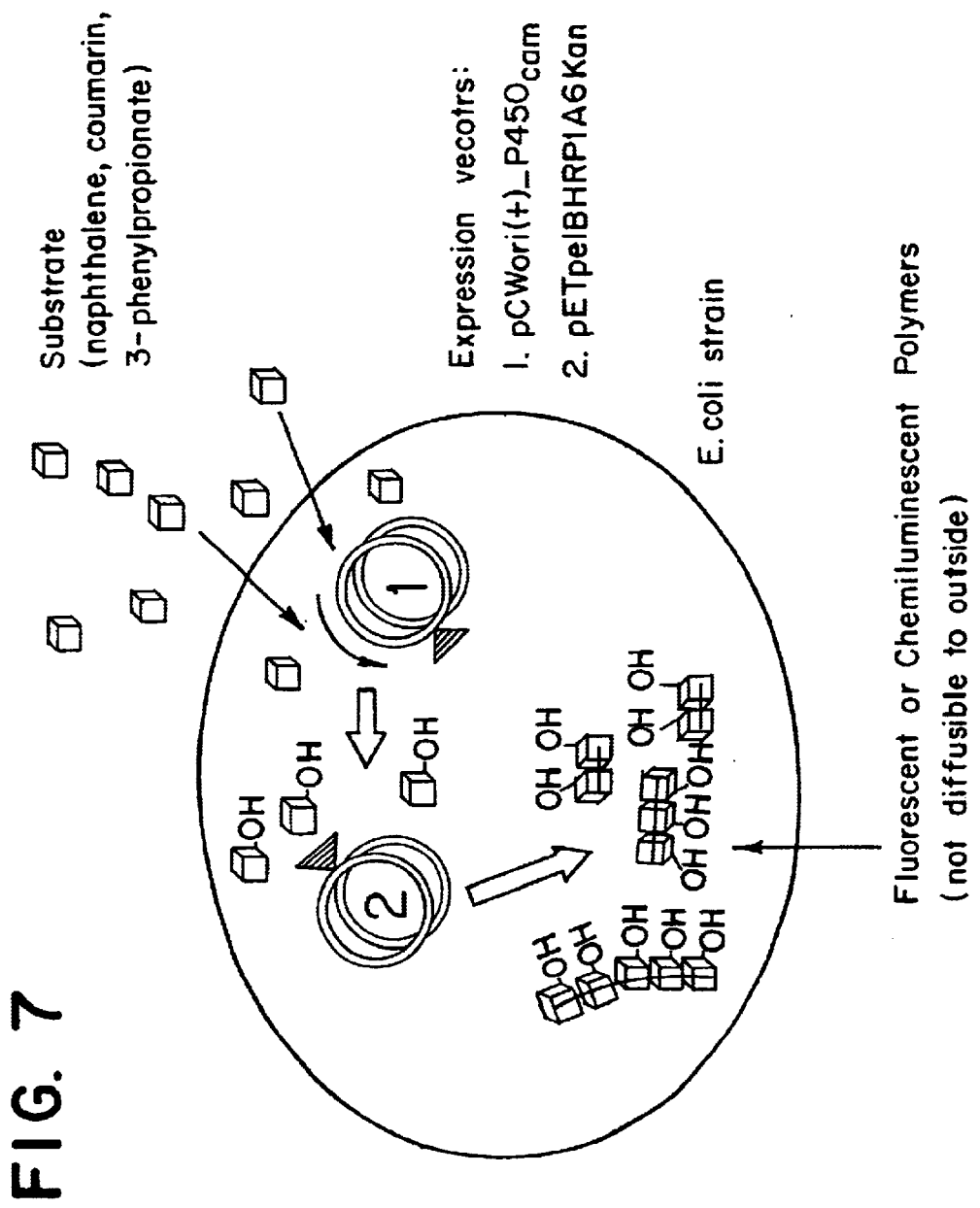
FIG. 7 is a pictorial representation of how simultaneous expression of the oxygenase and coupling enzyme in E. coli leads to generation of fluorescent cells.

This embodiment of the assay can be depicted as shown in FIG. 7. A host cell such as *E. coli* (e.g. strain BL21(DE3)) is transformed by two expression vectors: (1) the plasmid pCWori(+)_$P450_{cam}$; and (2) the plasmid pETpelBHRP1A6Kan. Transformed cells can be cultured from individual cells or colonies, to produce a source of transformant for use in an assay of the invention. A substrate (e.g. naphthalene) and oxygen donor (e.g. hydrogen peroxide) are introduced to the transformed host cells under favorable conditions (e.g. conditions which induce P450 expression and/or activity). These reactants, together with any added cofactors or coenzymes, enter each cell, where they encounter the P450 enzyme being produced there. The P450 catalyzes the hydroxylation of substrate (addition of oxygen in the form of a hydroxide group, OH) to form, for example, hydroxylated naphthalene. In the presence of a coupling enzyme also produced within the cell, such as HRP, the hydroxylated naphthalene forms oxygenated dimers and polymers which are highly fluorescent and have a characteristic fluorescence profile that can be readily detected. Typically, the polymeric oxygenated compounds do not leave the cell. Thus, the accumulation of hydroxylated product in the transformed cells provides significant advantages for detecting and measuring fluorescence, and for identifying cells which successfully produce P450 enzyme and which do so at relatively high levels. As shown coumarin, 3-phenylpropionate and other substrates may be used in place of naphthalene.

The construction of this screening system is based on inducible prokaryotic expression vectors that allow the active co-expression of both enzymes, $P450_{cam}$ and HRP, in the same host strain. As described, a pCWori+ vector which contains the $P450_{cam}$ gene was inserted in *E. coli* BL21 (DE3). This results in *E. coli* host cells that express the introduced P450 gene, and produce a functional P450 enzyme that can be used to catalyze the first reaction in the assay, the oxygenation reaction described above. For the second enzymatic reaction, the coupling reaction, an active HRP mutant gene inserted into a pET26b expression vector was also transformed into *E. coli* BL21(DE3) as described above. Alternatively, cytochrome c peroxidase (CCP) can be used as the coupling enzyme, and a functional gene expressing this enzyme can be transformed into *E. coli* or into a yeast host cell using similar means. Yeast can also be used as the host cell for expression of P450 enzymes, or co-expression of oxygenase and coupling enzyme. Characteristics of these expression vectors are summarized in TABLE 1.

TABLE 1

Characteristics of plasmids used for coexpression of P450cam with HRP and CCP coupling enzymes.

| Gene insert; vector | Promoter type | Replication origin | Antibiotic marker | |
|---|---|---|---|---|
| P450cam from *P. putida* (ATCC17453); pCWori+ | Ptac Ptac | PBR322 | Amp$^r$ | *RBS and I.C.spacing: 3bp |
| HRP1A6; pET-26b(+) | T7 | PBR322 | Kan$^r$ | pET-26b(+) contains pelB leader |
| Cytochrome c peroxidase from *S. cerevisiae*; pET-26b(+) | T7 | PBR322 | Kan$^r$ | **no pelB leader |

*3 bases spacing between ribosomal binding site and initiation codon.
**pelB leader sequence was removed from the original pET-26b(+) vector to avoid protein secretion.

Figure 8:
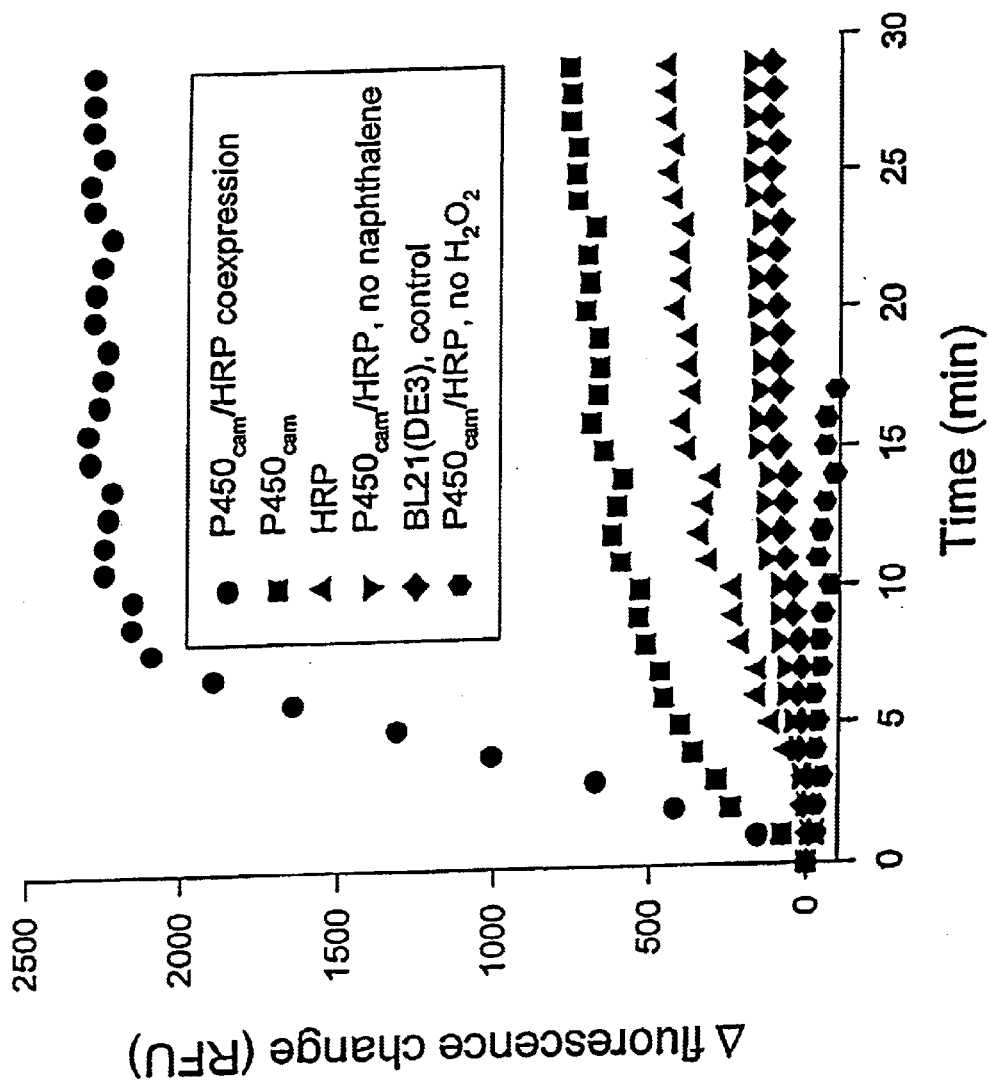
FIG. 8 shows development of fluorescence, over time, in whole cells transformed to co-express P450 oxygenase and HRP coupling enzyme with naphthalene substrate and hydrogen peroxide oxygen donor (●); without naphthalene substrate (▼); and without oxygen donor (◆). For comparison, fluorescence was also evaluated in whole cells transformed to express HRP without P450 (▲), P450 without HRP (■) and host cell that were not transformed (◆).

The experimental time course of the fluorescent product generation using this co-expression system is illustrated in FIG. 8. With the HRP/$P450_{cam}$ double vector system, a more than 370% increase in absolute cell fluorescence level was observed after the 30 minute reaction with 5 mM hydrogen peroxide.

Figure 9:
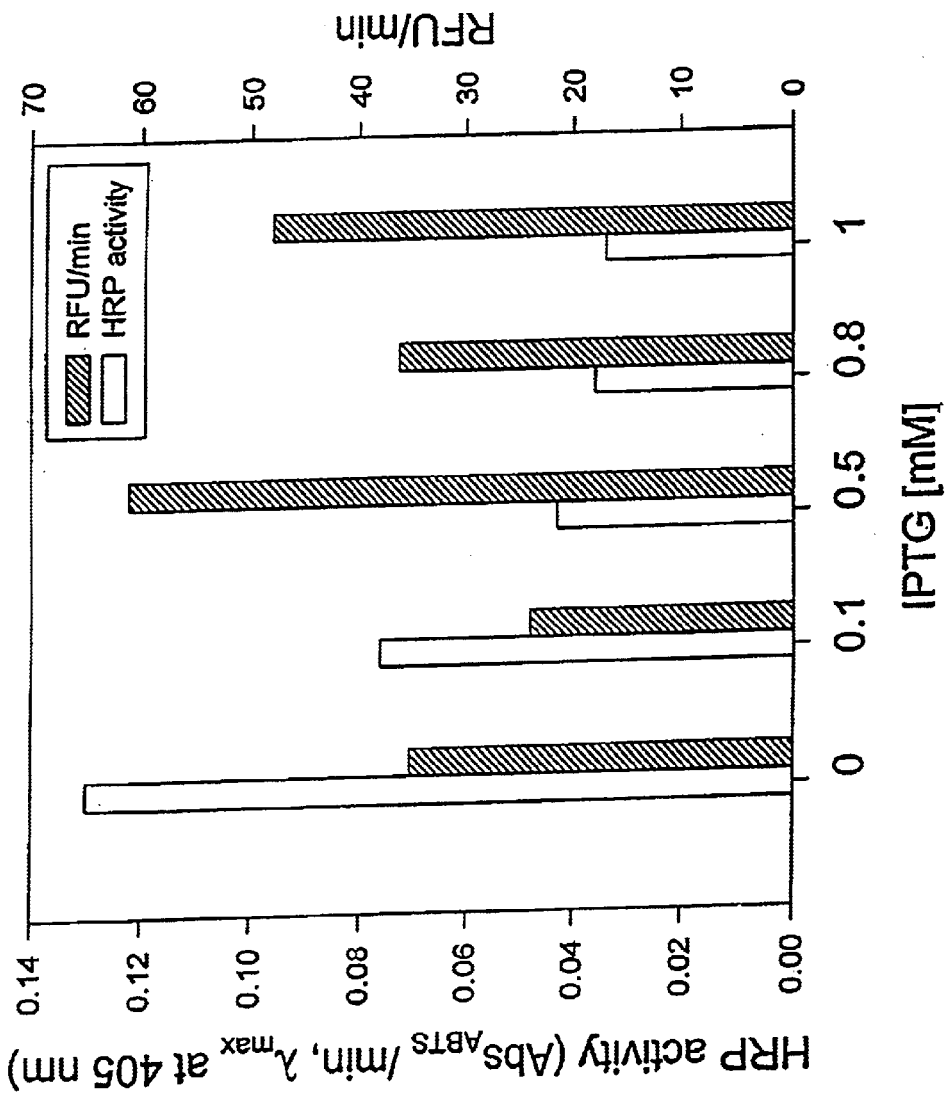
FIG. 9 shows the effect of inducer levels on co-expression and production of P450 enzyme and HRP enzyme in E. coli host cells, according to a preferred embodiment of the invention.

A study of the effects of IPTG concentration over the range 0–1 mM indicated that 0.5 mM IPTG is optimal for the coupled $P450_{cam}$/HRP *E. coli* BL21(DE3) co-expression system used in this example. As shown in FIG. 9, this concentration of IPTG induces the highest activity for P450 enzyme in the presence of an appropriately high HRP activity. Thus, co-expression of $P450_{cam}$ and HRP at appropriate levels (IPTG~0.5 mM) resulted in marked intensification of intracellular fluorescence level.

This co-expression system is advantageous in that the fluorescence remains associated with the cell (nondiffusible). The background intensities either remained constant with time (host strain as a negative control) or showed small increases with time (cells without naphthalene or hydrogen peroxide). As a result, intracellular HP expression with $P450_{cam}$ activity in BL21(DE3) was shown to be an effective self-contained and complete screening system for detecting hydroxylation reactions which utilize the peroxide-shunt pathway. Although P450$_{cam}$ itself also produces fluorescent naphthols, the total intensity measured was lower than the HRP/P450$_{cam}$ co-expression system.

D. Image Acquisition, Processing and Analysis

Images of whole cell fluorescence on agar plates were scanned using Eagle Eye II and a top-mounted 350 nm ultraviolet illuminator (Stratagene, La Jolla, Calif.). Images were digitally analyzed using the software package Optimas 5.0 (Optimas Corporation, WA). Gray-level fluorescent colonies were filtered using a blue fluorescence band-path filter with excitation at 350 nm to remove background fluorescence. Setup parameters for the acquisition of the fluorescent signals using this BL21(DE3) system are as follows: blue band-pass filter (430–470 nm range), lens zoom level=4×, fluorescence image exposure time=1/10 second. Selected gray-level colonies were analyzed with a charge-coupled device (CCD) and subsequent computer-assisted image analysis. A weighted score of 255 was used, with zero as the bottom value and 255 as the highest fluorescence intensity. (This configuration can be modified as appropriate.)

The background mean averaged fluorescence intensities of the host $E.$ $coli$ strain BL21(DE3) (plasmid-free control strain) were estimated to be 0 to 5. Fluorescence intensities were calculated based on the 27,000-grade scale. The fully automated image segmentation algorithm (pattern recognition and back-propagation algorithm) for colony recognition and size measurement was adapted to avoid time-sensitive and subjective manual tracing of colony contours. Individual colony size measurement and automatic single isolated colony detection were derived from computer-determined colony boundaries and fluorescence differences with different sets of threshold levels. The estimated total analysis time was about 5 seconds for $10^5$ colonies.

Blue fluorescence is derived from the products synthesized by the coupled enzymatic reactions catalyzed by P450$_{cam}$ and HRP. The scanned fluorescent images gave a clear result which is well correlated with the specific P450$_{cam}$ hydroxylation activity. It is suggested that smaller individual colonies are better for fluorescence image analysis. The maximum size limit of the colony for this image analysis was estimated to be 0.8 mm diameter. Typical dimensions of the imaged colonies were ~0.4 to 0.8 mm in diameter, and there were approximately 9 to 17% fluorescence value deviations within this size distribution.

Figure 10:
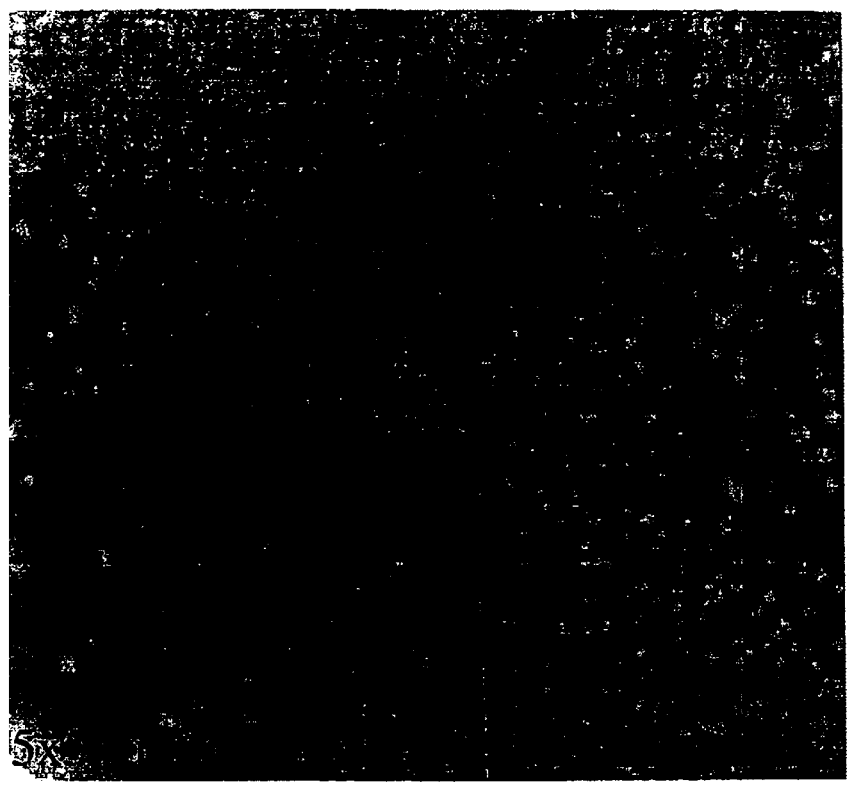
FIG. 10 shows the fluorescence of colonies of induced *E. coli* host cells transformed to co-express P450 and HRP enzymes, in the presence of naphthalene and hydrogen peroxide.
Figure 11A:
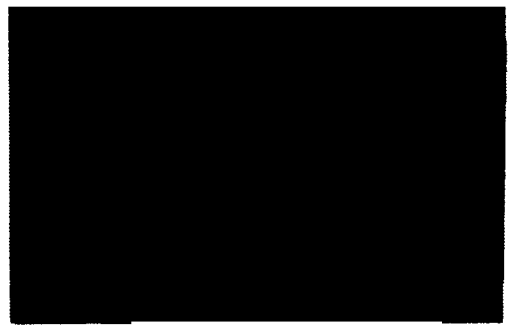
FIGS. 11A-11D show the computer-assisted image analysis of a group of colonies of fluorescent cells in a whole cell P450/HRP assay according to the invention.
Figure 11B:
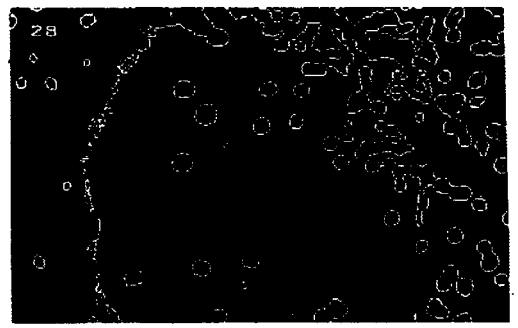
Figure 11C:
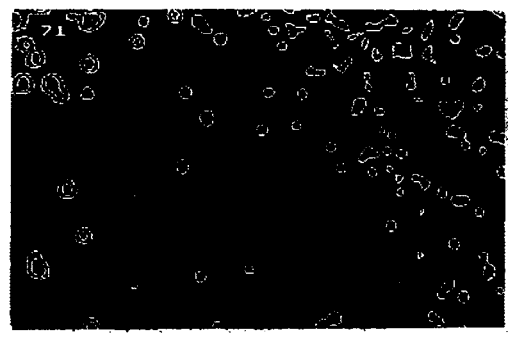
Figure 11D:
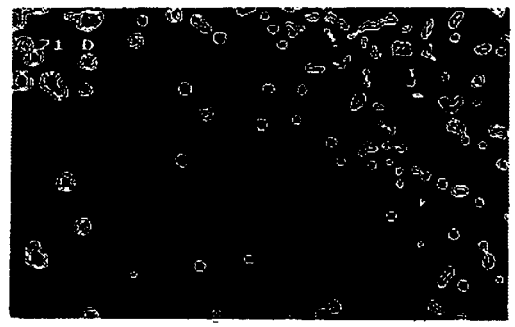

Scanned images (FIG. 10) were further processed by configuring overall thresholding, geometry recognition, intensity quantification, global and local segmentation, and cutting edge to reduce background fluorescence. A main consideration was the separation of the overlapping colonies in the two-dimensional cell fluorescence image. The original fluorescence image scanned was rather complex and involved many unclear edge cuts to analyze (FIG. 11A). By imposing the sequential combinations of Boolean bit-map digitization and by passing through a uniform luminance enhancement algorithm (Extensis, Extensis Co.), the images could be fine-tuned for further evaluation (mainly, cutting edge by volume downsizing, boundary deletion, and dividing) in the OPTIMAS analyzer. See FIGS. 11B-11D. During the second image processing, colonies touching each other were first selected for semi-automatic algorithm provided by this package and then a boundary detection algorithm was run to delete any colonies that hit the boundary. FIG. 11B still exhibits the regions of two or three cells in contact, and FIGS. 11C and 11D show improved fluorescence images after several cycles of processing.

Figure 12A:
Figure 12B:
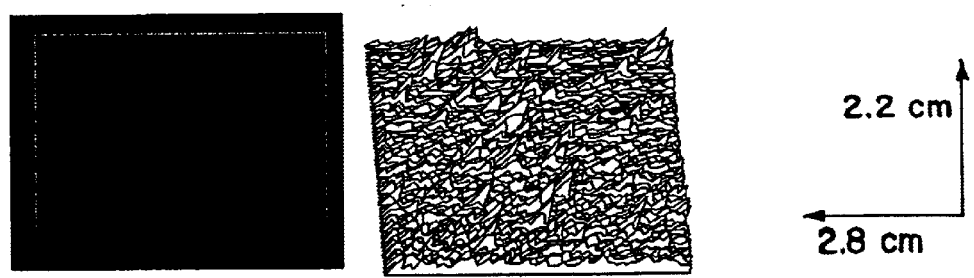

Using these image analysis techniques, FIG. 12 shows a comparison of fluorescence intensities in $E.$ $coli$ BL21(DE3) for the following combinations:

A. P450$_{cam}$/HRP co-expression with addition of naphthalene and $H_2O_2$;

B. P450$_{cam}$ with addition of naphthalene and $H_2O_2$;

C. HRP with addition of naphthalene and $H_2O_2$

D. Untransformed $E.$ $coli$ BL21(DE3) host strain as a negative control;

E. P450$_{cam}$/HRP co-expression with $H_2O_2$ and without naphthalene;

F. P450$_{cam}$/HRP co-expression with naphthalene and without $H_2O_2$.

Left side images are 2-dimensional original fluorescent colonies scanned. The right side histograms, moonscape view, are the resulting fluorescence intensities of the individual colonies.

Co-expression of P450$_{cam}$/HRP (Combination A) gave the highest fluorescence intensity among the cells tested. There was a 3-fold increase of the absolute fluorescence level between the cells harboring P450$_{cam}$/HRP vectors (A) and P450$_{cam}$ expression vector alone (B), as estimated in the moonscape view. Due to the low level of the fluorescence generated, approximately less than one-quarter of the colonies could be counted with the cells harboring only the P450$_{cam}$ expression vector. The background fluorescence levels tested with the other four cases (HRP, BL21(DE3) host strain, and in the presence or absence of naphthalene and $H_2O_2$) were much lower and clearly distinguishable from the fluorescence generated by the co-expression system. Scored fluorescence intensities of these control cases (FIGS. 12C, 12D, 12E, and 12F) almost all fell between 0 to 5. None of these four cases (C, D, E, F) scored a hit during the image analysis. Therefore, cells expressing the oxygenase and peroxidase enzymes can be identified by plate-based image analysis as active in the hydroxylation reaction.

Figures 13A, 13B, 13C:
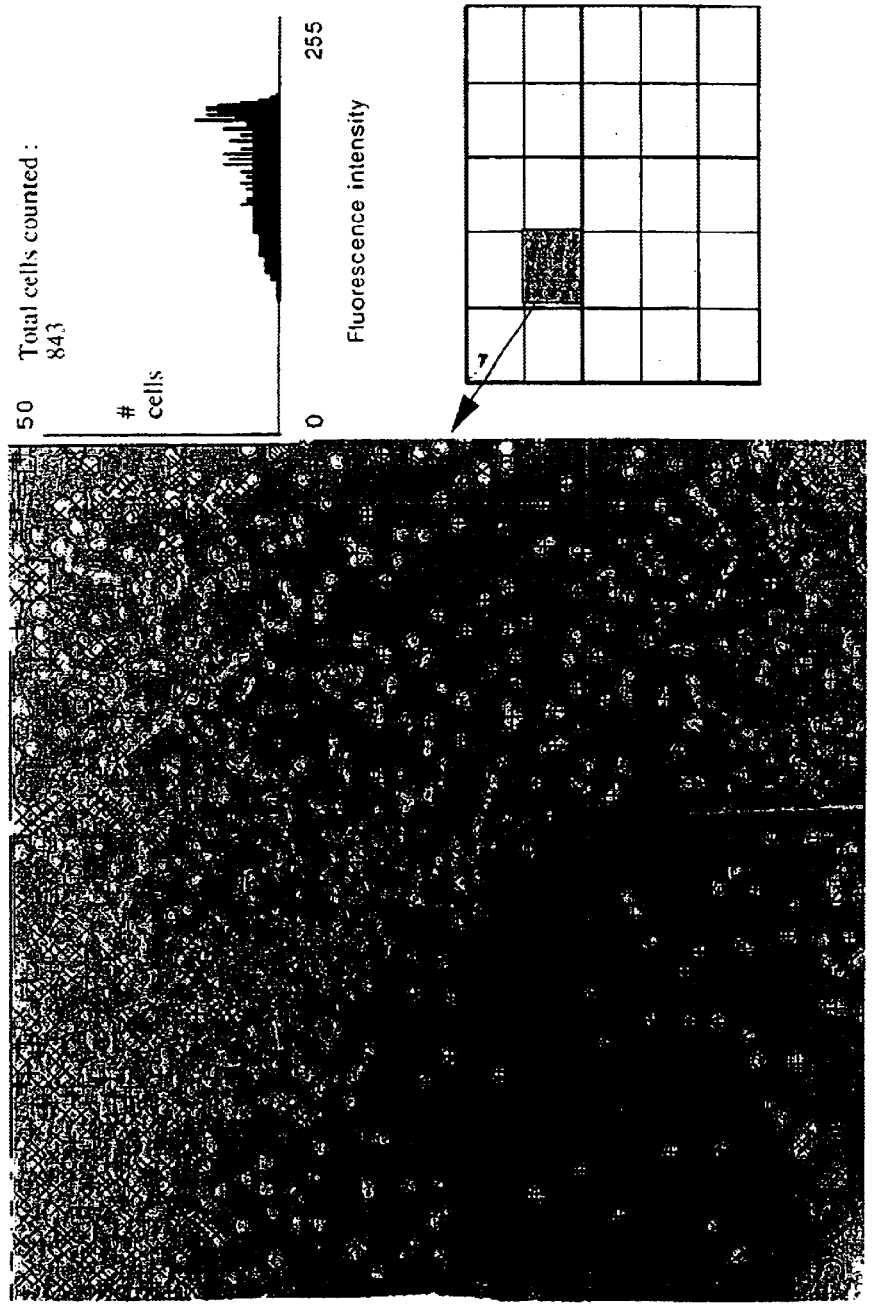
FIG. 13 depicts a method for automatically detecting positive (fluorescent) colonies of whole cells which produce active oxygenase enzyme according to the invention. Colonies of host cells are plated, and the plate is conceptually divided by a grid into rectilinear compartments, each of which can be scanned by conventional image analysis equipment (FIG. 13A). Each compartment is scanned for fluorescent colonies (FIG. 13B) and the number of positive (fluorescent) colonies counted. The fluorescence intensity is also measured (FIG. 13C). Colonies containing improved oxygenases (fluorescence above a certain level) can be identified and selected. This technique can be automated.

FIG. 13 shows a technique for automatically detecting fluorescent colonies and the fluorescence intensity analysis result. A total of 843 cells in a 5×5 sq. cm scanned area were counted (out of 20,000 colonies counted in an entire 25×25 sq. cm plate). The individual positive colony fluorescence intensities could be integrated in the scanned area. The $E.$ $coli$ cells exposed to naphthalene on the plate survived during the 24 hours incubation. The computer-assisted techniques described above may also be used in connection with an automated or high speed embodiment.

The image analysis results are consistent with the data obtained from assays carried out in 96-well plates (see FIG. 8). In these experiments it is shown that the cells having P450$_{cam}$ alone resulted in relatively low fluorescence formation (almost three times lower absolute fluorescence level), as compared to the two-enzyme approach. Even though the naphthols exhibit fluorescence, the intensities estimated were very low at nanomolar concentration levels (200–250 a.u. for 10–100 nmol/ml). Thus, direct whole cell fluorometric observation of the P450$_{cam}$ hydroxylation reaction can be realized, and co-expression with HRP leads to significant advantages for screening.

An important advantage of this enzyme-coupled assay system is that it generates an amplified fluorescence signal proportional to the formation of oxygenated product. This intensified signal allows the screening of large numbers of host cells expressing oxygenase enzymes, for example, by fluorescence digital imaging or by fluorescence activated cell sorting (FACS). The greater the signal amplification provided by the use of the coupling enzyme, the lower the oxygenase activity that can be identified by this screening process. Furthermore, fewer false positives and false negatives will be identified during screening for improved oxygenases.

EXAMPLE 3

Whole Cell Screening for Cytochrome P450 Activity Towards Other Substrates by Image Analysis and Co-expression of P450$_{cam}$ with Horseradish Peroxidase (HRP)

In this example coumarin and 3-phenylpropionate are used as substrates in place of naphthalene. Co-expression of HRP with the P450 monooxygenase leads to fluorescence generation for coumarin and 3-phenylpropionate as substrates of the hydroxylation reactions. All experimental conditions are the same as those described in EXAMPLE 2, except for the substrate concentrations used. The final concentrations of 3-phenylpropionate and coumarin were 1.2 g/l and 6×10$^{-2}$ g/l, respectively.

Coumarin and its hydroxy derivatives, 7-hydroxycoumarin and 4-hydroxycoumarin, were purchased from Sigma Chemical Co. (St. Louis, Mo.). 3-phenylpropionate and its 2-/4-hydroxy derivatives (3-(2-hydroxyphenyl) propionate and 3-(4-hydroxyphenyl) propionate) were also purchased from Aldrich and Sigma Chemical Co. Characteristic hydrocoumarin or hydroxy (3-phenylpropionate) peaks were detected using a fluorimeter with a broad band-path fluorescence emission filter (465+/31 nm); i.e. a Perkin Elmer HTS 7000. The whole cell reaction system using co-expression of P450$_{cam}$ with horseradish peroxidase was used. At pH 9, 4- and 7-hydroxycoumarin also show a characteristic blue-green fluorescence (emission at 450–495 nm; excitation at 350 nm). This fluorescence is hardly detectable, however, because coumarin itself also exhibits quite strong fluorescence, leading to high background fluorescence under these conditions.

Figure 14A:
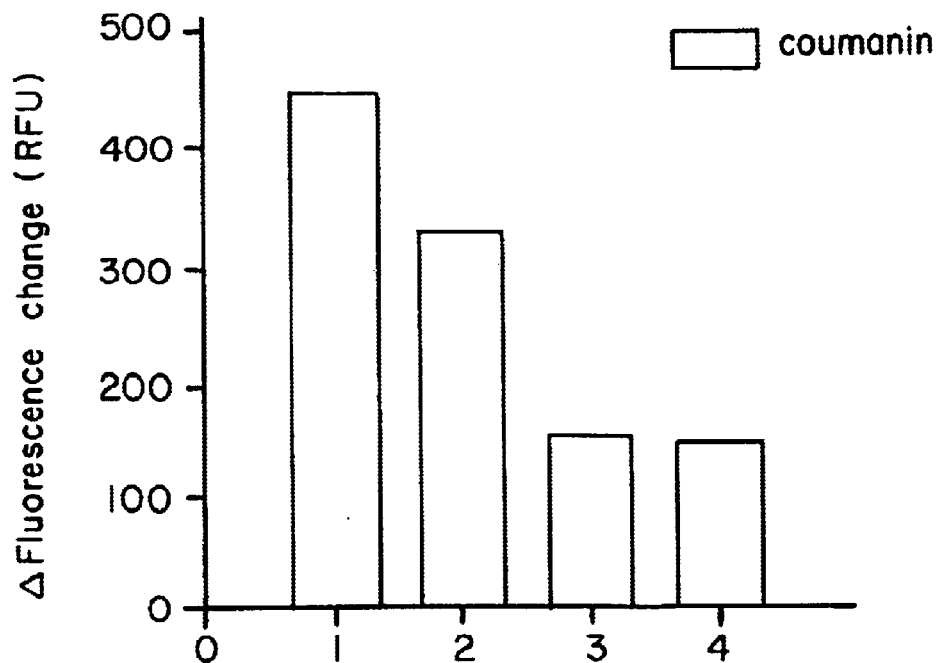
FIG. 14A shows the results of a experiment using coumarin as a substrate for oxygenation, in an assay of the invention.
Figure 14B:
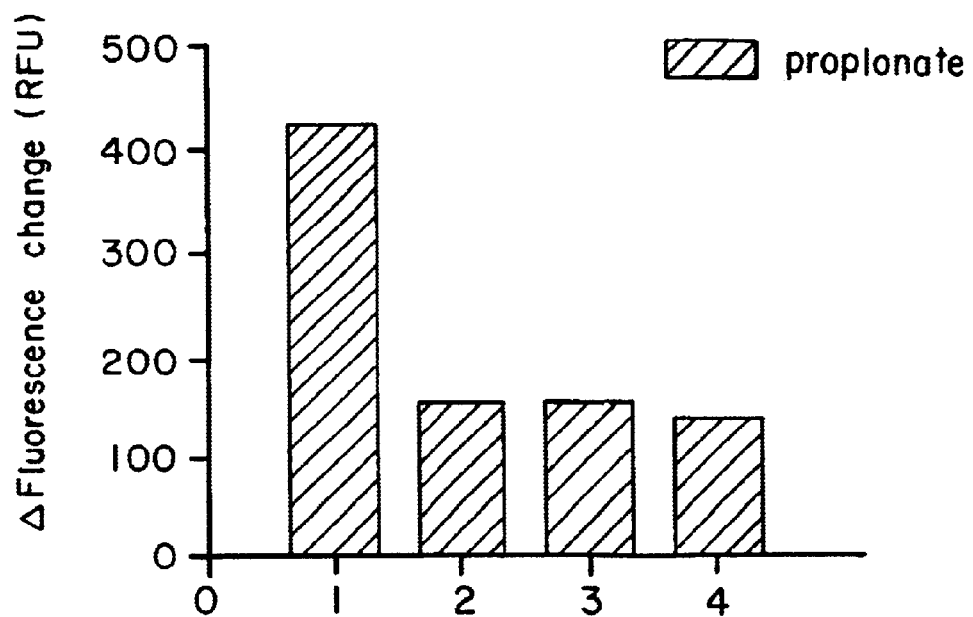
FIG. 14B shows the results of an experiment using 3-phenyl propionate as the substrate.

FIG. 14 shows the results of the HRP-assisted fluorescence intensification for two substrates, coumarin (FIG. 14A) and 3-phenylpropionate (FIG. 14B). Each numbered bar graph shows, respectively, the results of: (1) P450$_{cam}$ and HRP1A6 co-expression in E. coli BL21(DE3) host cells; (2) P450$_{cam}$ expression in E. coli BL21(DE3) host cells; (3) HRP1A6 expression in E. coli BL21(DE3) host cells; and (4) E. coli BL21(DE3) host cells. With coumarin, which is already quite fluorescent, some intensification was found: 35% higher than with the P450$_{cam}$ expression alone. In the case of 3-phenylpropionate, HRP assistance gave 300% higher fluorescence intensity, as compared to the controls (P450$_{cam}$ in BL21(DE3), HRP in BL21(DE3), and the host strain).

EXAMPLE 4

Hydroxylation Assay Based on Chemiluminescence Light Enhancement

This example demonstrates the use of chemiluminescence detection for monitoring the formation of hydroxylated products, using horseradish peroxidase as the coupling enzyme. See FIG. 15. In this example, the coupling enzyme is coexpressed with the oxidation enzyme in bacterial cells, as shown for example in EXAMPLE 2. In a 96 well plate assay, as previously described, the signal afforded by using a P450 monooxygenase and the HRP coupling enzyme was measured (column 4 in FIG. 15A) and compared to the signal from cells that do not have the coupling enzyme (column 5), do not carry out the hydroxylation reaction (column 6) and carry out neither reaction (column 7). Rows E and F contain the substrate (3-phenylpropionate), while rows G and H contain no substrate.

The oxidation of the chemiluminescent agent luminol by peroxidase catalysis leads to a colored product, but generates no (or very weak) chemiluminescence in the presence of just hydrogen peroxide (no coupling enzyme). The photocurrent (intensity) of the generated chemiluminescence light was measured using an AlphaImager system (AlphaImager 2000, ver. 3.3, AlphaImager Corporation). This luminometer includes a multichamber cabinet for luminescence detection (a light-tight box with a matte-black interior), photocurrent analysis software (AlphaImager 2000, ver. 3.3), and a CCD detector for light intensity detection. Light emitted from individual wells of a 96-well type white "Nunc" fluoroplate was measured in the camera luminometer.

Luminol was purchased from Molecular Probes (Eugene, Oreg.), and 3-phenylpropionate and 30% hydrogen peroxide were purchased from Sigma. The reaction mixture (200 ul) contained 0.1 mM borate buffer 8.6 with sodium perborate (3 mM), luminol (60 and 120 uM), and 3-phenylpropionate (0.5 mM). Cell growth and P450$_{cam}$/HRP co-expression conditions are the same as in EXAMPLE 2. After the 24 hour induction to produce the P450$_{cam}$, hydroxylation of 3-phenylpropionate was carried out for 20 min. The hydroxylation reaction conditions are as described in EXAMPLE 2. Hydrogen peroxide (5 mM) was added.

Figure 15A:
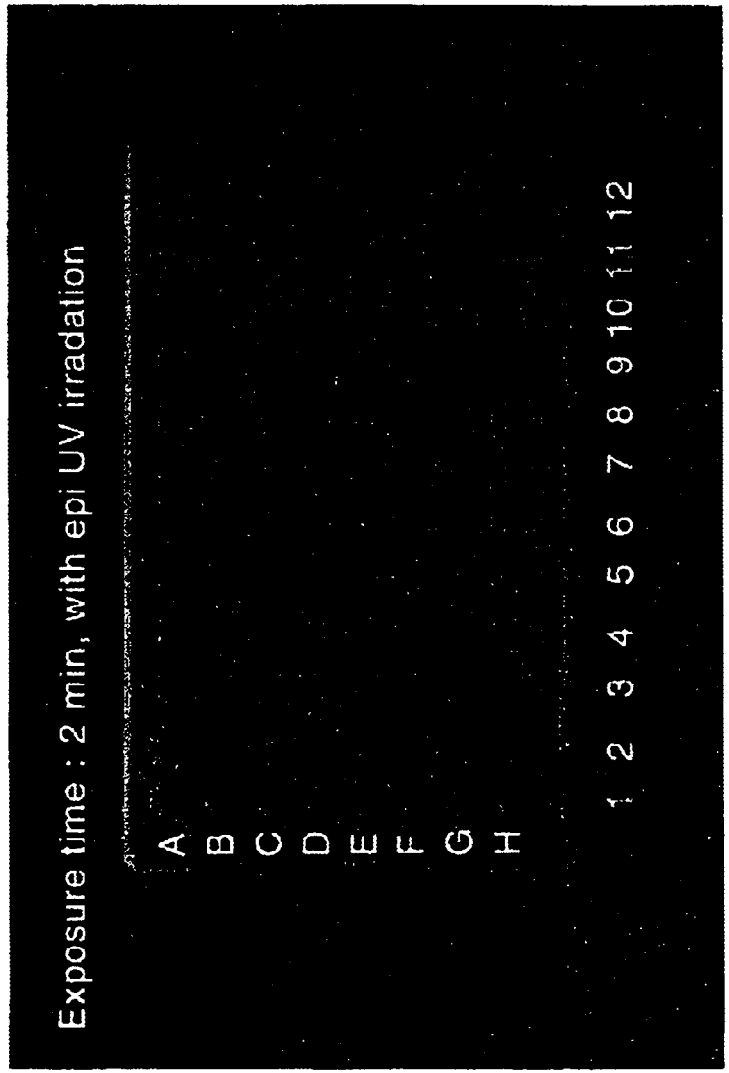
FIG. 15 shows a 96 well plate assay according to the invention, in which the fluorescence of 3-phenyl propionate substrate oxygenated and polymerized in an *E. coli* P450/HRP co-expression whole cell system is amplified using luminol. A comparison is shown with a host cell control, and with cells transformed to express P450 enzyme without HRP and HRP enzyme without P450. Results using ultraviolet (UV) irradiation are shown in FIG. 15A. Results without irradiation are shown in FIG. 15B.

Reaction conditions and results are shown in FIG. 15. The luminescence measurements show that the P450cam-catalyzed hydroxylation of the 3-phenylpropionate enhances the luminescence light generation. The chemiluminescence of the cells containing expressed P450cam and HRP (Lane 4, Row F of FIG. 15B) was enhanced up to 98-fold, as compared to the luminol reaction itself (Lane 4, Rows G and H). The hydroxylated 3-phenylpropionate therefore leads to a significant increase in the light emission and can be monitored using this approach. The integrated light emission of the strain coexpressing both enzymes shows more than 1000-fold increase in the first 40 seconds after the reaction is initiated, as compared to other background levels. The intense and prolonged light emission from the reaction enhanced by the incorporation of the additional hydroxylated aromatic phenol lasted more than 7 minutes. This is particularly useful for the screening of enzymes with relatively weak hydroxylation activities, for example in connection with particular substrates. Moreover, multiple colonies can be assayed rapidly and simultaneously by using colony image analysis. The abbreviation "ILDV" (e.g. FIG. 15B) indicates the integrated light density value, as a chemiluminescence intensity unit. The results in epi UV conditions show that the 3-phenylpropionate hydroxylation can also be detected using the combined forms of light intensities (a kind of light energy amplification), which were generated by chemiluminescence and fluorescence-like light emission, separately (FIG. 15A). Although the absolute light density was increased, in this case, the dual mode detection gained increased background.

EXAMPLE 5

Monitoring Oxidation by Co-expression with Cytochrome c Peroxidase

This example demonstrates the use of another peroxidase, cytochrome c peroxidase (CCP), a gene from yeast that is expressed in E. coli as the coupling enzyme for screening P450$_{cam}$-catalyzed hydroxylation. The yeast CCP enzyme is expressed in functional form in E. coli host cells.

A. Cytochrome c Peroxidase Vector Construction

Figure 16:
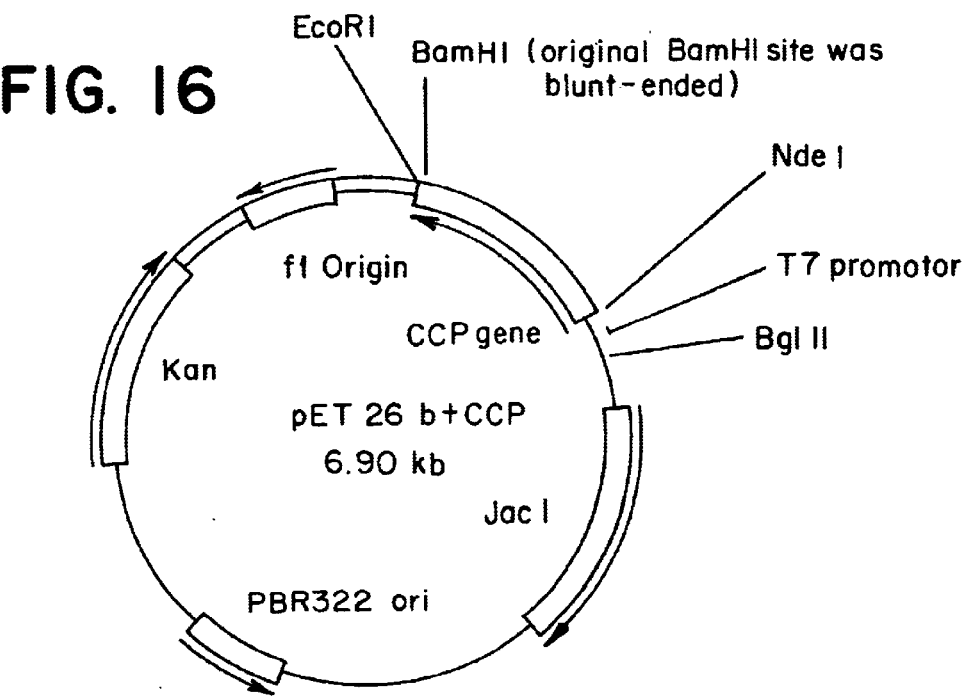
FIG. 16 shows the yeast cytochrome c peroxidase (CCP) expression vector pet-26b(+)CCP.

The S. cerevisiae cytochrome c peroxidase (CCP) gene from pT7CCP (donated by Dr. David Goodin, The Scripps Research Institute, La Jolla, Calif.) was recloned into Nde I and Bam HI sites of kanamycin resistant pET-26b(+) expression vector (purchased from Novagen, Inc., Madison. Wis.). pT7CCP carries a gene for CCP in which the N-terminal sequence has been modified to code for amino acids Met-Lys-Thr, as described in Goodin et al. (1990) (39), and Fitzgerald et al. (40). First, the pT7CCP vector containing the CCP gene was linearized with Pvu II, blunt-ended with Mung-bean nuclease to give a ligation site between the 3'-end of this gene and the Bam HI site in pET-26b(+). Next, this gene fragment was cut using Nde I for 5'-end ligation with the vector. The N-terminal pelB signal sequence which is located in the upstream region (224–289) of the pET-26b (+) vector was removed by Nde I and BamH I digestion, to allow intracellular CCP expression. Bam H I cut was then blunt-ended for further ligation with the engineered CCP gene fragment. FIG. 16 shows the pET26 b+CCP vector map.

B. Whole Cell Screening for Cytochrome P450 Activity Using CCP Co-expression

Figure 17:
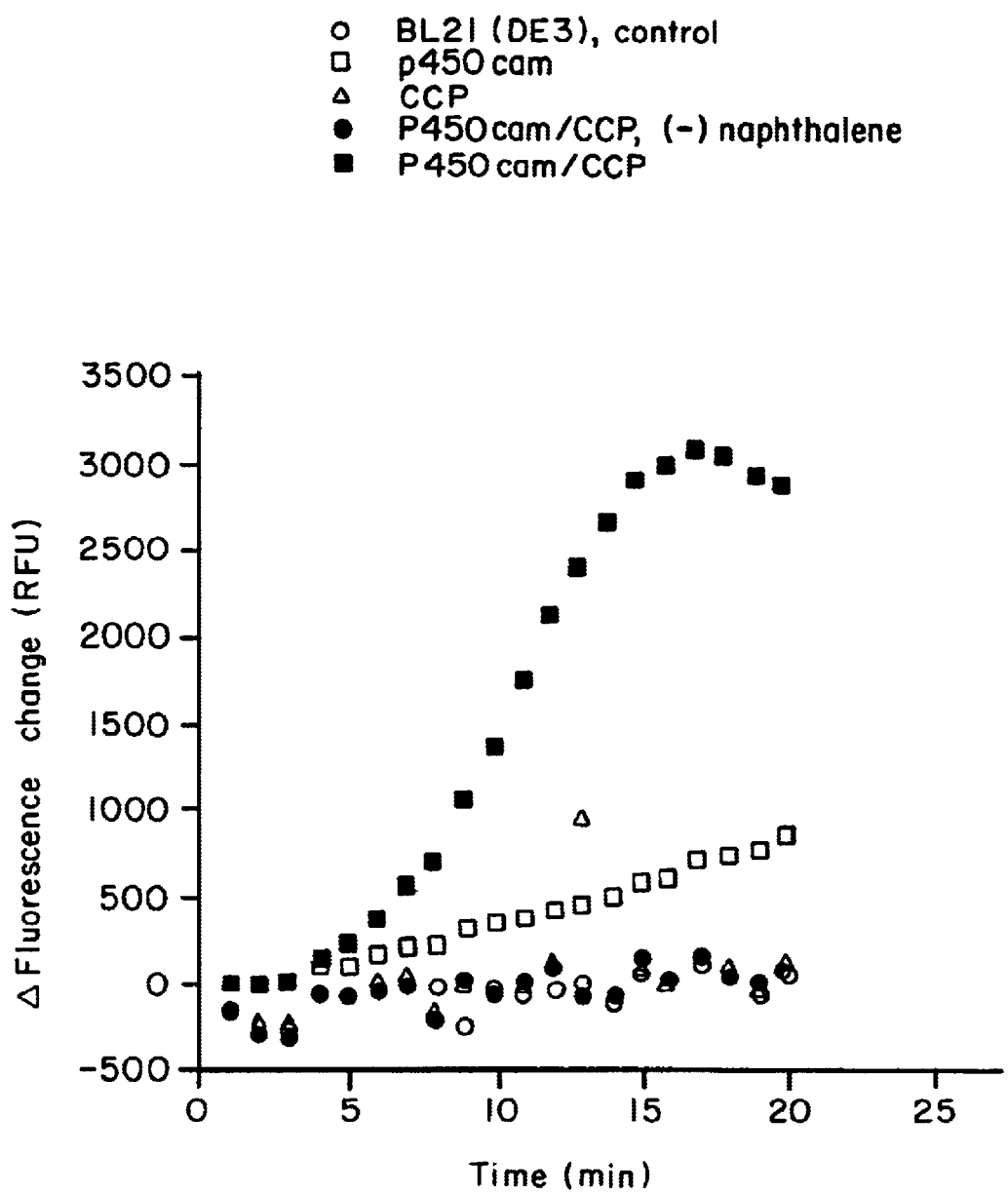
FIG. 17 shows the detection of fluorescence in an embodiment of the invention in which cytochrome c peroxidase (CCP) is used as a coupling enzyme that is co-expressed with P450 enzyme in a whole cell system. Comparisons with an *E. coli* host cell control, without substrate, and with cells transformed to express CCP without P450 and P450 without CCP are also shown.

Expression was undertaken with E. coli BL21(DE3) cells transformed with pCWori(+)_P450$_{cam}$ and pET26 b+CCP vectors, as previously described. The plasmid backbone of pET-26b(+) contains a T7 promoter at 361-377 region, f1 plasmid, and a kanamycin coding region. Cell growth and assay conditions are the same as EXAMPLE 2 except for inducer and kanamycin concentrations. For the co-expression of both enzymes, P450$_{cam}$ and CCP, 1 mM IPTG and 50 ug/ml kanamycin were used. The results are shown in FIG. 17. Co-expression of P450cam/CCP gave highly intensified fluorescence signals when naphthalene hydroxylation was tested. A 3.2-fold increase of the absolute fluorescence level, as compared to P450cam catalyzed reaction alone, was observed.

EXAMPLE 6

Use of Laccase as Coupling Enzyme

In this example, a laccase enzyme was used as a coupling enzyme, instead of a peroxidase. When a laccase is used, there is no need to add hydrogen peroxide, as this enzyme can catalyze the oxidative coupling reaction using molecular oxygen. This is useful when screening oxidative enzymes that do not require peroxide for the reaction.

Laccases are copper-containing enzymes that catalyze the oxidation of a variety of substrates, such as phenols, mono-, di-, and poly-phenols, methoxy-substituted phenols, and aromatic amines. Laccases couple four of these one-electron oxidations to the irreversible four-electron reduction of dioxygen to water. Each one-electron reaction generates a free radical. Aryloxy radicals formed by laccases are unstable and typically undergo a second reaction. This reaction may be a second enzymatic oxidation (converting phenol to quinone in many cases), a nonenzymatic reaction such as hydration, disproportionation, or oxidation/reduction, or the radical may couple to other phenolic structures in a polymerization reaction that produces products that are often colored and/or highly fluorescent.

Laccase was purchased from Sigma Chemicals as a crude acetone powder from the fungus Rhus vernificera. The laccase powder had a minimum of 50 units per mg., with unit activity defined as) A$_{530}$ of 0.001/min. at pH 6.5, 30° C., 3 mL solution with syringaldazine as substrate. Type II HRP (RZ approximately 2.0) and all other chemicals were purchased from Sigma. Fluorescence readings were taken with a Perkin-Elmer HTS 7000 plate reading fluorimeter. Excitation and emission wavelengths were 360 nm and 465 nm, respectively.

Experiments were performed at 25° C. in the wells of opaque, white Nunc 96-well plates with a total liquid of 200 uL. Except where stated otherwise, each well contained 10% pure ethanol to improve the solubility of substrates and products. Where HRP was used for comparison, approximately 2.3 units of HRP and 5 mM H$_2$O$_2$ were in each well. Each experiment was performed at pH values of 6.5, 7.5, and 9.0 using phosphate buffers (10 mM and 100 mM, depending on the experiment), which shows no fluorescence. Tris buffer was not used because it increases background fluorescence. Except where stated, results are given from conditions at pH 9.0, which were either the best results or barely distinguishable from the other conditions.

In order to evaluate laccase in a useful whole cell assay to identify the formation of hydroxylated aromatic compounds by oxidative enzymes (such as cytochrome P450$_{cam}$ and toluene dioxygenase), laccase was added to solutions containing cells, naphthalene, and naphthol. P450$_{cam}$ was expressed in E. coli strain BL21(DE3) using plasmid pCWori+. BL21(DE3) cells with and without the expressed protein were grown in Terrific Broth and after 8 hours were induced with 1 mM IPTG for 24 hours. 50 μL of each type of cell solution (with or without plasmid) was added to twelve wells (six wells for each type). pH 9 buffer was added to each well so that the final volume after all additions would be 200 uL. Approximately 15 units of laccase was added to each well, and the mixtures were allowed to pre-incubate for about 45 minutes to remove any high background activity between laccase and cell solution components. In one set of six wells, three with plasmid-harboring cells and three with non-transformed cells, 10 μL of naphthalene saturated in ethanol was added to each solution. 1-Naphthol was then added to one of each type of well (with and without naphthalene; and with and without P450$_{cam}$) to a concentration of 100 uM. Similarly, 2-naphthol was added to four other wells. These wells in which naphthol was added (in addition to naphthalene) simulate situations in which P450$_{cam}$ is capable of producing naphthol from naphthalene at high concentrations (100 uM). All wells contained 10% ethanol. For comparison, the same twelve wells were prepared using HRP and H$_2$O$_2$ instead of laccase. These same experiments were performed at pH 6.5.

In all wells containing 1-naphthol (100 uM) and either HRP or laccase a color change from the light yellow of the cell solution to a dark brown color occurred. The change was more rapid with HRP (approximately 1 minute compared to approximately 1 hour). In the case of 2-naphthol, color change to a light orange occurs, although this is less pronounced and slower. The difference in color formation between comparable solutions may produce stronger color changes, in theory because the HRP preparation itself already has a slightly brown color. It is relatively difficult to discern a difference in color between the comparable solutions with and without naphthalene added or with and without P450 expression, indicating that the level of naphthalene hydroxylation by the enzyme is very low at the expression level in this experiment, and in its activity towards this substrate under the test conditions. No color change was observed for any of the wells not containing naphthol. These results indicate that as long as naphthol is produced in a high enough concentration by the hydroxylating enzyme, laccase can be used as a coupling enzyme for naphthol identification in a colorimetric whole cell assay.

EXAMPLE 7

Detection of Catechols Formed by Toluene Dioxygenase (TDO)-Catalyzed Dioxygenation of a Substituted Benzene This example demonstrates the use of horseradish peroxidase for detecting the formation of the products (catechols) of TDO-catalyzed dioxygenation of chlorobenzene followed by dehydrogenation. A host cell, *E. coli* in this example, is transformed with a vector having a functional TDO gene, and transformed cells are grown under conditions suitable for TDO expression. Host cells in this example are also transformed to express the enzyme dihydrodiol dehydrogenase, and they may be transformed to express HRP, as described in other EXAMPLES herein.

The overall reaction used in the assay of this example is shown below.

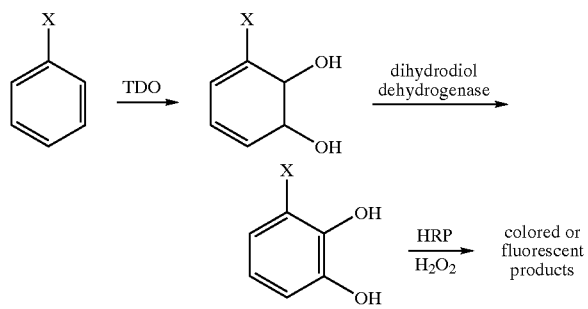

Figure 18:
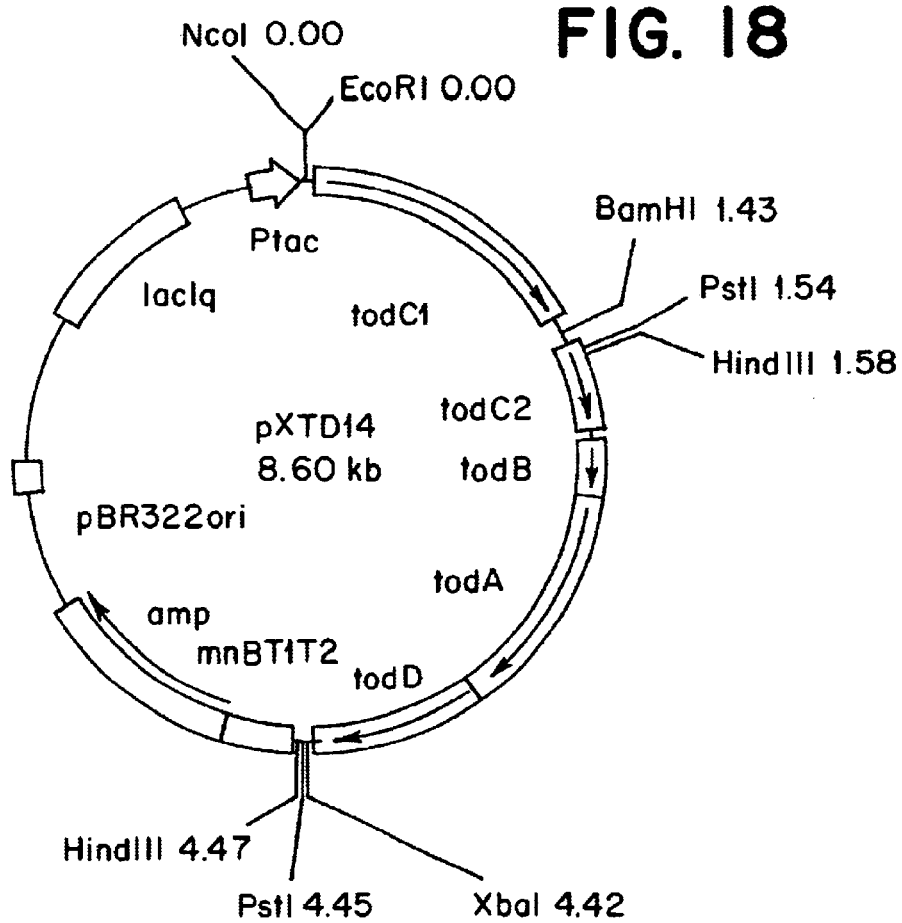
FIG. 18 shows the toluene dioxygenase (TDO) expression vector pXTD14.

The first set of reactions (catechol formation) is catalyzed by *E. coli* DH5 alpha containing plasmid pXTD14, which contains the genes todC1C2BA (for toluene dioxygenase) and todD (for dihydrodiol dehydrogenase). A map of this construct is shown in FIG. 18.

For plasmid construction, *E. coli* DH5 alpha was used as a host and the transformants were grown in LB containing 50 μg/ml ampicillin at 37° C. The *E. coli* expression vector pTrc99A was purchased from Pharmacia Biotech (Uppsala, Sweden).

A 2.1 kb wild type todC1-todC2 fragment was produced by PCR on template pDTG601 (provided by D. Gibson, University of Iowa) (41), using the following primers:

a forward primer TDO-5F: 5'-GA TCATGAATGAGACCGACACATCACCTATC-3' [SEQ. ID. NO. 3]; and a reverse primer TDO-2R: 5'-AC GAATTCTAGAAGAAGAAACTGAGGTTATTG-3' [SEQ. ID. NO. 4]. The fragment was digested with BspHI and EcoRI and subcloned in NcoI-EcoRI site of pTrc99A to construct pXTD2. Restriction sites in the primers are underlined.

A DNA fragment containing todC2-todB-todA-todD genes was amplified from pDTG602 (provided by D. Gibson, University of Iowa) (41) by PCR using the following primers:

a Bam HI-tagged forward primer TDO-9F (Bam HI restriction sequence is underlined), (5'-TT GGATCCGGTGGACCTTGTCCATTTG-3' [SEQ. ID. NO. 5]; and a reverse primer TDO-14R (Xba I restriction sequence is underlined) (5'-GCTCTAGATCAACCGAAGTGCTTG TCGAG-3' [SEQ. ID. NO. 6].

The resulting 3.0 kb fragment was digested with Bam HI and Xha I, and purified by QIAquick PCR Purification Kit (QIAGEN). This fragment was cloned in Bam HI-Xba I site of pTrc99A to yield plasmid pXD10. Then pXTD10 was digested with EcoRI and BamHI and ligated to a 1.2 kb wildtype todC1 fragment digested with EcoRI and BamHI. This wild type todC1 fragment was produced by PCR using:

a forward primer TDO-12F: 5'-CG GAATTCTAGGAAACAGACCATG-3' [SEQ. ID. NO. 7]; and a reverse primer TDO-13R: 5'-CC GGATCCAACCTGGGTCGAAGTCAAATG-3' [SEQ. ID. NO. 8] from template DNA pXTD2. Restriction sites in the plasmids are underlined. The resulting plasmid is pXTD14. *E. coli* strain DH5 alpha transformed with pKK223-3 (Amersham Pharmacia Biotech, Uppsala, Sweden) was used as a control.

In this example, a chlorobenzene substrate is oxygenated by the addition of two hydroxyl groups, via TDO, and the ring structure of the substrate is stabilized to a double bond via dihydrodiol dehydrogenase. The oxygen donor in this reaction is molecular oxygen ($O_2$), obtained by the *E. coli* host from $O_2$ dissolved in the medium. In another reaction, the dihydroxylated product is reacted in the presence of HRP and hydrogen peroxide, to form colored or fluorescent products. Thus, in this example, the substrate is chlorobenzene (or any suitable aromatic substrate), the oxidation enzyme is toluene dioxygenase (TDO), the oxygen donor is molecular oxygen, and the coupling enzyme is horseradish peroxidase (HRP).

The following procedure was used to prepare supernatant containing TDO-produced catechol:

1) Add 0.5 μL of each overnight seed culture to two flasks containing 20 mL of LB-Amp and shake for three hours at 37° C.

2) Add 200 μL of 100 mM IPTG to each flask, and shake at 30° C. for two hours.

3) Centrifuge the cultures at 3000 rpm for 10 minutes and discard the supernatant.

4) Resuspend the pellet in 4 mL of 50 mM phosphate buffer, pH 7.4, containing 10 mM chlorobenzene and 0.2% glucose.

5) Incubate at 30° C. for two hours (2 mL in 15 mL tube).

6) Add 12 mL of 50 mM phosphate buffer, pH 7.4, and centrifuge at 3000 rpm for 10 minutes.

7) Transfer catechol-containing supernatant to a fresh tube.

To detect the catechol products, 10 μL of 2 mg/mL HRP and 10 μL of 1 M $H_2O_2$ was added to 200 μL of supernatant. A two times dilution of the supernatant was also analyzed. In the case of *E. coli* containing pXTD14, the solution turned red shortly after addition of HRP and $H_2O_2$ to the catechol-containing supernatant. The 2x dilutions were subjected to spectro-photometric analysis. The baseline was taken to be the control cultures (pKK223-3) supernatant with only $H_2O_2$ added. The absorbance profile of the pKK223-3 with HRP and $H_2O_2$ was essentially flat. The absorbance profile of the TDO-expressing strain (pXTD14) showed a small peak at 281.5 nm which, on the basis of previous experiments, corresponds to the presence of chlorocatechol. When HRP was added to the supernatant from pXTD14, absorbances appeared around 340 nm and 500 nm that correspond to the polymers formed when the chlorocatechol is oligomerized by HRP.

EXAMPLE 8

Identification of Improved Mutants of $P450_{cam}$

An important aspect of this invention is to identify mutants in a high throughput screen of mutagenized gene libraries. A screening strategy with high throughput fluorescence image analysis has been implemented, in order to identify bacterial clones expressing improved hydroxylating enzymes. Mutants of P450$_{cam}$ with improved activity on naphthalene and hydrogen peroxide (peroxide shunt pathway) have been identified. These mutants are also more active on a related substrate, 3-phenylpropionate.

In general, the method uses polymerase chain reaction (PCR) techniques to generate a library of oxygenase mutants, using DNA sequences (e.g. as primers and/or probes) from a known or starting enzyme as a template. In this example, mutants of P450$_{cam}$ were derived from the P450$_{cam}$ gene discussed above.

A. P450cam Gene Mutagenesis

The mutagenic PCR protocol of Cadwell and Joyce (1992) (15) was used with some modifications. For a 100 µl reaction, the following were included:

10 µl 10×buffer (Boehringer Mannheim, Germany; PCR reaction buffer)
100 mM Tris/HCl, 500 mM KCl, pH 8.3 at 20° C.)
28 µl MgCl$_2$ (25 mM stock solution)
0.2 µl dATP (100 mM stock)
0.2 µl dGTP (100 mM stock)
2 µl dCTP (100 mM stock)
1 µl dTTP (100 mM stock)
0.7 mM MnCl$_2$
1.5 µl forward primer (9.8 pmol/ul)
1 µl reverse primer (14.0 pmol/ul)
1 ul (5 unit) Taq polymerase (Boehringer Mannheim)
0.01% gelatin (from 10×stock)
20 fmoles of template pCWori(+)_P450$_{cam}$
42.1 µl ddH$_2$O.

Error-prone PCR was performed in a programmable thermocycler (PTC200, MJ Research) for 30 cycles. (denaturation 94° C., 30 s; annealing 45° C., 30 s; elongation 72° C., 2 min). The forward (24-mers) and reverse primer (25-mers) sequences used were:

5'-CATCGATGCTTAGGAGGTCATATG-3', [SEQ. ID. NO. 9]

and

5'-TCATGTTTGACAGCTTATCATCGAT-3', [SEQ. ID. NO. 10]

where the Nde I restriction site is underlined. The total insert gene size to be amplified between two primers is 1.4 kb.

B. DNA Purification Cloning and Expression

The Qiaex II kit (Qaigen, Germany) was used for PCR product purification. Purified PCR product was redissolved in TE buffer (10 mM Tris-HCl, pH 8.0) and was subjected to electrophoresis on preparative 1% agarose gels to check the purity. After digestion with Nde I(10 u) and Hind III (10 u) for 2 hours at 37° C., the Nde I-Hind III fragment was purified again by gel extraction and was inserted into pCWori+ shuttle vector. The ligation was carried out at 16° C. for 9 hours with 200 U of T4 DNA ligase (Boehringer Mannheim). The ligation mixture was then used to transform *E. coli* BL21(DE3) Gold cells (Stratagene) which also have pETpelBHRP1A6Kan introduced as described in other examples herein.

For selection of the cells containing two different plasmids, a TB/amp(100 ug/ml)/kan(30 ug/ml) plate was used for cell growth and simultaneous protein expression. The *E. coli* strain containing pCWori(+)_P450$_{cam}$ and pETpelBHRP1A6Kan was grown at 37° C. for 6 hours, then was induced for P450$_{cam}$ and HRP expression by shifting the incubation temperature to 30° C. After 16 hours, the colonies were stamped onto nitrocellulose membranes and transferred onto fresh plates containing naphthalene and hydrogen peroxide for fluorescence image analysis, using the protocol of EXAMPLE 2.

C. Results of Screening for Mutant P450 Activity in a Whole Cell System

Approximately 55,000 mutant P450$_{cam}$ clones on 3 Q-bot plates were screened on naphthalene as a substrate using fluorescence digital imaging. Selected highly fluorogenic mutant colonies identified by digital imaging were transferred to a 96-well plate for confirmation by more detailed measurements, as described in EXAMPLE 2.

Figure 19A:
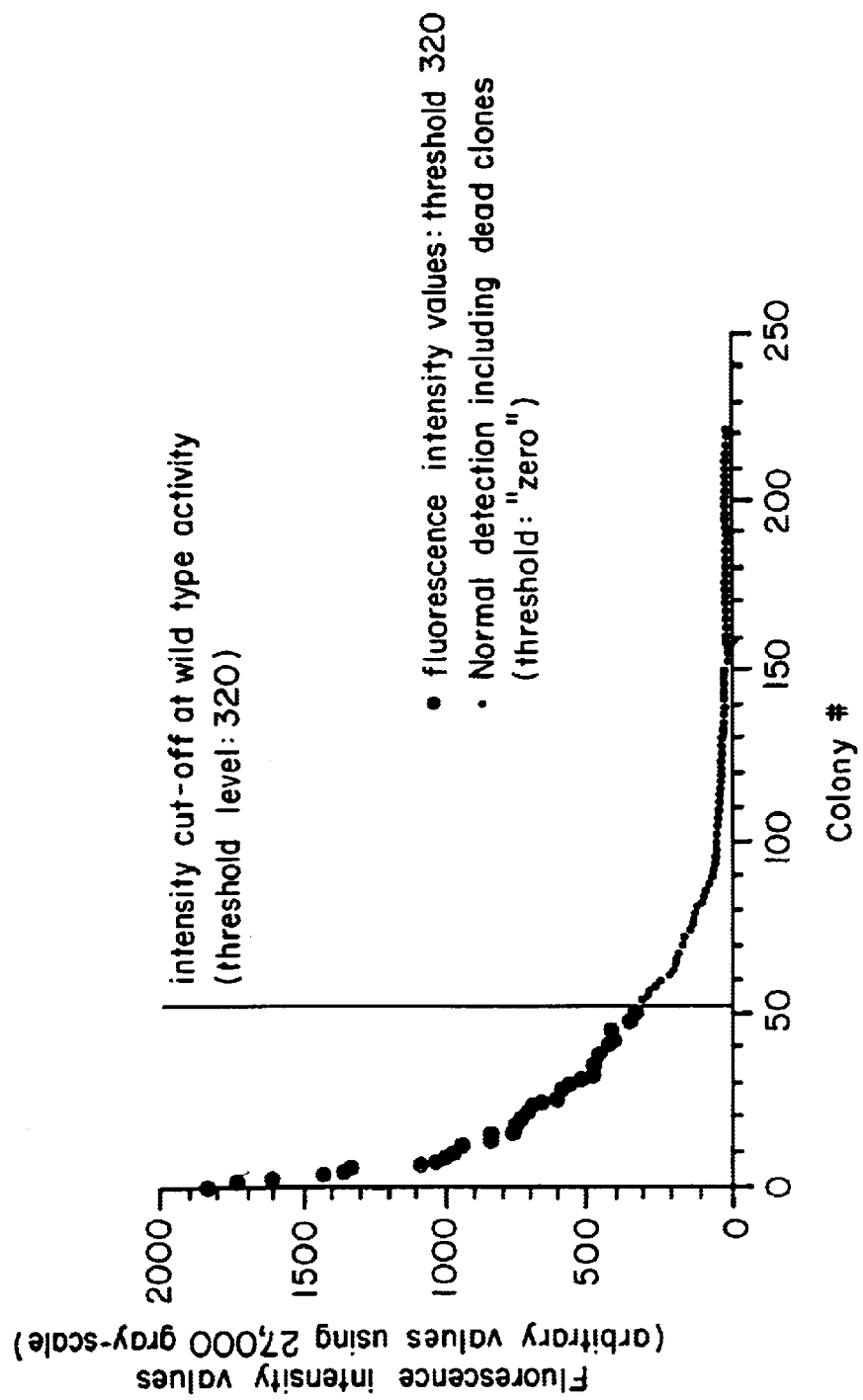
FIG. 19A shows the results of a digital scan of a section of a plate containing fluorescent mutant $P450_{cam}$ colonies.

FIG. 19A shows the results of a digital scan of sections of plates containing fluorescent mutant P450$_{cam}$ colonies. The colony fluorescence values are plotted in descending order. Adjusting the threshold level to the point where the wild type fluorescence is near or lower than the detection limit allows one to see (count) only the colonies expressing P450$_{cam}$ activity comparable to or greater than wild type levels. This demonstrates one of the advantages of using imaging methods in screening, as compared to, for example, assays in microtitre plates. In the microtitre plates inactive or poorly active clones must be counted (measured) alongside active ones.

A large number of the colonies (~20%) show activity roughly comparable to or higher than wild type P450$_{cam}$ activity. The wild type level is ~320 fluorescence units. The highest mutant activity showed 1830 fluorescence units, a nearly six-fold increase in fluorescence.

Figure 19B:
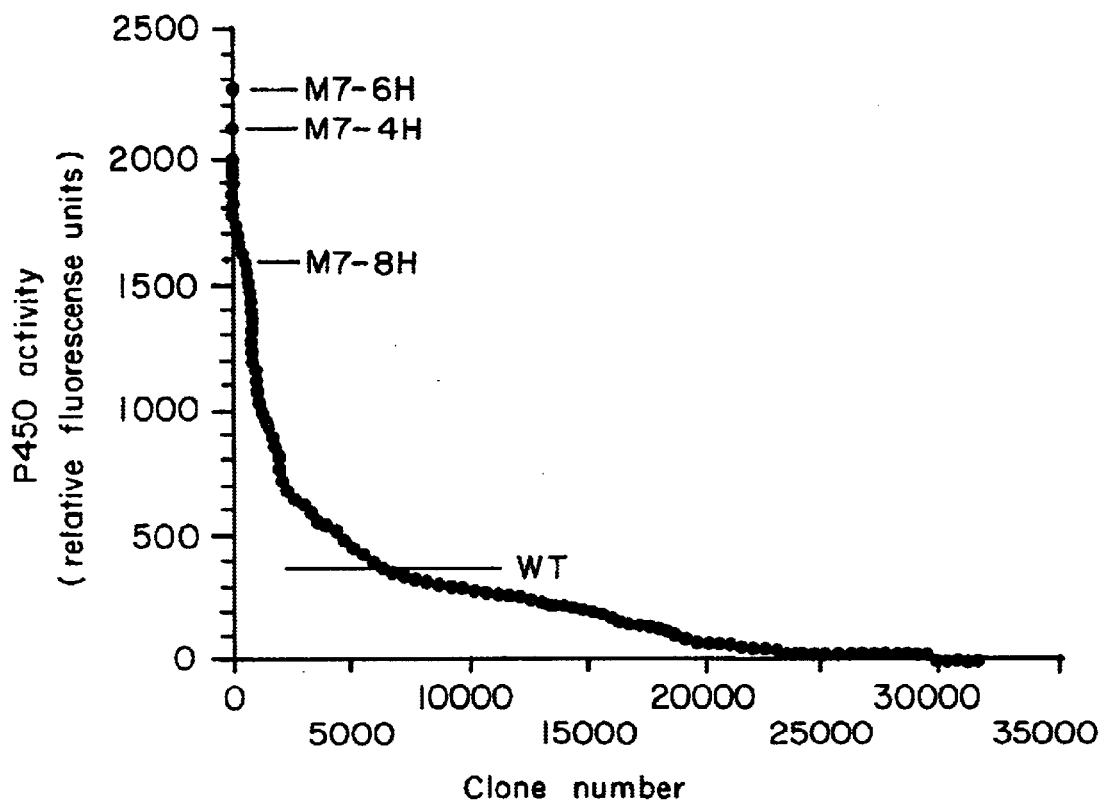
FIG. 19B shows the results of ~32,000 clones from a digital scan of ~200,000 clones from plates containing mutant $P450_{cam}$ colonies.
Figure 19C:
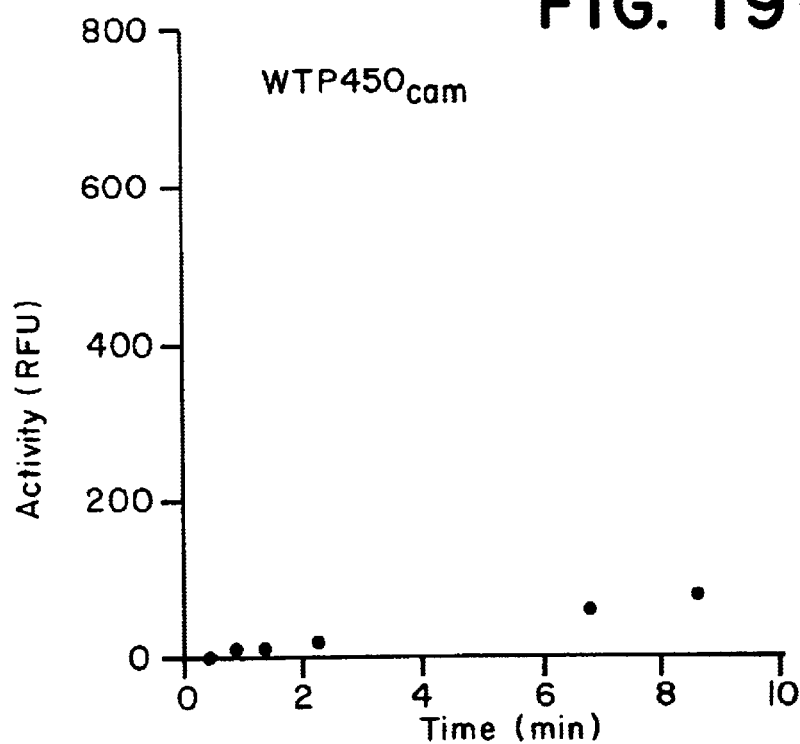
FIGS. 19C-19F shows a graphical representation of the P450 enzyme activities of a sample of mutant $P450_{cam}$ colonies as measured by fluorescence, in an assay of the invention.
Figure 19D:
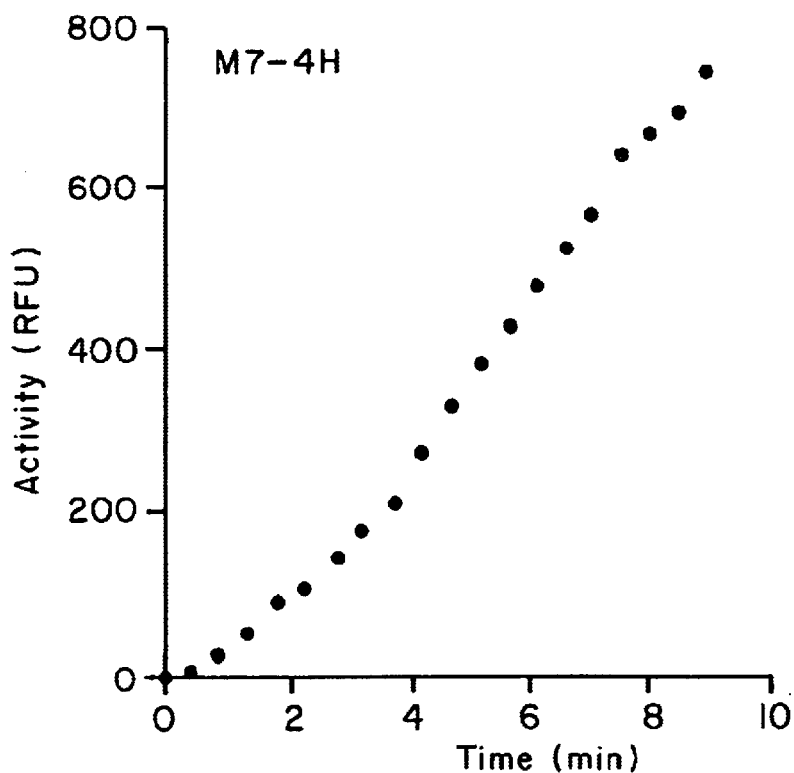
Figure 19E:
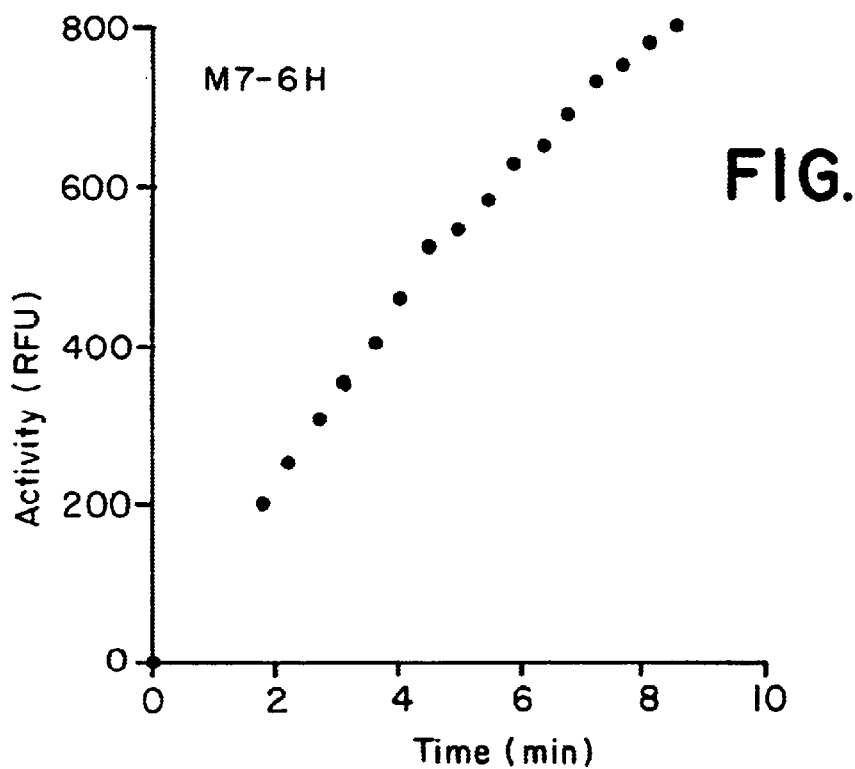
Figure 19F:
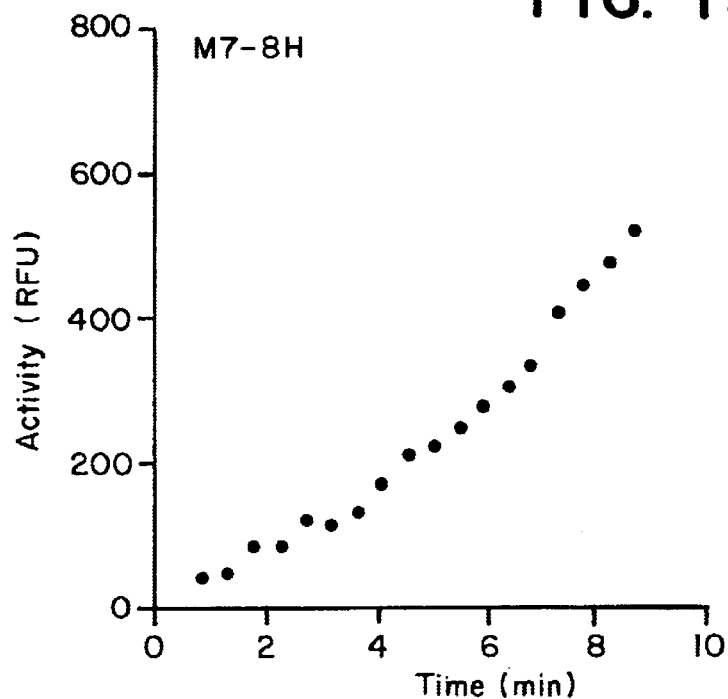

FIG. 19B shows the results of scanning ~200,000 mutants. Fluorescence values of ~32,000 of the clones are plotted in descending order. Three mutants having a high activity compared to wild-type P450$_{cam}$ are indicated. These three clones with enhanced fluorescence were selected for growth and confirmation of the enhanced activity towards naphthalene in a whole cell assay. The fluorescence over time of each of these three mutants and wild-type is shown in FIGS. 19C (wild-type), 19D (Mutant M7-4H), 19E (M7-6H), and 19F (M7-8H). Clone M7-6H showed an 11-fold increase in activity as compared to wild type P450cam. Two other clones (M7-4H and M7-8H) identified by the digital image scanning also showed improved activity on this substrate, with the largest increase of 3.2 fold for M7-6H.

Figure 20:
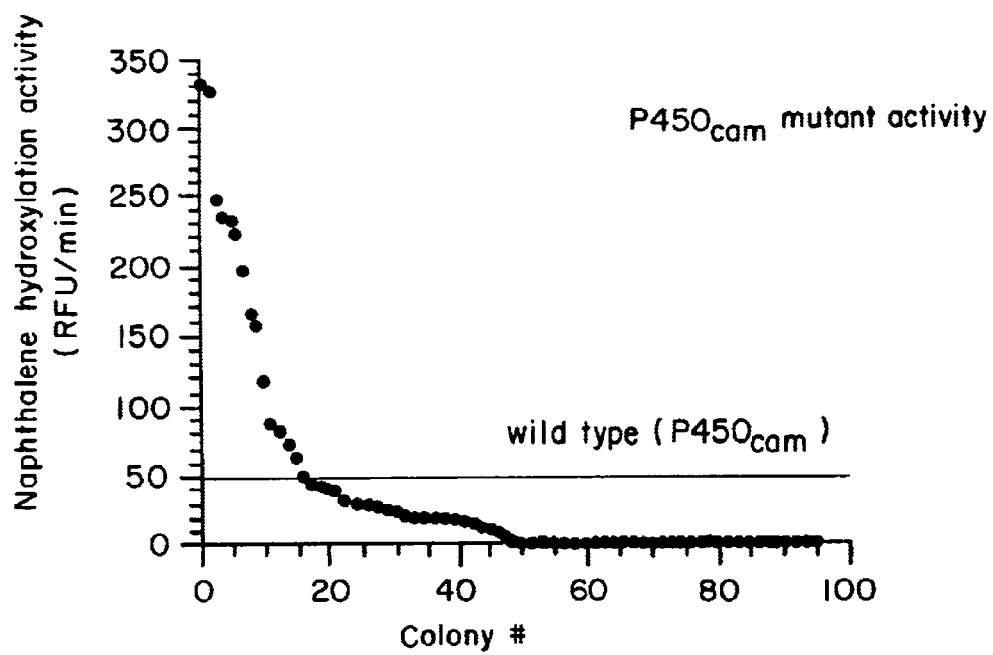
FIG. 20 shows the results of measuring the fluorescence of 96 randomly selected clones from the large mutant library (~20,000 colonies) in a screen according to the invention.

For comparison, 96 randomly selected clones from a large mutant library (~20,000 colonies) were assayed in a 96-well fluorescence microplate reader (HTS 7000, Perkin Elmer). As shown in FIG. 20, approximately 80% of the clones in this library are inactive or less active mutants, as compared to wild type P450$_{cam}$. A percentage (~20%) of the randomly selected clones exhibited improved naphthalene hydroxylation activity. This result is similar to that obtained using fluorescence image analysis (FIG. 19). However, the image analysis is much faster and less expensive (estimated analysis time: approximately 3–5 seconds for analysis of 20,000 colonies).

D. Kinetic Characterization of P450cam Mutants

Five positive P450$_{cam}$ variants (designated M7-4H, M7-6H, M7-8H, M7-9H, and M7-2R) were selected from among ~200,000 colonies (Q-bot: 9 plates) which were screened by fluorescence image analysis. Three clones with fluorescence values near the threshold (wild type activity) were also selected for comparison (M7-1; M7-2; M7-3). These clones were grown and analyzed in a 96-well plate format for activity towards three different substrates, naphthalene, 3-phenylpropionate and coumarin. One clone, M7-2R, proved to be a false positive and was not analyzed further. Results of the kinetic analysis are summarized in TABLE 2.

TABLE 2

Relative rates for P450$_{cam}$ variants towards 3-phenylpropionate, coumarin and naphthalene, as measured by generation of fluorescence per time in a 96-well plate assay using whole cells.

| | | Positive Variants | | | | Controls | | |
|---|---|---|---|---|---|---|---|---|
| Substrate | WT | M7-4H | M7-6H | M7-8H | M7-9H | M7-1 | M7-2 | M7-3 |
| 3-phenylpropionate | 13.8 | 42.8 | 43.6 | 35.4 | 33.0 | 7.8 | 9.0 | 16.2 |
| coumarin | 8.2 | 11.5 | 14.1 | 12.8 | 9.3 | 2.6 | 1.2 | 3.1 |
| naphthalene | 9.2 | 84.1 | 86.7 | 53.1 | 82.9 | 5.4 | 6.7 | 11.4 |

For naphthalene hydroxylation, variant M7-6H showed 9.4-fold increased activity over the wild type. Four of the P450 positives showed highly improved activity towards naphthalene and also towards the 3-phenylpropionate. In another series of experiments, M7-6H showed an 11-fold increase compared to wild-type on naphthalene, and M7-4H and M4-8H showed at least a 5 to 8 fold increase in activity. These three clones also had increased activity on 3-phenylpropionate, with M7-6H showing a 3.2 fold increase. The activity towards coumarin, as measured in this assay, was only slightly increased.

For the microtitre plate assay, the cells (grown in 4 ml TB/amp (100 ug/ml) media) were centrifuged for 10 min at 4° C. After the supernatant solution was removed, the harvested cells were carefully resuspended in 1 ml buffer solution (dibasic phosphate, 100 mM, pH 9.0). Then, 20 µl aliquots were placed into a Nunc fluorescence microplate. The total 180 µl reaction mixture was made up of 100 µl dibasic sodium phosphate buffer (100 mM, pH9.0), 20 µl ethanol, 10 µl substrate stock (4.5 mM coumarin in 10% ethanol, or 2 mM 3-phenylpropionate in 10% ethanol, 2 mM naphthalene in pure ethanol), and 10 µl hydrogen peroxide stock solution (50 mM $H_2O_2$ stock). The other reaction conditions are those described in EXAMPLE 2. The fluorescence was measured as a function of time, and the relative rates presented in Table 2 are the slopes of that measurement (RFU/min).

E. Sequence Characterization of P450cam Mutants

Sequence analysis of three P450$_{cam}$ mutant clones of the invention, M7-4H, M7-6H, and M7-8H, revealed a mutation at position 331 of the amino acid sequence of FIG. 3B, in which glutamic acid (Glu or E) has been changed to lysine (Lys or K). In mutant M7-4H this was the only mutation. [SEQ. ID. NO. 11]. Mutant M7-6H was found to have a second mutation at position 280 of the amino acid sequence of FIG. 3B, in which arginine (Arg or R) is changed to leucine (Leu or L). [SEQ. ID. NO. 12]. Mutant M7-8H was found to have a second mutation at position 242 of the amino acid sequence of FIG. 3B, in which cysteine (Cys or C) is changed to phenylalanine (Phe or F). [SEQ. ID. NO. 13].

F. Regiospecific P450 Enzymes

Reaction products of the oxygenation reaction catalyzed by P450 enzyme were reacted in the presence of HRP and hydrogen peroxide. In vitro HRP-catalyzed polymerization of different naphthol isomers (alpha and beta) and different dihydroxylated naphthalenes (1,5-dihydroxy-, 2,3 dihydroxy- and 2,7-dihydroxy-) generated a variety of fluorescent products, ranging from dark blue (430–460 nm), blue-green (495 nm), yellow (580 nm) to orange-red (620 nm) fluorescence. A combination of 1- or 2-naphthol and 2,7-dihydroxy naphthalene produces a red fluorescent product (620 nm), while mixing 1,5-dihydroxy naphthalene with 2,7-dihydroxy naphthalene or 2-naphthol produces pink and yellow fluorescence, respectively. The emission spectra depend on the relative molar ratios of the reactants.

Bacteria expressing wild-type P450$_{cam}$ generate only blue fluorescence (460 nm), corresponding to the conversion of naphthalene to 1- or 2-naphthol (and coupling by HRP). Bacteria expressing the P450$_{cam}$ mutants, in contrast, generate a palette of colors, shown in Table 3 below, that reflect the altered regiospecificities of the P450$_{cam}$-catalyzed hydroxylations. Thus, the screen according to the invention is sensitive to regiospecificity of hydroxylation as well as overall monooxygenase activity.

TABLE 3

Color reactions produced by Mutant Cloneqs

| | 1 | 2 | 3 | 4 | 5 | 6 | 7 | 8 | 9 | 10 | 11 | 12 |
|---|---|---|---|---|---|---|---|---|---|---|---|---|
| A | WK-BL | BL | BR-BL | PK | YL | YL | YL | BR-BL | BR-BL | BR-BL | YL | BR-BL |
| B | WK-BL | BL | BR-BL | BR-BL | YL | BR-BL | BR-BL | BR-BL | BL | BR-BL | BR-BL | BL |
| C | WK-BL | BL | PK | BR-BL | BL | BL | YL | BR-BL | RD | BR-BL | ST-YL | |
| D | WK-BL | BL | BR-BL | BL | BR-BL | BR-BL | BR-BL | BR-BL | BR-BL | YL | BL | BL |
| E | WK-BL | BL | BR-BL | BR-BL | PK | BR-BL | BR-BL | BL | BR-BL | BR-BL | BR-BL | BL |

*legends: WK: weak, ST: strong, BR; bright, BL: blue, YL; yellow, RD; red

Rows A–E of Column 1 correspond to the control strain, *E. coli* BL21(DE3). Column 2 (Rows A–E) corresponds to the control strain expressing native P450$_{cam}$. The remaining 10 columns show 50 different variants selected by fluorescence image scanning on naphthalene as substrate. Naphthalene hydroxylation activities were measured in 200 μL reactions in the 96 well plate. Cells grown in 50 ml flasks were harvested by centrigation (Beckman CS SR) at 3350 rpm and resuspended in 1 mL of 0.1 M sodium dibasic buffer (pH 9.0). A 50 μL aliquot of this solution was added to the same buffer mixtures (total of 200 μL) containing 25% ethanol, naphthalene (6 mM) and hydrogen peroxide (10 mM). Fluorescence was measured using a 96 well microfluorimeter (Perkin Elmer HTS 7000).

The screen is also selective for one of the hydroxylated isomers of 3-phenylpropionate (3-PPA). Although an oxygenase can potentially hydroxylate different positions on the aromatic backbone of 3-PPA, the product hydroxylated at the 4-position, 3-(4-hyroxyphenyl)propionate, generates strong blue fluoresence (emission at 465 nm, 350 nm excitation) when coupled with HRP. In contrast, HRP does not generate any detect able fluorescence with 3-(2-hydroxyphenyl)propionate as the substrate in an in vitro assay.

The genes encoding these and other improved P450 variants can be recombined by DNA shuffling methods or they can be further mutated in additional cycles of directed evolution or error prone PCR in order to generate further improved enzymes. P450s with improved thermostability, for example, can be obtained by measuring residual activity after incubation at elevated temperature.

EXAMPLE 9

Expression of Horseradish Peroxidase in *E. coli* and Yeast

A. Cloning of HRP

Figure 21:
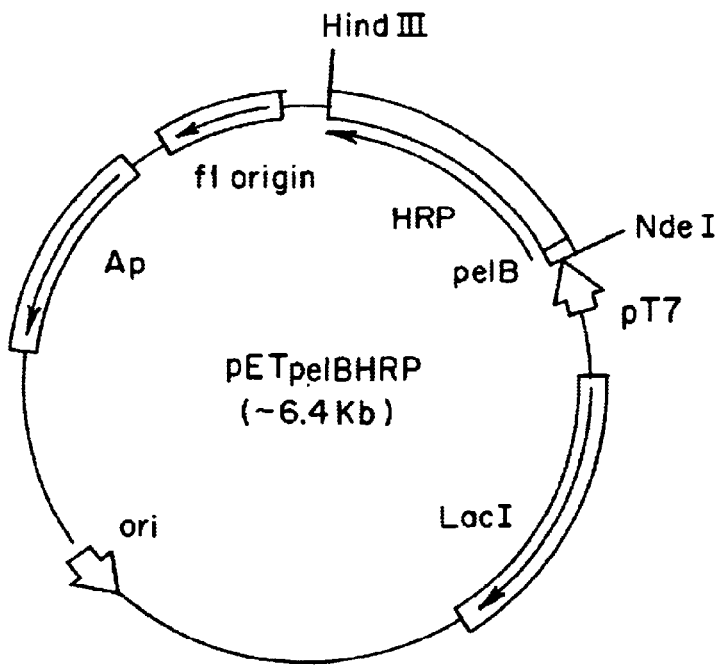
FIG. 21 is a map of an exemplary vector, pETpelBHRP, formed by inserting the HRP gene into the plasmid pET-22b(+), which contains a T7 promoter and a pelB signal sequence. The resulting vector was used as the starting point for mutagenesis to express horseradish peroxidase in *E. coli* host cells.

The HRP gene was cloned from the plasmid pBBG10 (British Biotechnologies, Ltd., Oxford, UK) by PCR techniques to introduce an Msc I site at the start codon and an EcoR I site immediately downstream from the stop codon. This plasmid contains the synthetic horseradish peroxidase (HRP) gene described in Smith et al. (26), whose DNA sequence is based on a published amino acid sequence for the HRP protein (38). pBBG10 was made by inserting the HRP sequence between the HinDIII and EcoR1 sites of the polylinker in the well-known plasmid PUC19. The PCR product obtained from this plasmid was digested with Msc I and EcoR I and ligated into similarly digested pET-22b(+) (purchased from Novagen) to yield pETpelBHRP. A map of this expression vector shown in FIG. 21. In this construct, the HRP gene was placed under the control of the T7 promoter and is fused in-frame to the pelB signal sequence (See [SEQ. ID. NO. 14] and FIG. 22), which encodes for a peptide [SEQ. ID. NO. 15] that theoretically directs transport of proteins into the periplasmic space, that is, for delivery outside the cell cytoplasm (25). The ligation product was transformed into *E. coli* strain BL21(DE3) for expression of the protein in cells both with and without induction by 1 mM IPTG.

In the cells that were induced with IPTG, no peroxidase activity above background was detected, for BL21(DE3) cells or pET-22b(+)-harboring BL21(DE3) cells, even though the level of HRP polypeptides accounted for over 20% of total cellular proteins. This was consistent with previous observations (26, 27, 28).

In the cells that were not induced with IPTG, clones were discovered that showed weak but measurable activity against azino-di-(ethylbenzthiazoline sulfonate (ABTS).

The T7 promoter in the pET-22b(+) vector is known to be leaky (29), and in theory it is therefore possible that some of the HRP polypeptide chains produced at this basal level were able to fold into the native form. Conversely, addition of IPTG leads to high-level HRP synthesis, which instead favors aggregation of chains and prevents their proper folding. Subsequently, random mutagenesis and screening were used to identify mutations that might lead to higher expression of HRP activity.

B. Random Library Generation and Screening

One of the HRP clones that showed detectable peroxidase activity was used in the first generation of error-prone PCR mutagenesis. The random libraries were generated by a modification of the previously described error-prone PCR protocol (15, 30), in which 0.15 mM of MnCl$_2$ was used instead of 0.5 mM MnCl$_2$. This protocol incorporates both manganese ions and unbalanced nucleotides, and has been shown to generate both transitions and transversions and therefore a broader spectrum of amino acid changes (31).

Briefly, the PCR reaction solution contained 20 fmoles template, 30 pmoles of each of two primers, 7 mM MgCl$_2$, 50 mM KCl, 10 mM Tris-HCl (pH 8.3), 0.01% gelatin, 0.2 mM dGTP, 0.2 mM dATP, 1 mM dCTP, 1 mM dTTP, 0.15 mM MnCl$_2$, and 5 unit of Taq polymerase in a 100 μl volume. PCR reactions were performed in a MJ PTC-200 cycler (MJ Research, MA) for 30 cycles with the following parameters: 94° C. for 1 min, 50° C. for 1 min, and 72° C. for 1 min. The primers used were:

5'-TTATTGCTCAGCGGTGGCAGCAGC [SEQ. ID NO. 18], and

5'-AAGCGCTCATGAGCCCGAAGTGGC [SEQ. ID. NO. 19].

The PCR products were purified with a Promega Wizard PCR kit, and digested with Nde I and Hind III. The digestion products were subjected to gel-purification with a QIAEX II gel extraction kit, and the HRP fragments were ligated back into the similarly digested and gel-purified pET-22b(+) vector. Ligation mixtures were transformed in the BL21 (DE3) cells by electroporation with a Gene Pulser II (Bio-Rad).

The PCR products were ligated back into the pET-22b(+) vector which was transformed into the BL21(DE3) cells by electroporation. Cell growth and expression was carried out in either 96-well or 384-well microplates in LB medium at 30° C. Peroxidase activity tests were performed with H$_2$O$_2$ and ABTS (32).

For each generation, typically 12,000–15,000 colonies were picked and screened in 96-well plates. This number represents an exhaustive search of all accessible single mutants, with a probability of 95% for any mutant to be sampled at least once (33). Colonies were either picked manually, or using an automated colony picker at Caltech, Q-bot (Genetix, UK).

Of the 12,000 colonies that were screened in the first generation (no IPTG added), a mutant designated HRP1A6 showed 10–14 fold higher peroxidase activity than the parent clone. This mutant clone also showed markedly decreased activity when as little as 5 μM of IPTG was added. Sigma reports that 1 mg of highly purified HRP from horseradish has a total activity of 1,000 units, as determined by the ABTS assay. Other workers reported similar results (26). Based on this data, the concentration of active HRP was estimated to be ~100 ug/L. HRP1A6 shows a total activity of greater than 100 units/L. This compares favorably with the yield obtained from refolding of aggregated HRP chains in vitro (26). This level of expression for the HRP mutant is also similar to that for bovine pancreatic trypsin inhibitor (BPTI) in *E. coli* (34), an unglycosylated protein with three disulfide bonds. Once again, greater than 95% of the HRP activity was found in the LB culture medium as judged by the ABTS activity.

The mutant HRP remained stable for up to a week at 4° C. IPTG was omitted in all HRP expression experiments, unless otherwise specified. Peroxidase activity tests for HRP were performed with a classical peroxidase assay, ABTS and hydrogen peroxide (26). Fifteen $\mu$l of cell suspension was mixed with 140 $\mu$l of ABTS/$H_2O_2$ (2.9 mM ABTS, 0.5 mM $H_2O_2$, pH 4.5) in microplates, and the activity was determined with a SpectraMax plate reader (Molecular Devices, Sunnyvale, Calif.) at 25° C. A unit of HRP is defined as the amount of enzyme that oxidizes 1 $\mu$mole of ABTS per min at the assay conditions.

Figure 24:
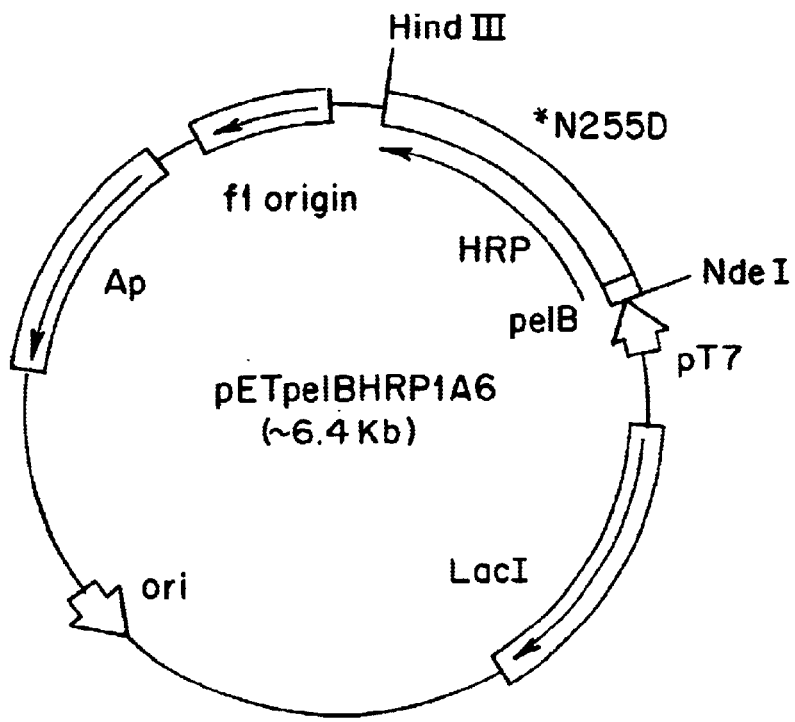
FIG. 24 is a map of the expression vector pETpelBHRP1A6.

Sequencing of the mutant gene found a mutation at position 255, in which the codon AAC for the amino acid asparagine (Asn or N) was changed to the codon GAC for the amino acid aspartic acid (Asp or D). This residue is a putative glycosylation site, and is located at the surface of the protein. The sequence of this mutant (HRP1A6) is shown in FIG. 23 [SEQ. ID. NO. 17]. A map of a plasmid pETpelBHRP1A6 containing this mutant is shown in FIG. 24.

C. Functional Expression of HRP in Yeast

The native HRP protein contains four disulfide bonds, and *E. coli* has only a limited capability to support disulfide formation. In theory, these well-conserved disulfides in HRP (and other plant peroxidases) are likely to be important for the structural integrity of the protein, and may not be replaceable by mutations elsewhere. Yeast has a much greater ability to support the formation of disulfide bonds. Thus, yeast can be used as suitable expression host, in place of *E. coli*, particularly if it s desired to relieve the apparent limitation on the folding of HRP imposed by any constraints on disulfide formation in *E. coli*. For example, *S. cerevisiae* can be used as a host for the expression of mutant HRP genes and proteins.

Figure 25:
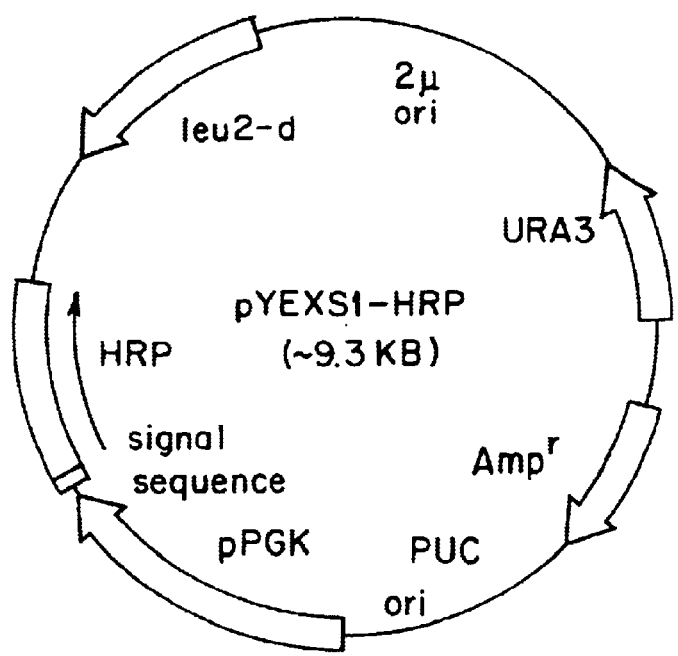
FIG. 25 is a map of the expression vector pYEXS1-HRP containing a coding sequence for HRP cloned into the secretion plasmid pYEX-S1.

The HRP mutant (HRP1A6) was cloned into the secretion vector pYEX-S1 obtained from Clontech (Palo Alto, Calif.) (19), yielding pYEXS1-HRP (FIG. 25). This vector utilizes the constitutive phosphoglycerate kinase promoter and a secretion signal peptide from *Kluveromyces lactis*. The plasmid was first propagated in *E. coli*, and then transformed into *S. cerevisiae* strain BJ5464, obtained from the Yeast Genetic Stock Center (YGSC), University of California, Berkeley using the LiAc method as described (20). BJ5464 is protease deficient, and has been found to be generally suitable for secretion.

A first generation of error-prone PCR of HRP in yeast was performed. Among the first 7,400 mutants screened, four variants showed 400% higher activity than HRP1A6 in yeast.

EXAMPLE 10

Screening for Other Catalysts and Optimizing Reaction Conditions

Empirical approaches are the only proven successful approaches to the development of novel catalysts. However, empirical approaches are often slow, costly and labor-intensive. Parallel investigation of a large number of catalyst candidates can significantly reduce the time, cost and labor associated with catalyst discovery. In addition to enzymatic catalysts, the methods of this invention can be applied to screen chemical libraries for oxidation catalysts.

In addition to catalyst discovery, it is also important to optimize reaction conditions for any given catalyst. This requires the simultaneous optimization of a number of parameters, each of which can have a significant effect on catalyst performance. Important parameters include choice of solvent, reactant profile, presence of other compounds or contaminants in the reaction mixture, temperature, pressure etc. Given the large number of potential variables, optimization is also preferably done in parallel tests, in which dozens or even thousands of conditions are tested. Once an oxidation catalyst is in hand, the invention can be used to rapidly evaluate or optimize conditions for that catalyst.

The invention can be used with single catalysts (e.g. arrayed in individual wells of a microtiter plate) or it can be used with various pooling strategies in which multiple candidate catalysts are assayed simultaneously. If a particular set of catalysts shows reactivity in a given reaction, the members of that set can be assayed individually to discover the catalyst of interest.

Combinatorial Approaches to Catalyst Design and Discovery.

The invention can be used to screen libraries of non-enzyme catalysts for their ability to oxygenate (e.g. hydroxylate) substrates, such as aromatic substrates. Catalysts identified in this way can in turn be used as "leads" for the discovery of catalysts that hydroxylate other substrates, catalyze other oxygen insertion reactions, or which have more activity or stability, or which can function under different conditions. For example, the techniques of combinatorial chemistry can be used to generate additional libraries of compounds for testing, once a lead compound is identified (43, 48, 49).

To use the invention for this application, the screening reaction with the coupling enzyme would generally be performed after the oxygenation reaction has completed. If necessary or appropriate, the reaction conditions can be adjusted after the oxygenation reaction, so as to promote the coupling reaction. That is, conditions that are compatible with maintaining the activity of the coupling enzyme must be provided. Alternatively, the oxygenated products could be extracted into a solvent (e.g. dichloromethane or a solvent in which the coupling enzyme, such as HRP, is known to function). HRP, a preferred coupling enzyme, is known to function as a coupling enzyme in aqueous buffer and also in various organic solvents (including hexane, acetonitrile, t-butanol and others) and functions over a temperature range of approximately 4 to 65° C., with best performance around 20–50° C. The coupling reaction conditions can be readily tested to determine that they support the activity of the coupling enzyme. The coupling reaction conditions are also preferably chosen to minimize dilution of the oxygenated product.

This embodiment also allows measurement of an "end point" of the oxygenation reaction. For example, the oxygenation reaction would be allowed to proceed for a given amount of time. At this point, the conditions are changed to allow the coupling reaction (and coupling enzyme and oxygen donor would be added). The generation of colored or fluorescent products (or absorption of UV light, chemiluminescence, etc.) indicates the total concentration of the oxygenated product made during that time. If the oxygenation catalyst functions under conditions that are also compatible with the coupling enzyme, both reactions be done simultaneously or contemporaneously (oxygenation and coupling).

Optimizing Reaction Conditions.

The invention can also be used to optimize reaction conditions for any given catalyst.

The hydroxylation of aromatic compounds can be is difficult. Results can be poor because introduction of a hydroxyl group activates the ring for further reaction and oxidation. Furthermore, the reaction conditions are often harsh and potentially explosive (45). Thus, evaluating and optimizing reaction conditions for a given catalyst can be beneficial.

There are various non-enzyme catalysts that are known to catalyze aromatic hydroxylations, similar to monooxygenase and dioxygenase enzymes. DeHaan et al. (46) describe hydroxylation of various aromatics in high yield, using a bis(trimethylsilyl)peroxide/triflic acid system. The product was extracted into an organic solvent (dichloromethane) for analysis. The present invention can be used to determine the progress of the reaction by adding HRP (or other suitable coupling enzyme) and peroxide. Alternatively, a solvent that both extracts the product and supports the activity of the HRP can be used.

As another example, a large class of catalysts that can perform hydroxylations are the substituted porphyrins, which have been characterized as non-enzyme "mimics" of P450 enzymes (47) This invention can be used to screen combinatorial libraries of porphyrin-based catalysts for hydroxylation of aromatics under a variety of conditions. It can also be used to screen libraries of di-iron compounds that mimic di-iron oxygenases (51).

Having thus described exemplary embodiments of the invention, it should be noted by those skilled in the art that the within disclosures are exemplary only and that various other alternatives, adaptations, and modifications may be made within the scope of the invention. For example, it will be understood by practitioners that the steps of any method of the invention can generally be performed in any order, including simultaneously or contemporaneously, unless a particular order is expressly required, or is necessarily inherent or implicit in order to practice the invention. Accordingly, the invention is not limited to any specific embodiments or illustrations herein. The invention is defined according to the appended claims, and is limited only according to the claims.

BIBLIOGRAPHY

1. Faber, K. Biotransformations in Organic Chemistry, Springer-Verlad, Berlin, p.214, 217 (1997)
2. Cook, D. L. and Atkins, W. M. *Biochemistry*, 36, 10801 (1997).
3. Short, J. *Nature Biotechnol.* 15, 1322 (1997).
4. Sheldon, R. A. Catalysis: the key to waste minimization. *J. Chem. Tech. Bitechnol.* 68, 381 (1997).
5. Gonzalez, F. J. and Nebert, D. W., Evolution of the P450-gene superfamily—animal plant warfare, molecular drive and human genetic differences in drug oxidation. *Trends Genet.* 6, 182–186 (1990).(1975).
6. Guengerich, F. P. in Cytochrome P450: Structure, Mechanism and Biochemistry (Ortiz de Montellano, P. R., E.d.) pp. 473–536, Plenum Press, New York (1995).
7. England, P. A., Harford-Cross, C. F., Stevenson, J.-A., Rouch, D. A., and Wong, L.-L., *FEBS Lett.* 424, 271–274 (1998).
8. Lipscomb, J. D., Sligar, S. G., Namtvedt, M. J. Gunsalus, I. C. *J. Biol Chem.*, 251, 1116 (1976).
9. Blake II, R. C. and Coon, M. *J. Biol. Chem.*, 255, 4100 (1980).
10. van Deurzen, M. P. J., Van Rantwijk, F., Sheldon, R. A. *Tetrahedron*, 53, 13183 (1997).
11. Nordblom, G. D., White, R. E., and Coon, M. *J. Arch. Biochem. Biophys.*, 175, 524 (1976).
12. Rahimtula, A. D. and P.J. O'Brien *Biochem. Biophys. Res. Commun.* 60, 440 (1974).
13. U.S. Pat. Nos. 5,741,691 and 5,811,238.
14. Mueller, E. J., Loida, P. J., and Sligar, S. G., Twenty-five Years of P450$_{cam}$ Research, in Cytochrome P450: *Structure, Mechanism, and Biochemistry* (2nd ed. Montellano, P. R. O. de), Plenum Press, NY, pp83–124 (1995).
15. Cadwell, R. C. and Joyce, G. F., Randomization of Genes by PCR Mutagenesis, in: *PCR Methods & Applications*, Cold Spring Harbor Laboratory Press, NY, pp28–33 (1992).
16. U.S. Pat. No. 5,605,793
17. PCT Application No. PCT/US98/05956
18. D. R. Thatcher, A. Hitchcock, in *Mechanisms of Protein Folding* R. H. Pain, Ed. (IRL Press, Oxford, 1994) pp. 229–261.
19. C. B. Anfinsen, *Science* 181, 223–230 (1973).
20. C. H. Schein, *Bio/Technology* 8, 308–317 (1990).
21. A. Mitraki, J. King, i FEBS Lett. 307, 20–25 (1992).
22. J. X. Zhang, D. P. Goldenberg, *Biochemistry* 32, 14075–14080 (1993).
23. R. Wetzel, L. P. Perry, C. Veilleux, *Bio/Technology* 9, 731–737 (1991).
24. A. Crameri, E. A. Whiteborn, E. Tate, W. P. C. Stemmer, *Nature Biotechnol.* 14, 315–319 (1996).
25. S. P. Lei, H. C. Lin, S. S. Wang, J. Callaway, G. Wilcox, *J. Bacteriol.* 169, 4379–4383 (1987).
26. A. T. Smith, et al., *J. Biol. Chem.* 265, 13335–13343 (1990).
27. A. M. Egorov, et al., *Ann. N.Y. Acad. Sci.*, 35–40 (1991).
28. S. A. Ortlepp, D. Pollard-Knight, D. J. Chiswell, *J. Biotechnol.* 11, 353–364 (1989).
29. F. W. Studier, A. H. Rosenberg, J. J. Dunn, J. W. Dubendorff, *Meth. Enzymol.* 185, 60–89 (1990).
30. S. Shafikhani, R. A. Siegel, E. Ferrari, V. Schellenberger, *Biotechniques* 23, 304–310 (1997).
31. K. Sirotkin, *J. Theor. Biol.* 123, 261–279 (1986).
32. J. S. Shindler, R. E. Childs, W. G. Bardsley, *Eur. J. Biochem.* 65, 325–331 (1976).
33. J. Carbon, L. Clarke, C. Ilgen, B. Ratzkin, in *Recombinant Molecules: Impact on Science and Society* R. F. J. Beers, E. G. Bassett, Eds. (Raven Press, New York, 1977).
34. M. Ostermeier, K. Desutter, G. Georgiou, *J. Biol. Chem.* 271, 10616–10622 (1996).
35. R. Parekh, K. Forrester, D. Wittrup, *Protein Expres. Purif.* 6, 537–545 (1995).
36. R. D. Gietz, R. H. Schiestl, A. Willems, R. A. Woods, *Yeast* 11, 355–360 (1995).
37. Riggs, P., in Ausubel, F. M., et al. (eds); Current Protocols in Molecular Biology (1992) Greene Associates/Wiley Interscience, New York.
38. K. G. Welinder, *Eur. J. Biochem.* 96, 483–502 (1979).
39. D. B. Goodin, M. G. Davidson, J. A. Roe, A. G. Mauk, and M. Smith, Biochemistry 30, 4953–4962 (1991)
40. M. M. Fitzgerald, M. J. Churchill, D. E. McRee, and D. B. Goodin, Biochemistry, 33, 3807–3818 (1994).
41. Zylstra, G. J. and Gibson, D. T. (1989) J. Bacteriol. 264, 14940–14946.
42. Miura, Y. and Fulco, A.J. *Biochim. Biophys. Acta*, 388, 305 (1975).
43. Borchardt, J. K., Combinatorial Chemistry: Not just for pharmaceuticals. *Today's Chem. at Work*, November 1998, pp. 36–39.

44. Setti, L. et al., Horseradish peroxidase-catalyzed oxidative coupling of 3-methyl 2-benzothiazolinone hydrazone and methoxyphenols. *Enz. & Mocrob. Tech.,* 22:656–661 (1998).
45. G. A. Olah & T. D. Ernst, Oxyfunctionalization of Hydrocarbons. 14. Electrophilic Hydroxylation of Aromatics with Bis(trimethylsilyl)peroxide/Triflic Acid, *J. Org. Chem.* 54; 1204–1206 (1989). p0 46. DeHaan et al., [CITE]
47. J. T. Groves & Y.-Z. Han, Models and Mechanisms of Cytochrome P450 Action, in Cytochrome P450, 2nd Edition, Ed. P. R. Ortiz de Montellano, Plenum, NY pp3–48.
48. A. H. Hoveyda, Catalyst discovery through combinatorial chemistry, *Chemistry & Biology* 5:R187–R191 (1998).
49. Stuart Borman, Combinatorial Catalysts, *Chemical & Engineering News*, Nov. 4, 1996 p. 37–39.
50. Handelsman, J. et al., Molecular biological access to the chemistry of unknown soil microbes: a new frontier for natural products, *Chem. & Biol.,* 5 :R245–249 (1998).
51. Menage, S. et al., $O_2$ activation and aromatic hydroxylation performed by diiron complexes, *J. Am. Chem. Soc.,* 120, 133370–13382 (1998).

SEQUENCE LISTING

<160> NUMBER OF SEQ ID NOS: 19

<210> SEQ ID NO 1
<211> LENGTH: 1402
<212> TYPE: DNA
<213> ORGANISM: P. Putida

<400> SEQUENCE: 1

```
ctgcaggatc gttatccgct ggccgatctg atcacccagc gttttttccat cgacgaggcc     60
agcaaggcac ttgaactggt caaggcagga gcactgatca aacccgtgat cgactccact    120
ctttagccaa cccgcgttcc aggagaacaa caacaatgac gactgaaacc atacaaagca    180
acgccaatct tgcccctctg ccaccccatg tgccagagca cctggtattc gacttcgaca    240
tgtacaatcc gtcgaatctg tctgccggcg tgcaggaggc ctgggcagtt ctgcaagaat    300
caaacgtacc ggatctggtg tggactcgct gcaacggcgg acactggatc gccactcgcg    360
gccaactgat ccgtgaggcc tatgaagatt accgccactt ttccagcgag tgcccgttca    420
tccctcgtga agccggcgaa gcctacgact tcattcccac ctcgatggat ccgcccgagc    480
agcgccagtt tcgtgcgctg gccaaccaag tggttggcat gccggtggtg gataagctgg    540
agaaccggat ccaggagctg gcctgctcgc tgatcgagag cctgcgcccg caaggacagt    600
gcaacttcac cgaggactac gccgaaccct tcccgatacg catcttcatg ctgctcgcag    660
gtctaccgga agaagatatc ccgcacttga aatacctaac ggatcagatc acccgtccgg    720
atggcagcat gaccttcgca gaggccaagg aggcgctcta cgactatctg ataccgatca    780
tcgagcaacg caggcagaag ccgggaaccg acgctatcag catcgttgcc aacggccagg    840
tcaatgggcg accgatcacc agtgacgaag ccaagaggat gtgtggcctg ttactggtcg    900
gcggcctgga tacggtggtc aatttcctca gcttcagcat ggagttcctg gccaaaagcc    960
cggagcatcg ccaggagctg atcgagcgtc ccgagcgtat tccagccgct tgcgaggaac   1020
tactccggcg cttctcgctg gttgccgatg gccgcatcct cacctccgat tacgagtttc   1080
atggcgtgca actgaagaaa ggtgaccaga tcctgctacc gcagatgctg tctggcctgg   1140
atgagcgcga aaacgcctgc ccgatgcacg tcgacttcag tcgccaaaag gtttcacaca   1200
ccacctttgg ccacggcagc catctgtgcc ttggccagca cctggcccgc cgggaaatca   1260
tcgtcaccct caaggaatgg ctgaccagga ttcctgactt ctccattgcc ccgggtgccc   1320
agattcagca caagagcggc atcgtcagcg gcgtgcaggc actccctctg gtctgggatc   1380
cggcgactac caaagcggta ta                                           1402
```

<210> SEQ ID NO 2

```
<211> LENGTH: 414
<212> TYPE: PRT
<213> ORGANISM: P. Putida

<400> SEQUENCE: 2

Thr Thr Glu Thr Ile Gln Ser Asn Ala Asn Leu Ala Pro Leu Pro Pro
  1               5                  10                  15

His Val Pro Glu His Leu Val Phe Asp Phe Asp Met Tyr Asn Pro Ser
             20                  25                  30

Asn Leu Ser Ala Gly Val Gln Glu Ala Trp Ala Val Leu Gln Glu Ser
         35                  40                  45

Asn Val Pro Asp Leu Val Trp Thr Arg Cys Asn Gly Gly His Trp Ile
 50                  55                  60

Ala Thr Arg Gly Gln Leu Ile Arg Glu Ala Tyr Glu Asp Tyr Arg His
 65                  70                  75                  80

Phe Ser Ser Glu Cys Pro Phe Ile Pro Arg Glu Ala Gly Glu Ala Tyr
                 85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
            115                 120                 125

Asn Arg Ile Gln Glu Leu Ala Cys Ser Leu Ile Glu Ser Leu Arg Pro
130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
            195                 200                 205

Glu Gln Arg Arg Gln Lys Pro Gly Thr Asp Ala Ile Ser Ile Val Ala
210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Gly Leu Asp Thr Val Val Asn Phe
                245                 250                 255

Leu Ser Phe Ser Met Glu Phe Leu Ala Lys Ser Pro Glu His Arg Gln
            260                 265                 270

Glu Leu Ile Glu Arg Pro Glu Arg Ile Pro Ala Ala Cys Glu Glu Leu
            275                 280                 285

Leu Arg Arg Phe Ser Leu Val Ala Asp Gly Arg Ile Leu Thr Ser Asp
            290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
            340                 345                 350

Gly Ser His Leu Cys Leu Gly Gln His Leu Ala Arg Arg Glu Ile Ile
            355                 360                 365

Val Thr Leu Lys Glu Trp Leu Thr Arg Ile Pro Asp Phe Ser Ile Ala
370                 375                 380

Pro Gly Ala Gln Ile Gln His Lys Ser Gly Ile Val Ser Gly Val Gln
```

```
                385                 390                 395                 400
        Ala Leu Pro Leu Val Trp Asp Pro Ala Thr Thr Lys Ala Val
                        405                 410

<210> SEQ ID NO 3
<211> LENGTH: 31
<212> TYPE: DNA
<213> ORGANISM: Artificial Sequence
<220> FEATURE:
<223> OTHER INFORMATION: Primer sequence

<400> SEQUENCE: 3
gatcatgaat gagaccgaca catcacctat c                                    31

<210> SEQ ID NO 4
<211> LENGTH: 32
<212> TYPE: DNA
<213> ORGANISM: Artificial Sequence
<220> FEATURE:
<223> OTHER INFORMATION: Primer sequence

<400> SEQUENCE: 4
acgaattcta gaagaagaaa ctgaggttat tg                                   32

<210> SEQ ID NO 5
<211> LENGTH: 27
<212> TYPE: DNA
<213> ORGANISM: Artificial Sequence
<220> FEATURE:
<223> OTHER INFORMATION: Primer sequence

<400> SEQUENCE: 5
ttggatccgg tggaccttgt ccatttg                                         27

<210> SEQ ID NO 6
<211> LENGTH: 29
<212> TYPE: DNA
<213> ORGANISM: Artificial Sequence
<220> FEATURE:
<223> OTHER INFORMATION: Primer sequence

<400> SEQUENCE: 6
gctctagatc aaccgaagtg cttgtcgag                                       29

<210> SEQ ID NO 7
<211> LENGTH: 24
<212> TYPE: DNA
<213> ORGANISM: Artificial Sequence
<220> FEATURE:
<223> OTHER INFORMATION: Primer sequence

<400> SEQUENCE: 7
cggaattcta ggaaacagac catg                                            24

<210> SEQ ID NO 8
<211> LENGTH: 29
<212> TYPE: DNA
<213> ORGANISM: Artificial Sequence
<220> FEATURE:
<223> OTHER INFORMATION: Primer sequence

<400> SEQUENCE: 8
ccggatccaa cctgggtcga agtcaaatg                                       29

<210> SEQ ID NO 9
```

```
<211> LENGTH: 24
<212> TYPE: DNA
<213> ORGANISM: Artificial Sequence
<220> FEATURE:
<223> OTHER INFORMATION: Primer sequence

<400> SEQUENCE: 9
catcgatgct taggaggtca tatg                                        24

<210> SEQ ID NO 10
<211> LENGTH: 25
<212> TYPE: DNA
<213> ORGANISM: Artificial Sequence
<220> FEATURE:
<223> OTHER INFORMATION: Primer sequence

<400> SEQUENCE: 10
tcatgtttga cagcttatca tcgat                                       25

<210> SEQ ID NO 11
<211> LENGTH: 414
<212> TYPE: PRT
<213> ORGANISM: Artificial Sequence
<220> FEATURE:
<223> OTHER INFORMATION: Mutant M7-4H

<400> SEQUENCE: 11

Thr Thr Glu Thr Ile Gln Ser Asn Ala Asn Leu Ala Pro Leu Pro Pro
 1               5                  10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Tyr
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
    130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Arg Gln Lys Pro Gly Thr Asp Ala Ile Ser Ile Val Ala
    210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Gly Leu Asp Thr Val Val Asn Phe
                245                 250                 255
```

-continued

```
Leu Ser Phe Ser Met Glu Phe Leu Ala Lys Ser Pro Glu His Arg Gln
            260                 265                 270

Glu Leu Ile Glu Arg Pro Glu Arg Ile Pro Ala Ala Cys Glu Glu Leu
        275                 280                 285

Leu Arg Arg Phe Ser Leu Val Ala Asp Gly Arg Ile Leu Thr Ser Asp
    290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Lys Asn Ala Cys Pro Met
                325                 330                 335

His Val Asp Phe Ser Arg Gln Lys Val Ser His Thr Thr Phe Gly His
            340                 345                 350

Gly Ser His Leu Cys Leu Gly Gln His Leu Ala Arg Arg Glu Ile Ile
        355                 360                 365

Val Thr Leu Lys Glu Trp Leu Thr Arg Ile Pro Asp Phe Ser Ile Ala
    370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410
```

```
<210> SEQ ID NO 12
<211> LENGTH: 414
<212> TYPE: PRT
<213> ORGANISM: Artificial Sequence
<220> FEATURE:
<223> OTHER INFORMATION: Mutant M7-6H

<400> SEQUENCE: 12

Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Tyr
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
    130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205
```

-continued

```
Glu Gln Arg Arg Gln Lys Pro Gly Thr Asp Ala Ile Ser Ile Val Ala
    210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Leu Asp Thr Val Val Asn Phe
                245                 250                 255

Leu Ser Phe Ser Met Glu Phe Leu Ala Lys Ser Pro Glu His Arg Gln
                260                 265                 270

Glu Leu Ile Glu Arg Pro Glu Leu Ile Pro Ala Ala Cys Glu Glu Leu
            275                 280                 285

Leu Arg Arg Phe Ser Leu Val Ala Asp Gly Arg Ile Leu Thr Ser Asp
    290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Lys Asn Ala Cys Pro Met
                325                 330                 335

His Val Asp Phe Ser Arg Gln Lys Val Ser His Thr Thr Phe Gly His
                340                 345                 350

Gly Ser His Leu Cys Leu Gly Gln His Leu Ala Arg Arg Glu Ile Ile
            355                 360                 365

Val Thr Leu Lys Glu Trp Leu Thr Arg Ile Pro Asp Phe Ser Ile Ala
    370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410

<210> SEQ ID NO 13
<211> LENGTH: 414
<212> TYPE: PRT
<213> ORGANISM: Artificial Sequence
<220> FEATURE:
<223> OTHER INFORMATION: Mutant M7-8H

<400> SEQUENCE: 13

Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
                20                  25                  30

Asn Leu Ser Ala Gly Val Gln Glu Ala Trp Ala Val Leu Gln Glu Ser
            35                  40                  45

Asn Val Pro Asp Leu Val Trp Thr Arg Cys Asn Gly Gly His Trp Ile
50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Tyr
                85                  90                  95

Asp Phe Ile Pro Thr Ser Met Asp Pro Pro Glu Gln Arg Gln Phe Arg
                100                 105                 110

Ala Leu Ala Asn Gln Val Val Gly Met Pro Val Val Asp Lys Leu Glu
            115                 120                 125

Asn Arg Ile Gln Glu Leu Ala Cys Ser Leu Ile Glu Ser Leu Arg Pro
        130                 135                 140

Gln Gly Gln Cys Asn Phe Thr Glu Asp Tyr Ala Glu Pro Phe Pro Ile
145                 150                 155                 160
```

```
Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Gln Lys Pro Gly Thr Asp Ala Ile Ser Ile Val Ala
    210                 215                 220

Asn Gly Gln Val Asn Gly Arg Pro Ile Thr Ser Asp Glu Ala Lys Arg
225                 230                 235                 240

Met Phe Gly Leu Leu Val Gly Gly Leu Asp Thr Val Val Asn Phe
                245                 250                 255

Leu Ser Phe Ser Met Glu Phe Leu Ala Lys Ser Pro Glu His Arg Gln
                260                 265                 270

Glu Leu Ile Glu Arg Pro Glu Arg Ile Pro Ala Ala Cys Glu Glu Leu
            275                 280                 285

Leu Arg Arg Phe Ser Leu Val Ala Asp Gly Arg Ile Leu Thr Ser Asp
    290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Lys Asn Ala Cys Pro Met
                325                 330                 335

His Val Asp Phe Ser Arg Gln Lys Val Ser His Thr Thr Phe Gly His
                340                 345                 350

Gly Ser His Leu Cys Leu Gly Gln His Leu Ala Arg Arg Glu Ile Ile
            355                 360                 365

Val Thr Leu Lys Glu Trp Leu Thr Arg Ile Pro Asp Phe Ser Ile Ala
    370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410

<210> SEQ ID NO 14
<211> LENGTH: 66
<212> TYPE: DNA
<213> ORGANISM: E. coli

<400> SEQUENCE: 14
atgaaatacc tattgcctac ggcagccgct ggattgttat tactcgctgc ccaaccagcc    60
atggcc                                                              66

<210> SEQ ID NO 15
<211> LENGTH: 22
<212> TYPE: PRT
<213> ORGANISM: E. coli

<400> SEQUENCE: 15

Met Lys Tyr Leu Leu Pro Thr Ala Ala Ala Gly Leu Leu Leu Leu Ala
  1               5                  10                  15

Ala Gln Pro Ala Met Ala
            20

<210> SEQ ID NO 16
<211> LENGTH: 927
<212> TYPE: DNA
```

<213> ORGANISM: Escherichia coli

<400> SEQUENCE: 16

```
atgcagttaa cccctacatt ctacgacaat agctgtccca acgtgtccaa catcgttcgc    60
gacacaatcg tcaacgagct cagatccgat cccaggatcg ctgcttcaat attacgtctg   120
cacttccatg actgcttcgt gaatggttgc gacgctagca tattactgga caacaccacc   180
agtttccgca ctgaaaagga tgcattcggg aacgctaaca gcgccagggg ctttccagtg   240
atcgatcgca tgaaggctgc cgttgagtca gcatgcccac gaacagtcag ttgtgcagac   300
ctgctgacta tagctgcgca acagagcgtg actcttgcag gcggaccgtc ctggagagtg   360
ccgctcggtc gacgtgactc cctacaggca ttcctagatc tggccaacgc caacttgcct   420
gctccattct tcaccctgcc ccagctgaag gatagcttta gaaacgtggg tctgaatcgc   480
tcgagtgacc ttgtggctct gtccggagga cacacatttg gaaagaacca gtgtaggttc   540
atcatggata ggctctacaa tttcagcaac actgggttac ctgaccccac gctgaacact   600
acgtatctcc agacactgag aggcttgtgc ccactgaatg gcaacctcag tgcactagtg   660
gactttgatc tgcggacccc aaccatcttc gataacaagt actatgtgaa tctagaggag   720
cagaaaggcc tgatacagag tgatcaagaa ctgtttagca gtccagacgc cactgacacc   780
atcccactgg tgagaagttt tgctaactct actcaaacct tctttaacgc cttcgtggaa   840
gccatggacc gtatgggtaa cattacccct ctgacgggta cccaaggcca gattcgtctg   900
aactgcagag tggtcaacag caactct                                        927
```

<210> SEQ ID NO 17
<211> LENGTH: 309
<212> TYPE: PRT
<213> ORGANISM: Escherichia coli

<400> SEQUENCE: 17

```
Met Gln Leu Thr Pro Thr Phe Tyr Asp Asn Ser Cys Pro Asn Val Ser
 1               5                  10                  15

Asn Ile Val Arg Asp Thr Ile Val Asn Glu Leu Arg Ser Asp Pro Arg
            20                  25                  30

Ile Ala Ala Ser Ile Leu Arg Leu His Phe His Asp Cys Phe Val Asn
        35                  40                  45

Gly Cys Asp Ala Ser Ile Leu Leu Asp Asn Thr Thr Ser Phe Arg Thr
    50                  55                  60

Glu Lys Asp Ala Phe Gly Asn Ala Asn Ser Ala Arg Gly Phe Pro Val
65                  70                  75                  80

Ile Asp Arg Met Lys Ala Ala Val Glu Ser Ala Cys Pro Arg Thr Val
                85                  90                  95

Ser Cys Ala Asp Leu Leu Thr Ile Ala Ala Gln Gln Ser Val Thr Leu
            100                 105                 110

Ala Gly Gly Pro Ser Trp Arg Val Pro Leu Gly Arg Arg Asp Ser Leu
        115                 120                 125

Gln Ala Phe Leu Asp Leu Ala Asn Ala Asn Leu Pro Ala Pro Phe Phe
    130                 135                 140

Thr Leu Pro Gln Leu Lys Asp Ser Phe Arg Asn Val Gly Leu Asn Arg
145                 150                 155                 160

Ser Ser Asp Leu Val Ala Leu Ser Gly Gly His Thr Phe Gly Lys Asn
                165                 170                 175

Gln Cys Arg Phe Ile Met Asp Arg Leu Tyr Asn Phe Ser Asn Thr Gly
            180                 185                 190
```

```
Leu Pro Asp Pro Thr Leu Asn Thr Thr Tyr Leu Gln Thr Leu Arg Gly
        195                 200                 205

Leu Cys Pro Leu Asn Gly Asn Leu Ser Ala Leu Val Asp Phe Asp Leu
        210                 215                 220

Arg Thr Pro Thr Ile Phe Asp Asn Lys Tyr Tyr Val Asn Leu Glu Glu
225             230                 235                 240

Gln Lys Gly Leu Ile Gln Ser Asp Gln Glu Leu Phe Ser Ser Pro Asp
                245                 250                 255

Ala Thr Asp Thr Ile Pro Leu Val Arg Ser Phe Ala Asn Ser Thr Gln
        260                 265                 270

Thr Phe Phe Asn Ala Phe Val Glu Ala Met Asp Arg Met Gly Asn Ile
        275                 280                 285

Thr Pro Leu Thr Gly Thr Gln Gly Gln Ile Arg Leu Asn Cys Arg Val
        290                 295                 300

Val Asn Ser Asn Ser
305

<210> SEQ ID NO 18
<211> LENGTH: 24
<212> TYPE: DNA
<213> ORGANISM: Artificial Sequence
<220> FEATURE:
<223> OTHER INFORMATION: Primer sequence

<400> SEQUENCE: 18
ttattgctca gcggtggcag cagc                                          24

<210> SEQ ID NO 19
<211> LENGTH: 24
<212> TYPE: DNA
<213> ORGANISM: Artificial Sequence
<220> FEATURE:
<223> OTHER INFORMATION: Primer sequence

<400> SEQUENCE: 19
aagcgctcat gagcccgaag tggc                                          24
```

What is claimed is:

1. A functional cytochrome P450 oxygenase variant comprising at least one mutation at a position selected from the group consisting of amino acid positions 242, 280, and 331 of SEQ ID NO:2 and having at least 99% sequence identity to SEQ ID NO:2.

2. The cytochrome P450 oxygenase variant of claim 1 comprising at least one mutation selected from the group consisting of:
   (a) a glutamic acid to lysine mutation at position 331 of SEQ ID NO:2;
   (b) an arginine to leucine mutation at position 280 of SEQ ID NO:2; and
   (c) a cysteine to phenylalanine mutation at position 242 of SEQ ID NO:2.

3. The variant cytochrome P450 oxygenase of claim 1, comprising at least one mutation selected from the group consisting of:
   (a) a glutamic acid to arginine or histidine mutation at position 331 of SEQ ID NO:2; and
   (b) an arginine to isoleucine, methionine, or valine mutation at position 280 of SEQ ID NO:2.

4. A cytochrome P450 oxygenase variant having a catalytic activity at least two times the catalytic activity of wild-type cytochrome P450$_{cam}$ oxygenase from *P. putida* (SEQ ID NO:2) in promoting the oxygenation of an oxygenase substrate in the presence of an oxygen donor, at least 99% sequence identity to SEQ ID NO:2, and a mutation in at least one position corresponding to one of amino acids 242, 280, and 331 of SEQ ID NO:2.

5. A cytochrome P450 oxygenase variant having a stability at least two times the stability of wild-type cytochrome P450$_{cam}$ oxygenase from *P. putida* (SEQ ID NO:2) in promoting the oxygenation of an oxygenase substrate in the presence of an oxygen donor, at least 99% sequence identity to SEQ ID NO:2, and a mutation in at least one position corresponding to one of amino acids 242, 280, and 331 of SEQ ID NO:2.

6. A cytochrome P450 oxygenase variant comprising a sequence selected from the group consisting of SEQ ID NO: 11, SEQ ID NO: 12, and SEQ ID NO:13.

7. A functional cytochrome P450 oxygenase variant identified by a method comprising the steps of:
   (a) contacting a test cytochrome P450 oxygenase variant with an oxygenase substrate and an oxygen donor under conditions allowing the formation of an oxygenated product if said test enzyme variant is an oxygenase enzyme;

(b) providing a coupling enzyme which is capable of promoting the formation of a detectable composition from the oxygenated product;

(c) detecting the detectable composition; and (d) selecting any test enzyme having a mutation at a position corresponding to at least one of amino acid 331, 280, and 242 of cytochrome P450$_{cam}$ from *P. putida* (SEQ ID NO:2) and at least 99% sequence identity to SEQ ID NO:2.

8. The cytochrome P450 oxygenase variant of claim 7, wherein the detecting of the detectable composition comprises detection of at least one of ultraviolet light, color change, fluorescence, and luminescence.

9. The cytochrome P450 oxygenase variant of claim 7, wherein (a) the organic substrate is selected from the group consisting of naphthalene, 3-phenylpropionate, benzene, toluene, benzoic acid, anthracene, benzphetamine, and coumarin;

(b) the oxygen donor is selected from the group consisting of hydrogen peroxide and t-butyl peroxide; and (c) the coupling enzyme is selected from the group consisting of horseradish peroxidase, cytochrome c peroxidase, tulip peroxidase, lignin peroxidase, carrot peroxidase, peanut peroxidase, soybean peroxidase, and NOVOZYME® 502.

10. The cytochrome P450 variant of claim 1, comprising mutations at amino acids 242, 280, and 331 of SEQ ID NO:2.

11. The cytochrome P450 variant of claim 4, comprising at least one mutation selected from lysine at amino acid 331, leucine at amino acid 280, and phenylalanine at amino acid 242.

12. The cytochrome P450 variant of claim 4, wherein the oxygen donor is a peroxide.

13. The cytochrome P450 variant of claim 12, wherein the peroxide is selected from hydrogen peroxide and t-butyl peroxide.

14. The cytochrome P450 variant of claim 5, comprising at least one mutation selected from lysine at amino acid 331, leucine at amino acid 280, and phenylalanine at amino acid 242.

15. The cytochrome P450 variant of claim 5, wherein the oxygen donor is a peroxide.

16. The cytochrome P450 variant of claim 15, wherein the peroxide is selected from hydrogen peroxide and t-butyl peroxide.

17. The cytochrome P450 variant of claim 15, wherein the peroxide is selected from hydrogen peroxide and t butyl peroxide.

* * * * *